(12) United States Patent
Tada et al.

(10) Patent No.: US 8,110,660 B2
(45) Date of Patent: Feb. 7, 2012

(54) SOLUBLE ENPP4 PROTEIN

(75) Inventors: Hideaki Tada, Tsukuba (JP); Tomoyuki Bando, Tsukuba (JP); Akio Hayashi, Tsukuba (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 1236 days.

(21) Appl. No.: 11/719,730

(22) PCT Filed: Nov. 18, 2005

(86) PCT No.: PCT/JP2005/021236
§ 371 (c)(1),
(2), (4) Date: May 18, 2007

(87) PCT Pub. No.: WO2008/078334
PCT Pub. Date: Jul. 3, 2008

(65) Prior Publication Data
US 2010/0240583 A1  Sep. 23, 2010

(30) Foreign Application Priority Data
Nov. 19, 2004 (JP) ................................. 2004-336732

(51) Int. Cl.
*C07K 1/00* (2006.01)
*C07K 14/00* (2006.01)
*C07K 17/00* (2006.01)

(52) U.S. Cl. ...................................................... 530/350

(58) Field of Classification Search ........................ None
See application file for complete search history.

(56) References Cited

U.S. PATENT DOCUMENTS
7,189,546 B2 * 3/2007 Fukushima et al. .......... 435/183

FOREIGN PATENT DOCUMENTS
EP    1022286 A1   7/2006
WO   99/18126 A1   4/1999

OTHER PUBLICATIONS

Bollen, M, et al., Neucleotide pyrophosphatases/phosophordiesterases on the move, Crit. Rev. Biochem. Mol. Biol., vol. 35, No. 6, 2000, pp. 393 to 432.
Gijsbers, R. et al., Structural and catalytic similarities between nucleotide pyrophosphatases/phosophordiesterases and alkaline phosphatases, J. Biol. Chem., vol. 276, No. 2, Jan. 12, 2001., pp. 1361 to 1368.
Goding, J.W. et al., Physiological and pathophysiological functions of the ecto-nucleotide pyrophosphatases/phosphodiesterase family. Biochim. Biophys. Acta., vol. 1638, No. 1, May 20, 2003, pp. 1 to 19.
Kishorel, B.K. et al., Cellular localization of nucleotide pyrophosphatases/phosphodiesterase (NPPs)in rat kidney, FASEB J., vol. 18, No. 4, Mar. 23, 2004, Abstract—473.13.
Sakagami, H. et al., Biochemical and molecular characterization of a novel choline-specific glycerophosphodiester phosphodiesterase belonging to the nucleotide pyrophosphatase/phosphordiesterase family, J. Biol. Chem., vol. 280, No. 24, Jun. 17, 2005, pp. 23084 to 23093.

* cited by examiner

*Primary Examiner* — Robert Landsman
(74) *Attorney, Agent, or Firm* — Sughrue Mion, PLLC

(57) ABSTRACT

The present invention relates to a method for screening a medicine using a protein, and a compound obtained by the screening method.
A compound or a salt thereof inhibiting activity or expression of the protein of the present invention, a neutralizing antibody against the protein, a polynucleotide that are complementary to a polynucleotide coding the protein, and the like can be used as an agent for preventing and/or treating neurodegenerative diseases and the like. Moreover, a compound or a salt thereof enhancing activity or expression of the protein of the present invention, the protein or a partial peptide thereof, a polynucleotide coding the protein, and the like can be used as an agent for preventing and/or treating cancers and the like. Furthermore, the protein of the present invention is useful as a reagent for screening a compound inhibiting or enhancing activity of the protein.

2 Claims, 11 Drawing Sheets

SOLUBLE ENPP4 PROTEIN

TECHNICAL FIELD

The present invention relates to a soluble type protein and utilization thereof. More specifically, the present invention relates to a soluble type protein, a method for producing the protein, a method for screening a compound having an action regulating activity of the protein using the protein and the like, and the like.

BACKGROUND ART

It has been reported that the amino acid sequence of Ecto-nucleotide pyrophosphatase/phosphodiesterase 4 (ENPP4) derived from human and the DNA coding the sequence, and however its function has not been demonstrated (Patent Document 1, Patent Document 2, Patent Document 3, Patent Document 4, Patent Document 5, Patent Document 6). It has been reported that the amino acid sequence of Ecto-nucleotide pyrophosphatase/phosphodiesterase 5 (ENPP5) derived from human and the DNA coding the sequence, and however its function has not been demonstrated (Patent Document 7, Patent Document 8, Patent Document 9, and Non-Patent Document 1). It has been reported that the amino acid sequence of Ecto-nucleotide pyrophosphatase/phosphodiesterase 6 (ENPP6) derived from human and the DNA coding the sequence (Patent document 10, Patent document 11, Non-Patent Document 1, Non-Patent Document 2). It has been reported that ENPP6 has phosphodiesterase/phosphomonoesterase (PDE/PME) activity and phospholipase C (PLC) activity and also Choline-specific Glycerophosphodiester Phosphodiesterase activity and degrades LPC, SPC, and GPC (Non-Patent Document 3).

Patent Document 1: International Publication No. WO 99/18126
Patent Document 2: International Publication No. WO01/77137
Patent Document 3: International Publication No. WO02/08278
Patent Document 4: International Publication No. WO01/34768
Patent Document 5: US Patent No. 2003/104426
Patent Document 6: US Patent No. 2002/193567
Patent Document 7: US Patent No. 2003/022331
Patent Document 8: International Publication No. WO01/55358
Patent Document 9: International Publication No. WO01/60860
Patent document 10: US Patent No. 2003/215909
Patent document 11: EP Patent No. 1293569
Non-Patent Document 1: *Genome Res.*, 13, 2265-2270, 2003
Non-Patent Document 2: *Nat. Genet.*, 36, 40-45, 2004
Non-Patent Document 3: *J. Biol. Chem.*, 280, 23084-93, 2005

DISCLOSURE OF THE INVENTION

Problems to be Solved by the Invention

A method for effectively screening a medicine has been required to be found.

Means for Solving the Problems

The present inventors have thoroughly investigated to solve the above problems and consequently, found that an isolated and purified a soluble type protein of ENPP4 has a nucleotide pyrophosphatase/phosphodiesterase (NPP/PDE) activity and a phosphodiesterase/phosphomonoesterase (PDE/PME) activity and degrades diadenosine polyphosphate (Ap(n)A), UDP-Glucose, CDP-Choline and the like, and degrades Ap(4)A to generate ATP. It has been known that ATP and diadenosine 5-phosphate (Ap(5)A) induce the increase of intracellular calcium ions in an aminergic ganglion end and transmit stimulation (*Journal of Neuroscience Research* 64, 174-82, 2001) through P2X receptor expressing in a central nerve, and that diadenosine polyphosphate such as Ap(4)A induces the increase of intracellular calcium ions and transmits stimulation (*Pharmacology & Therapeutics* 87, 103-115, 2000) through a diadenosine polyphosphate receptor (P4 receptor), and that Ap(4)A has an action for protecting a nerve cell against cerebral ischemia (*The Journal of Neuroscience* 23, 7958-65, 2003), and that diadenosine polyphosphate Ap(n)A such as Ap(4)A relates to tension and relaxation of blood vessel on a P2X or P2Y receptor (*The Journal of Pharmacology and Experimental Therapeutics* 302, 787-94, 2002). Moreover, it has been known that P2X and P2Y receptors are also expressed in gastrointestinal tract epithelial cells or nerve cells of an epithelial tissue and relates to mucus secretion and muscle contraction (*News in Physiological sciences* 18, 43-49, 2002, *Current Topics in Medicinal Chemistry*, 4, 793-803, 2004). It has been known that UDP-Glucose relates to regulation of immune function such as suppression of proliferation of T cells on a P2Y14 receptor (*British Journal of Pharmacology* 146, 435-444, 2005). The present inventors indicates that degradation of these nucleic acids by ENPP4 regulates transmission of aminergic neural stimulation and attenuates the action for protecting nerve cells and regulates blood vessel contraction and regulates mucus secretion in a digestive organ and muscle contraction and regulates immune function and the like. Therefore, it is thought that substances inhibiting the action based on ENPP4 can serve as preventive and/or therapeutic agents against neurodegenerative diseases such as Parkinson's disease and Alzheimer's disease, cerebral ischemic diseases such as cerebral infarction and cerebral stroke, psychoneurotic diseases such as manic-depressive psychosis, autoimmune diseases. Moreover, it is thought that ENPP4 and substances regulating an action based on ENPP4 can serve as an agent for preventing and/or treating circulatory diseases such as high-blood pressure, gastrointestinal diseases such as inflammatory bowel disease and colon cancer.

The present inventors have also found that the isolated and purified soluble type protein of ENPP5 has an NPP/PDE activity, a PDE/PME activity, and a PLC activity. It has been known that extracellular ATP and adenosine-2-phosphate (ADP) relates to signal transduction and antigen presentation function of dendric cells or microphages with T cells through a P2 receptor (*J. Lekocyte Biol.* 73, 339-343, 2003, *Proc. Natl. Acad. Sci.* 101, 9479-84, 2004), and that an induction of the P2 receptor desensitization due to excessively generation of extracellular ATP minimized allergic dermatitis in a knockout mouse of CD39, which is a extracellular nucleic acid-degrading enzyme (*Nat. Med.* 8, 358-365, 2002), and that the extracellular ATP has a suppressive effect on endotoxic shock by lipopolysaccharide (LPS) (*Proc. Natl. Acad. Sci.* 91, 6017-6020, 1994), and the like. With considering the later-described knowledge of the present inventors that ENPP5 is expressed limitedly in an internal organ of immune system, it is indicated that ENPP5 relates to regulation of biological defense function due to degradation of these nucleic acids. Therefore, it is thought that a substance inhibiting an action based on ENPP5 can serves as an agent for preventing and/or treating allergic diseases such as autoimmune disease and skin inflammation, infectious diseases such as blood poisoning, or inflammatory diseases.

The present inventors have also found that the isolated and purified soluble type protein of ENPP6 have an NPP/PDE activity and a PDE/PME activity, and degrade sphingomyelin (SM) and generate ceramide (Cer). SM is degraded by sphingomyelinase (SMase) and Cer is released. It has been known that Cer induces apoptosis and suppression of cell proliferation (*Biochimica et Biophysica Acta* 1585, 114-25, 2002). Moreover, it has been reported that ENPP7 belonging to the ENPP family also retains the SMase activity under alkali and relates to suppression of proliferation of colon cancers by releasing Cer (*J. Cancer Res. Clin. Oncol.* 129, 577-82, 2003). On the other hand, it has been reported that Cer accumulates in an aged brain or a brain of Alzheimer's patient (*Proc. Natl. Acad. Sci.* 101, 2070-75, 2004) and that increase of Cer can be observed in Zellweger syndrome and in adrenoleucodystrophy (ALD) (*Rapid Communications in Mass Spectrometry* 18, 1569-74, 2004). The present inventors indicates that ENPP6 relates to damage and proliferation suppression of cancer cells or nerve cells or the like by degrading SM. Therefore, it is thought that the substance inhibiting an action based on ENPP6 can serves as an agent for preventing and/or treating neurodegenerative diseases such as Alzheimer's disease, Zellweger syndrome, and ALD. Moreover, it is thought that ENPP6 or a substance enhancing the action based on ENPP6 can serves as an effective anti-cancer agent.

The present inventors thoroughly investigated and consequently completed the present invention according to the above finding.

That is, the present invention relates to:

[1] An isolated protein or a partial peptide thereof, comprising a same or substantially same amino acid sequence as an amino acid sequence represented by any one selected from SEQ ID NOs:7, 8, and 9;

[2] The protein or the partial peptide thereof according to the above [1], comprising the same or substantially same amino acid sequence as an amino acid sequence represented by SEQ ID NO:7;

[3] The protein or the partial peptide thereof according to the above [1], comprising the same or substantially same amino acid sequence as an amino acid sequence represented by SEQ ID NO:8;

[4] The protein or the partial peptide thereof according to the above [1], comprising the same or substantially same amino acid sequence as an amino acid sequence represented by SEQ ID NO:9;

[5] A polynucleotide comprising a base sequence coding the protein according to any one of the above [1] to [4];

[6] A polynucleotide comprising a base sequence represented by any one selected from SEQ ID NOs:10, 11, and 12;

[7] The polynucleotide according to the above [6], comprising the base sequence represented by SEQ ID NO:10;

[8] The polynucleotide according to the above [6], comprising a base sequence represented by SEQ ID NO:11;

[9] The polynucleotide according to the above [6], comprising a base sequence represented by SEQ ID NO:12;

[10] A recombinant vector comprising the polynucleotide according to any one of the above [5] and [6];

[11] A transformant obtained by transforming a host cell with the recombinant vector according to the above [10];

[12] A method for producing the protein, comprising culturing the transformant according to the above [11], and thereby generating the protein according to the above [1];

[13] A method for screening a compound regulating activity of the protein comprising a same or substantially same amino acid sequence as an amino acid sequence represented by any one selected from SEQ ID NOs:7, 8, and 9, comprising the steps of:

(1) contacting the protein with the substrate in presence of a test compound;

(2) detecting a degraded product of the substrate that is generated in the step (1); and (3) comparing the amount of the degraded product of the substrate in presence or absence of the test compound;

[14] The method according to the above [13], wherein the protein comprises the same or substantially same amino acid sequence as an amino acid sequence represented by SEQ ID NO:7;

[15] The method according to the above [13], wherein the protein comprises the same or substantially same amino acid sequence as an amino acid sequence represented by SEQ ID NO:8;

[16] The method according to the above [13], wherein the protein comprises the same or substantially same amino acid sequence as an amino acid sequence represented by SEQ ID NO:9;

[17] A method for screening a compound regulating activity of a protein comprising a same or substantially same amino acid sequence as an amino acid sequence represented by any one selected from SEQ ID NOs:7, 8, and 9, comprising the steps of:

(1) culturing the transformant according to the above [11] and adding a test compound and the substrate in a culture medium;

(2) detecting a degraded product of the substrate that is generated in the step (1); and (3) comparing the amount of degraded product of the substrate in presence or absence of the test compound;

[18] The method according to the above [17], wherein the transformant is transformed with a vector including a polynucleotide containing a base sequence coding the protein according to the above [2];

[19] The method according to the above [17], wherein the transformant is transformed with a vector including a polynucleotide containing a base sequence coding the protein according to the above [3];

[20] The method according to the above [17], wherein the transformant is transformed with a vector including a polynucleotide containing a base sequence coding the protein according to the above [4];

[21] A method for screening a compound regulating activity of a protein comprising a same or substantially same amino acid sequence as an amino acid sequence represented by any one selected from amino acids 16 to 453 of SEQ ID NO:1, amino acids 23 to 477 of SEQ ID NO:2, and amino acids 23 to 440 of SEQ ID NO:3, comprising the steps of:

(1) culturing a cell expressing the protein comprising a same or substantially same amino acid sequence as an amino acid sequence represented by any one selected from amino acids 16 to 453 of SEQ ID NO:1, amino acids 23 to 477 of SEQ ID NO:2, and amino acids 23 to 440 of SEQ ID NO:3, and adding a test compound and the substrate in a culture medium;

(2) detecting a degraded product of the substrate that is generated in the step (1); and (3) comparing the amount of the degraded product of the substrate in presence of the test compound;

[22] The method according to the above [21], wherein the cell is transformed with a vector including a polynucleotide containing a base sequence coding the protein comprising a same or substantially same amino acid sequence as an amino acid sequence represented by amino acids 16 to 453 of SEQ ID NO:1;

[23] The method according to the above [21], wherein the cell is transformed with a vector including a polynucleotide containing a base sequence coding the protein comprising a same or substantially same amino acid sequence as an amino acid sequence represented by amino acids 23 to 477 of SEQ ID NO:2;

[24] The method according to the above [21], wherein the cell is transformed with a vector including a polynucleotide containing a base sequence coding the protein comprising a same or substantially same amino acid sequence as an amino acid sequence represented by amino acids 23 to 440 of SEQ ID NO:3;

[25] The method according to the above [14], [18] or [22], wherein the substrate is p-nitrophenyl phenylphosphonate (pNP-PP) or p-nitrophenyl-Thymidine monophosphate (pNP-TMP);

[26] The method according to the above [15], [19] or [23], wherein the substrate is pNP-PP, pNP-TMP, or p-nitrophenyl phosphorylcholine (pNP-PC);

[27] The method according to the above [16], [20] or [24], wherein the substrate is pNP-PP, pNP-TMP, of bis-(p-nitrophenyl)phosphate (bis-pNPP) or pNP-PC;

[28] An agent for preventing and/or treating a disease selected from neurodegenerative diseases, cerebral ischemic diseases, autoimmune diseases, gastrointestinal diseases, and circulatory diseases, comprising a compound regulating activity of a protein comprising a same or substantially same amino acid sequence as an amino acid sequence represented by SEQ ID NO:1 or 7;

[29] An agent for preventing and/or treating a disease selected from autoimmune diseases, allergic diseases, infectious diseases, and inflammatory diseases, comprising a compound inhibiting activity of a protein comprising a same or substantially same amino acid sequence as an amino acid sequence represented by SEQ ID NO:2 or 8;

[30] An agent for preventing and/or treating a disease selected from cancers, neurodegenerative diseases, and renal diseases, comprising a compound regulating activity of a protein comprising a same or substantially same amino acid sequence as an amino acid sequence represented by SEQ ID NO:3 or 9;

[31] A method for preventing and/or treating a disease selected from neurodegenerative diseases, cerebral ischemic diseases, autoimmune diseases, gastrointestinal diseases in a mammal, and circulatory diseases, comprising:
    administering, to the mammal, an effective dose of a compound regulating activity of a protein comprising a same or substantially same amino acid sequence as an amino acid sequence represented by SEQ ID NO:1 or 7;

[32] A method for preventing and/or treating a disease selected from autoimmune diseases, allergic diseases, infectious diseases, and inflammatory diseases in a mammal, comprising:
    administering, to the mammal, an effective dose of a compound inhibiting activity of a protein comprising a same or substantially same amino acid sequence as an amino acid sequence represented by SEQ ID NO:2 or 8;

[33] A method for preventing and/or treating a disease selected from cancers, neurodegenerative diseases, and renal diseases in a mammal, comprising:
    administering, to the mammal, an effective dose of a compound regulating activity of a protein comprising a same or substantially same amino acid sequence as an amino acid sequence represented by SEQ ID NO:3 or 9;

[34] A use of a compound regulating activity of a protein comprising a same or substantially same amino acid sequence as an amino acid sequence represented by SEQ ID NO:1 or 7, in order to produce an agent for preventing and/or treating a disease selected from neurodegenerative diseases, cerebral ischemic diseases, autoimmune diseases, gastrointestinal diseases, and circulatory diseases;

[35] A use of a compound inhibiting activity of a protein comprising a same or substantially same amino acid sequence as an amino acid sequence represented by SEQ ID NO:2 or 8, in order to produce an agent for preventing and/or treating a disease selected from autoimmune diseases, allergic diseases, infectious diseases, and inflammatory diseases;

[36] A use of a compound regulating activity of a protein comprising a same or substantially same amino acid sequence as an amino acid sequence represented by SEQ ID NO:3 or 9, in order to produce an agent for preventing and/or treating for a disease selected from cancers, neurodegenerative diseases, and renal diseases;

[37] The protein or the partial peptide thereof according to the above [2], wherein the protein comprises a same or substantially same amino acid sequence as an amino acid sequence represented by SEQ ID NO:28;

[38] The protein or the partial peptide thereof according to the above [3], wherein the protein comprises a same or substantially same amino acid sequence as an amino acid sequence represented by SEQ ID NO:29;

[39] The protein or the partial peptide thereof according to the above [4], wherein the protein comprises a same or substantially same amino acid sequence as an amino acid sequence represented by SEQ ID NO:30;

[40] The polynucleotide according to the above [7], wherein the polynucleotide comprises a base sequence represented by SEQ ID NO:25;

[41] The polynucleotide according to the above [8], wherein the polynucleotide comprises a base sequence represented by SEQ ID NO:26;

[42] The polynucleotide according to the above [9], wherein the polynucleotide comprises a base sequence represented by SEQ ID NO:27;

[43] A pharmaceutical composition comprising a compound regulating activity of a protein comprising a same or substantially same amino acid sequence as an amino acid sequence represented by SEQ ID NO:1 or 7;

[44] A pharmaceutical composition comprising a compound inhibiting activity of a protein comprising a same or substantially same amino acid sequence as an amino acid sequence represented by SEQ ID NO:2 or 8; and

[45] A pharmaceutical composition comprising a compound regulating activity of a protein comprising a same or substantially same amino acid sequence as an amino acid sequence represented by SEQ ID NO:3 or 9.

In the present specification and the drawings, pNP-PP is an abbreviation of p-nitrophenyl phenylphosphonate, pNP-TMP is an abbreviation of p-nitrophenyl-Thymidine monophosphate, pNP-PC is an abbreviation of p-nitrophenyl phosphorylcholine, and bis-pNPP is an abbreviation of bis-(p-nitrophenyl)phosphate.

The isolated protein comprising a same or substantially same amino acid sequence as an amino acid sequence represented by any one selected from SEQ ID NOs:7, 8, and 9 (hereinafter, may called as the protein of the present invention) may be a protein derived from a living body or a cultured cell, a protein that is genetically modified, or a synthesized protein.

The substantially same amino acid sequence as an amino acid sequence represented by any one selected from SEQ ID NOs:7, 8, and 9 includes an amino acid sequence comprising a homology of approximately 85% or more, preferably approximately 90% or more, more preferably approximately 95% or more, most preferably approximately 98% or more with the corresponding amino acid sequence represented by any one selected from SEQ ID NOs:7, 8, and 9, and the like. The isolated protein comprising a substantially same amino acid sequence as an amino acid sequence represented by any one selected from SEQ ID NOs:7, 8, and 9 includes, for example, a protein comprising a substantially same amino acid sequence as the corresponding amino acid sequence represented by any one selected from SEQ ID NOs:7, 8, and 9 and that has the activities of substantially identical as that of the protein having the corresponding acid sequence represented by any one selected from SEQ ID NOs:7, 8, and 9 and the like. Here, the activities of substantially identical include, for example, an NPP/PDE activity, a PDE/PME activity, a PLC activity, an activity of degrading sphingomyelin, and the like. The substantially identical means that these activities are qualitatively same. The measurements of the NPP/PDE activity, the PDE/PME activity, the PLC activity, and the activity of degrading sphingomyelin can be performed with reference to known methods. However, they can be performed according to the later-described Examples 4 to 6 or Examples 9 to 11.

Moreover, as well as the protein comprising the amino acid sequence represented by any one selected from SEQ ID NOs: 7, 8, and 9, the protein of the present invention includes, for example, a protein in which the amino acid(s) therein (preferably 1 to 10 amino acid(s), more preferably 1 to 5 amino acid(s), further preferably 1 to 3 amino acid(s)) is/are partially deleted, or a protein in which the amino acid(s) therein (preferably 1 to 10 amino acid(s), more preferably 1 to 5 amino acid(s), further preferably 1 to 3 amino acid(s)) is/are partially substituted by another/other amino acid(s), a protein in which the several amino acid(s) therein (preferably 1 to 10 amino acid(s), more preferably 1 to 5 amino acid(s), further preferably 1 to 3 amino acid(s)) is/are partially added or inserted, and a protein comprising a combined amino acid sequence thereof. In such a case that the amino acid sequence has deletion, substitution, addition, or insertion, its position is not particularly limited.

The protein of the present invention is a soluble type protein. In general, the protein is translated as a precursor protein having a signal peptide at its N-terminal in a living body and then, subjected to processing by a signal peptidase to become a mature (or pro) protein. The proteins having the amino acid sequences represented by SEQ ID NOs:7 to 9 correspond to the mature proteins. The cleavage site of the signal peptide (the N-terminal of the mature (pro) protein) can be determined by, for example, subjecting the completely or partially purified protein of the present invention to Edman degradation method. However, from a primary structure of the precursor protein, the cleavage site can be calculated by using a known mathematical algorithm. Such an algorithm includes, but not limited to, for example, the algorithm described in Nielsen et al., Int. Neural Syst., 8(5-6): 581-599 (1997) [the algorithm has been incorporated into the Signal-P program (available on WWW server: www.cbs.dtu.dk/services/SignalP/)], the algorithm described in Emanuelsson et al., J. Mol. Biol. 300: 1005-1016 (2000) [the algorithm has been incorporated into the Target-P program (available on WWW server: www.cbs.dtu.dk/services/TargetP/)], the algorithm described in von Heijne, Nucl. Acids Res., 14: 4683 (1986) [the algorithm has been incorporated into the PSORT II program (available on WWW server: psort.ims.u-tokyo.acjp/form2.html)], the algorithm incorporated into SOSUI (Signal) program Beta Version (available on WWW server: sosui.proteome.bio.tuat.ac.jp/cgi-bin/sosui.cgi?/sosuisignal/sosuisignal_submit.html), and the like. For example, when the above-described PSORT II program is used, it is calculated that the proteins having the amino acid sequences represented by SEQ ID NO:28, 29, and 30 can be cleaved between the amino acid 15 and 16, between 22 and 23, and between 22 and 23, respectively. However, these do not necessarily correspond to the actual cleavage sites, and also occasionally, the positions to be cleaved of the signals are different according to the cell type that express the protein of the present invention. Therefore, the protein of the present invention also includes a protein comprising each of the amino acid sequences that are the amino acid 16, 23, and more than 23 in each of the amino acid sequences represented by SEQ ID NO:28, 29, and 30, and a protein comprising an amino acid sequence in which one or two or more amino acid(s) is/are added or deleted in each of the amino acid sequences.

Moreover, a constituent amino acid of the protein of the present invention may have a carboxyl group, which may be amidated or esterified. The ester includes, for example, the one esterified by an alkyl group (such as methyl, ethyl, propyl, and butyl), an allyl group (such as phenyl and naphthyl), a cycloalkyl group (such as cyclopentyl and cyclohexyl), and the like. An amino group of a constituent amino acid thereof may be protected by a formyl group, an acetyl group, or the like. Moreover, the protein of the present invention includes a protein to which a sugar chain is connected and the like.

The partial peptide of the protein of the present invention (hereinafter, occasionally, called as the partial peptide of the present invention) may be any peptide that is the partial peptide of the above-described protein of the present invention and has the activities that are substantially identical to the above-described protein of the present invention. For example, there can be used the peptide having an amino acid sequence containing at least 20 or more amino acids, preferably 50 or more amino acids, more preferably 100 or more amino acids, or most preferably 150 or more amino acids of the protein of the present invention, and the like. Moreover, the partial peptide of the present invention includes a peptide in which a part of the amino acid(s) (preferably 1 to 5 amino acid(s), more preferably 1 to 2 amino acid(s)) in the amino acid sequence is/are partially deleted, or a protein in which the several amino acid(s) therein (preferably 1 to 5 amino acid(s), more preferably 1 to 2 amino acid(s)) is/are partially converted to another/other amino acid(s), a protein in which the partial amino acid(s) (preferably 1 to 5 amino acid(s), more preferably 1 to 2 amino acid(s)) is/are partially added or inserted, and a protein having a combined amino acid sequence thereof. In such a case that the amino acid sequence has deletion, conversion, addition, or insertion as described above, its position is not particularly limited.

Moreover, in the partial peptide of the present invention, a constituent amino acid thereof may have a carboxyl group, which may be amidated or esterified. The ester includes, for example, the carboxyl group esterified by an alkyl group (such as methyl, ethyl, propyl, and butyl), an allyl group (such as phenyl and naphthyl), a cycloalkyl group (such as cyclopentyl and cyclohexyl), and the like. An amino group of a constituent amino acid thereof may be protected by a formyl group, an acetyl group, or the like. Moreover, the partial peptide of the present invention includes a peptide to which a sugar chain is connected and the like.

As a salt of the protein or the partial peptide of the present invention, a salt with an acid (such as inorganic acid or organic acid) or a base (such as alkali metal salt) or the like can be used, but an physiologically acceptable acid addition salt is preferred. As such a salt, for example, a salt with an inorganic acid (such as hydrochloric acid, phosphoric acid, sulfuric acid, and hydrobromic acid) or an organic acid (such as formic acid, acetic acid, propionic acid, fumaric acid, citric acid, oxalic acid, malic acid, methanesulfonic acid, benzenesulfonic acid, succinic acid, maleic acid, tartaric acid, and benzoic acid), or the like can be used.

As the polynucleotide (DNA or RNA) comprising a base sequence coding the protein or the partial peptide of the present invention (hereinafter, occasionally, called as the polynucleotide of the present invention. However, when the polynucleotide is RNA, the base represented by the symbol "t" in the base sequence is replaced to uridine.), any polypeptide is possible as long as having a base sequence coding the protein or the partial peptide of the present invention. It is known well that 1 to 6 kind(s) of codon(s) code(s) one amino acid (for example, one kind for Met, and six kinds for Leu). Therefore, without changing the amino acid sequence of the protein or the peptide, the base sequence in the polynucleotide can be changed. By such a conversion in the base sequence, productivity of the protein or the peptide is occasionally improved. The polynucleotide comprising a base sequence coding the protein or the partial peptide of the present invention can be any one of genomic DNA, cDNA, synthetic DNA, RNA, and hybrid of DNA-RNA.

As well as the polynucleotides containing a base sequence represented by SEQ ID NOs:10 to 12, any polynucleotide is possible as the polynucleotide of the present invention as long as the polynucleotide has a base sequence hybridizing with one of the represented polynucleotides under a stringent condition and has a base sequence coding a protein having the substantially same properties as the protein of the present invention. Such a polynucleotide includes DNA and the like having a base sequence having a homology of 85% or more, preferably 90% or more, more preferably approximately 95% or more, or most preferably approximately 98% or more with any one base sequence selected from SEQ ID NOs:10, 11, and 12. The hybridization can be performed according to a known method such as a method described in *Molecular Cloning* (written by Sambrook, J., Fritshch, E. F. and Maniatis, T., and issued by Cold Spring Harbor Laboratory Press in 1989) or in *Gene*, vol 10, page 63 (1980) or the like. The hybridization condition can be determined by appropriately selecting temperature, ion intensity, primer length, and the like. However, in general, as the temperature is higher or as the ion intensity is lower, the stringency becomes higher. A high stringent condition includes, for example, that the hybridization is performed at 65° C. with a buffer solution containing 0.5M NaHPO$_4$, 7% SDS, and 1 mM EDTA and then a washing is performed at 65° C. with a buffer solution containing 0.1× SSC and 0.1% SDS.

The polynucleotide comprising a base sequence coding the protein having an amino acid sequence represented by SEQ ID NO:7 is preferably the polynucleotide having the base sequence represented by SEQ ID NO:10.

The polynucleotide comprising a base sequence coding the protein having an amino acid sequence represented by SEQ ID NO:8 is preferably the polynucleotide having the base sequence represented by SEQ ID NO:11.

The polynucleotide comprising a base sequence coding the protein having an amino acid sequence represented by SEQ ID NO:9 is preferably the polynucleotide having the base sequence represented by SEQ ID NO:12.

The polynucleotide having a base sequence coding the protein having the amino acid sequence represented by SEQ ID NO:28 (a precursor protein of the protein having the amino acid sequence represented by SEQ ID NO:7) is preferably a polynucleotide having a base sequence represented by SEQ ID NO:25 (the base sequence of base No. 1 to 1212 of the base sequence represented by SEQ ID NO:13).

The polynucleotide having a base sequence coding the protein having the amino acid sequence represented by SEQ ID NO:29 (a precursor protein of the protein having the amino acid sequence represented by SEQ ID NO:8) is preferably a polynucleotide having a base sequence represented by SEQ ID NO:26 (the base sequence of base No. 1 to 1287 of the base sequence represented by SEQ ID NO:14).

The polynucleotide having a base sequence coding the protein having the amino acid sequence represented by SEQ ID NO:30 (a precursor protein of the protein having the amino acid sequence represented by SEQ ID NO:9) is preferably a polynucleotide having a base sequence represented by SEQ ID NO:27 (the base sequence of base No. 1 to 1269 of the base sequence represented by SEQ ID NO:15).

The polynucleotide having a base sequence coding the protein or the partial peptide of the present invention can be obtained by chemical synthesis, by amplification by PCR method by using synthetic DNA primers each having the base sequence coding a part of the protein or the partial peptide of the present invention, or by hybridization method in which a synthetic DNA having the base sequence coding a part of the protein or the partial peptide of the present invention is used as a probe. A human tissue used for obtaining the polynucleotide having the base sequence coding the protein or the partial peptide of the present invention by PCR method or by hybridization method includes cerebrum and the like. By a standard recombinant DNA technique, mRNA is taken out of the above-described tissue to produce cDNA library. For example, the library is screened by using a specific probes synthesized according to the base sequences represented by SEQ ID NOs:10 to 12, to obtain a desired cDNA. Alternatively, sense and antisense primers for amplifying the desired base sequence according to the base sequences represented by SEQ ID NOs:10 to 12 is synthesized, and then PCR is performed by using the cDNA library as a template, and thereby the desired polynucleotide can be amplified. It is preferable that PCT is conducted by using an automated thermal cycler. The reaction can be performed by conducting approximately 25 to 40 cycles each having a step of denaturing DNA under existence of a heat-resistant polymerase (such as Taq), the template DNA, and primers (for example, at 98° C. for 10 to 30 sec), a step of annealing the primers (for example, at 56° C. for 30 sec to 1 min), and a step of elongation reaction under coexistence of four kinds of substrates (dNTP) (for example, at 72° C. for 30 sec to 10 min), and then heating at 70 to 75° C. for 5 to 15 min. Moreover, recently, various kinds of human cDNA libraries have been marketed. In the case of using them, PCR can be performed according to a method described in the appended instruction. A method for the hybridization can be performed according to, for example, a method described in Molecular Cloning (as described above) or in Gene (as described above). The polynucleotide obtained by such a method is incorporated into a recombinant vector and then, introduced into an appropriate host and proliferated and thereby, its required amount can be obtained.

The polynucleotide of the present invention can be used as a template for producing a large amount of the protein or the partial peptide of the present invention and additionally can be used for examining expression of the protein of the present invention in a tissue or a cell by being labeled with an enzyme or the like. That is, the polynucleotide is used as a probe and thereby, expression level of mRNA of the protein of the present invention serves as an index and it is possible to diagnose neurodegenerative diseases, cerebral ischemic diseases, circulatory diseases, autoimmune diseases, allergic diseases, inflammatory diseases, cancers, gastrointestinal diseases, renal diseases, infectious diseases, psychoneurotic diseases, and the like. Also, the polynucleotide of the present invention is introduced into cells in a living body and thereby, can be used as a gene therapy for preventing or treating circulatory diseases, cancers, and the like. Furthermore, the polynucleotide according to the present invention can also be used in screening of compounds (low-molecular compound, peptide, and the like) of decreasing or increasing the expression level of the protein of the present invention. The compounds obtained by such a method can be used as an agent for preventing and/or treating diseases to which the protein of the present invention relates, such as neurodegenerative diseases, cerebral ischemic diseases, circulatory diseases, autoimmune diseases, allergic diseases, inflammatory diseases, cancers, gastrointestinal diseases, renal diseases, infectious diseases, psychoneurotic diseases, and the like. Moreover, by using the polynucleotide of the present invention, a transgenic animal, a knockout animal, and the like can be produced according to known methods.

The method for obtaining the protein or the partial peptide of the present invention includes:
(1) a method for purifying and isolating it from a living body or culture cells;
(2) a method for synthesizing a peptide;
(3) a method for producing it by using a recombinant DNA technique; and the like. However, the method described in (3) is industrially preferable. As such a general technique, there can be used a standard technique as described in Molecular Cloning (as described above) or in Current Protocols in *Molecular Biology* (edited by Ausubel, F. M. et al., and issued by John Wiley & Sons, Inc. in 1989).

The expression system for producing the protein or the peptide by using a recombinant DNA technique (host-vector system) includes, for example, expression systems of bacterium, yeast, insect cells, and mammal cells.

For example, in the case of expressing it in coli bacillus, an initiation codon (ATG) is added at 5' end of the base sequence coding the mature protein portion or the mature soluble type protein portion or the partial peptide thereof. The obtained cDNA is connected to a downstream of an appropriate promoter (such as trp promoter, lac promoter, λPL promoter, and T7 promoter) and then inserted into a vector functioning in coli bacillus (such as pBR322, pUC18, and pUC19), and thereby an expression vector is produced. Next, the coli bacillus (such as *E. Coli* DH1, *E. Coli* JM109, and *E. Coli* HB 101 strains) transformed with the expression vector is cultured in an appropriate culture medium, and a desired protein or peptide can be obtained from the bacteria body. Moreover, if a signal peptide of bacterium (such as a signal peptide of pelB) is utilized, the desired protein or peptide can be secreted in its periplasm. Furthermore, a fusion protein with another protein can also be produced.

Moreover, in the case of expressing it in yeast, the polynucleotide having a base sequence coding the protein or the partial peptide of the present invention is connected to a downstream of an appropriate promoter (such as PHO5 promoter, PGK promoter, GAP promoter, and ADH promoter) and inserted into a vector functioning in yeast (such as pSH19 and pSH15) and thereby, an expression vector is produced. Next, the yeast (such as *saccharomyces cerevisiae* AH22, AH22R⁻, 20B-12, *schizosaccharomyces pombe* NCYC1913, and *pichia pastoris* KM71) transformed with the expression vector is cultured in an appropriate culture medium, and thereby the desired protein or peptide can be obtained.

Moreover, in the case of expressing it in insect cells, the polynucleotide having a base sequence coding the protein or the partial peptide of the present invention is connected to a downstream of an appropriate promoter (such as polyhedrin promoter and P10 promoter) and inserted into a virus vector functioning in insect cells and thereby, an expression vector is produced. As the insect cells, in the case that the virus is AcNPV, the established cell line derived from larva of *Mamestra brassicae* (Sf cells) is used. in the case that the virus is BmNPV, the established cell line derived from silkworm (BmN cells) and the like are used. As the Sf cells, for example, Sf9 cells (ATCC CRL1711), Sf21 cells (Vaughn, J. L., In Vivo, vol. 13, pages 213-217, 1977), and the like are used. As the insect, larva of silkworm and the like are used. Transformation of insect cells or insect can be performed according to, for example, the method described in *Bio/Technology*, Vol. 6, pages 47-55, (1988).

Moreover, in the case of expressing it in a mammal cells, the polynucleotide having a base sequence coding the protein or the partial peptide of the present invention is inserted into a downstream of an appropriate promoter (such as SV40 promoter, LTR promoter, and metallothionein promoter) in an appropriate vector (such as retrovirus vector, papillomavirus vector, vacciniavirus vector, and SV40-based vector) and thereby, an expression vector is produced. Next, an appropriate mammal cells (such as human HEK293T cell, monkey COS-1 cell, COS-7 cell, chinese hamster CHO cell, mouse L cell, and NS0 cell) is transformed with the obtained expression vector and then the transformant is cultured in an appropriate culture medium and thereby, the protein or the partial peptide of the present invention is expressed. Furthermore, by connecting the polynucleotide to cDNA fragment coding another protein such as Fc portion of an antibody and thereby, a fusion protein can also be produced.

Moreover, when the protein of the present invention is expressed as a precursor protein having a signal peptide, the desired protein can be secreted in the culture medium. For example, the protein of the present invention having the amino acid sequence represented by SEQ ID NO:7 may be expressed as the protein having the amino acid sequence represented by SEQ ID NO:28, the protein of the present invention having the amino acid sequence represented by SEQ ID NO:8 may be expressed as the protein having the amino acid sequence represented by SEQ ID NO:29, and the protein of the present invention having the amino acid sequence represented by SEQ ID NO:9 may be expressed as the protein having the amino acid sequence represented by SEQ ID NO:30.

Moreover, as the method for producing a protein or peptide by using a recombinant DNA technique, a non-cell synthesis system (Sambrook J. et al.: *Molecular Cloning*, 2ed. 1989, and the like) can also be utilized.

The protein or the partial peptide obtained as described above can be isolated and purified by a general biochemical method such as salting out, ion-exchange chromatograph, hydrophobic chromatography, affinity chromatography, reverse phase chromatography, adsorption chromatography, chromatofocusing, isoelectric precipitation, gel filtration, ultrafiltration, and the like.

Moreover, the protein or the partial peptide of the present invention can be expressed as a fusion protein with another protein or a tag (Fc region of an antibody, glutathione S-transferase, protein A, FLAG tag, hexahistidine tag, and the like). The fusion protein has an advantage of being capable of be purified by affinity chromatography and/or cut out by an appropriate protease (such as enterokinase and thrombin) and efficiently purified.

The protein or the partial peptide of the present invention can be used as an agent for preventing and/or treating diseases to which the protein of the present invention relates to, such as circulatory diseases and cancers. Moreover, the protein or the partial peptide of the present invention can be used in a screening in screening of compounds (low-molecular compound, peptide, and the like) of inhibiting or enhancing the activities of the protein. The compounds obtained by such a method can also be used as an agent for preventing and/or treating diseases to which the protein of the present invention relates, such as neurodegenerative diseases, cerebral ischemic diseases, circulatory diseases, autoimmune diseases, allergic diseases, inflammatory diseases, cancers, and the like. Furthermore, the protein or the partial peptide of the present invention can also be used in production of monoclonal or polyclonal antibody by using it as an antigen.

A compound of decreasing the expression level of the protein having the amino acid sequence represented by SEQ ID NO:7, a compound of inhibiting an activity of the protein, or an antibody against the protein can be used as an agent for preventing and/or treating neurodegenerative diseases, cerebral ischemic diseases, psychoneurotic diseases, autoimmune diseases, circulatory diseases, or gastrointestinal diseases. Among the above-described object diseases, neurodegenerative diseases, cerebral ischemic diseases, psychoneurotic diseases, and autoimmune diseases are preferable.

A compound of decreasing the expression level of the protein having the amino acid sequence represented by SEQ ID NO:8, a compound of inhibiting an activity of the protein, or an antibody against the protein can be used as an agent for preventing and/or treating allergic diseases, infectious diseases, inflammatory diseases or autoimmune diseases.

A compound of decreasing the expression level of the protein having the amino acid sequence represented by SEQ ID NO:9, a compound of inhibiting an activity of the protein, or an antibody against the protein can be used as an agent for preventing and/or treating neurodegenerative diseases, or renal diseases. Among the above-described object diseases, the neurodegenerative diseases are preferable.

A compound of increasing the expression level of the protein having the amino acid sequence represented by SEQ ID NO:9, or a compound of enhancing an activity of the protein can be used as an agent for preventing and/or treating cancers.

The antibody against the protein or the partial peptide of the present invention may be any one of polyclonal antibody and monoclonal antibody as long as being capable of recognizing the protein or the partial peptide of the present invention. However, in particular, a monoclonal antibody derived from mammal is preferable. As the monoclonal antibody derived from mammal, there are an antibody generated by hybridoma, and an antibody generated by a host transformed with an expression vector containing an antibody gene by a genetic engineering technique.

The antibody generating hybridoma can be produced as follows by using a known technique. That is, the protein or the partial peptide of the present invention is used as a sensitizing antigen, and immunization is performed according to a general immunizing method, the obtained immune cell is fused to a known parent cell by a general cell fusion method, and then the monoclonal-antibody generating cell is cloned by a general screening method. The mammal to be immunized with the sensitizing antigen is not particularly limited. However, it is preferable that the mammal is selected considering its compatibility with the parent cells (myeloma cells) to be used for the cell fusion, and in general, a rodent animal such as mouse, rat, hamster, and the like are used. The immunization of an animal with a sensitizing antigen is performed according to a known method. As the myeloma cell to be fused to the above-described immune cell, various types of known cell lines are available. The cell fusion of the immune cells and the myeloma cells can be performed according to a known method such as the method of Milstein et al. (Kohler, G. and Milstein, C., *Methods Enzymol.*, Vol. 73, pages 3-46, 1981). The obtained fusion cells are selected by being cultured in a general selected culture medium such as HAT culture medium (culture solution containing hypoxanthine, aminopterin, and thymidine). The culturing in this HAT culture medium is continued generally for some days to some weeks until the cells (non fusion cells) except for the objected hybridomas are killed. Next, by conducting a limiting dilution method, screening and cloning of the hybridoma(s) generating antibody that can connect to the protein of the present invention are performed. Culture supernatant of the hybridoma is purified and thereby the antibody can be obtained. The purification can be performed by appropriately combining general biochemical methods such as salting out, ion-exchange chromatograph, and affinity chromatography.

The polyclonal antibody can be produced by a general method for immunizing a mammal (such as rabbit, goat, and sheep) so that the protein or the partial peptide thereof of the present invention serve as a sensitizing antigen, and the antiserum is collected and purified. The purification can be performed by appropriately combining general biochemical methods such as salting out, ion-exchange chromatograph, and affinity chromatography.

Moreover, the antibody can also be obtained by using a genetic engineering technique. That is, mRNA is obtained from splenocytes or lymphocytes of the animal immunized so that the protein or the partial peptide thereof of the present invention serve as a sensitizing antigen, or hybridoma generating monoclonal antibody against the protein or the partial peptide thereof of the present invention, and then by using the mRNA as the template, cDNA library is produced. The clone(s) generating an antibody reacting with the sensitizing antigen is/are screened and the obtained clone is cultured, and from the culture supernatant the object antibody can be purified by appropriately combining general biochemical methods such as salting out, ion-exchange chromatograph, and affinity chromatography. For using an antibody as a medicine, a humanized antibody or a human type antibody which has a low immunogenicity is preferable. The humanized antibody can be produced using a hypervariable region of the above-described monoclonal antibody by a genetic engineering technique (see, for example, *Method in Enzymology*, vol. 203, 99-121, 1991). The human type antibody can be obtained by immunizing a mouse whose immune system is exchanged to that of human (see, *Nat. Genet.*, vol. 15, pages 146-156, 1997).

The neutralizing antibody against the protein or the partial peptide thereof of the present invention can be selected by the following method. That is, a test antibody is added to a system for measuring an NPP/PDE activity or a PDE/PME activity of the protein or the partial peptide of the present invention, and it is evaluated whether the enzyme activity is inhibited or not. A substrate for simply measuring the NPP/PDE activity includes, for example, a synthesized substrate such as p-nitrophenyl-Thymidine monophosphate (pNP-TMP). Moreover, a substrate for simply measuring the PDE/PME activity includes, for example, a synthesized substrate such as p-nitrophenyl phenylphosphonate (pNP-PP) or bis-(p-nitrophenyl)phosphate (bis-pNPP). The neutralizing antibody against the protein or the partial peptide of the present invention can be used as an agent for preventing and/or treating neurodegenerative diseases, cerebral ischemic diseases, circulatory diseases, autoimmune diseases, allergic diseases, inflammatory diseases, and the like. Moreover, the neutralizing antibody can be useful as a reagent for testing neurodegenerative diseases, cerebral ischemic diseases, circulatory diseases, autoimmune diseases, allergic diseases, inflammatory diseases, cancers, and the like.

The polynucleotide having a base sequence that is complementary to the polynucleotide of the present invention or a partial base sequence thereof includes so-called antisense DNA, siRNA, ribozyme, and the like. The antisense DNA against the polynucleotide of the present invention can be produced by inserting a part of the polynucleotide of the present invention (preferably DNA) into an antisense region of such a vector as described above. The siRNA against the polynucleotide of the present invention is a double-strand RNA containing RNA that is complementary to a part of the RNA coding the protein of the present invention. The siRNA can be designed and produced based on a sequence of the polynucleotide of the present invention according to a known method such as *Nature*, vol. 411, pages 494-498, 2001. The ribozyme can be designed and produced based on a sequence of the polynucleotide of the present invention according to a known method (*TRENDS in Molecular Medicine*, vol. 7, page 212, 2001). For example, the ribozyme can be produced by connecting a known ribozyme to one part of RNA coding the protein of the present invention. The part of RNA coding the protein of the present invention includes a part (RNA fragment) that is contiguous to a site that can be cut by the known ribozyme. Such an antisense DNA, siRNA, or ribozyme can degrade the expression level of the protein of the present invention in a cell, and therefore, is useful for an agent for preventing and/or treating neurodegenerative diseases, cerebral ischemic diseases, circulatory diseases, autoimmune diseases, allergic diseases, inflammatory diseases, and the like.

In the present specification, the regulation of an activity of the protein or the partial peptide of the present invention represents inhibition or enhancement of an activity of the protein or the partial peptide. That is, the compound for regulating an activity of the protein or the partial peptide of the present invention represents a compound for inhibiting or enhancing an activity of the protein or the partial peptide.

The method for screening the compound for inhibiting or enhancing an activity of the protein or the partial peptide of the present invention includes, for example, the following method. That is, a test compound is added to a system for measuring an NPP/PDE activity, a PDE/PME activity, or a PLC activity of the protein or the partial peptide of the present invention, and it is evaluated whether the enzyme activity is inhibited or activated. The measurements of an NPP/PDE activity, a PDE/PME activity, and a PLC activity can be performed according to a known method. However, for example, they can be performed according to the later-described Examples 4 to 6, Examples 9 to 11, and Examples 7 to 8, respectively. The NPP/PDE activity can be simply measured by using a synthesized substrate such as p-nitrophenyl-Thymidine monophosphate (pNP-TMP). However, a natural substrate such as ATP or AP(4)A may be used. Moreover, The PDE/PME activity can be simply measured by using a synthesized substrate such as p-nitrophenyl phenylphosphonate (pNP-PP) or bis-(p-nitrophenyl)phosphate (bis-pNPP). Moreover, the PLC activity can be simply measured by using a synthesized substrate such as p-nitrophenyl phosphorylcholine (pNP-PC). However, a natural substrate such as a sphingomyelin may be used. The compound for inhibiting an activity of the protein or the partial peptide of the present invention is useful as a medical drug for prevention and/or treatment for, for example, neurodegenerative diseases, cerebral ischemic diseases, circulatory diseases, autoimmune diseases, allergic diseases, inflammatory diseases. The compound for enhancing an activity of the protein or the partial peptide of the present invention is useful as a medial drug for prevention and/or treatment for, for example, circulatory diseases and cancers.

The test compound includes chemically synthesized compound, peptide, non-peptide compound, protein, fermented product, extract of cells, extract of a plant, extract of an animal tissue, or derivative or modified body thereof, and those compounds may be new compounds or known compounds. The test compound is preferably a chemically synthesized compound.

The method for screening the compound for decreasing or increasing the expression level of the protein of the present invention includes, for example, the following method. That is, cells (such as cells expressing the protein of the present invention) are dispersed on a culture plate, and cultured for a predetermined time with a test compound. RNA is extracted from the cells and the expression level in RNA level is measured by a quantitative RT-PCR by using a specific primer to the protein of the present invention. Alternatively, the antibody against the protein of the present invention is added to the cells after cultured, and next, a second antibody labeled with FITC is added and the protein of the present invention (membrane type protein) that is expressing on the cell surface is quantitatively determined by a flow cytometer. Alternatively, after culturing, the cell lysate solution is prepared, and the expression level in protein level is measured by western blotting by using an antibody against the protein of the present invention. The compounds for decreasing or increasing the expression level of the protein of the present invention can be screened in such methods.

The screening of the compounds for decreasing or increasing the expression level of the protein of the present invention can also be performed by, for example, the following method. That is, there is produced a recombinant vector in which DNA containing an expression control region (such as promoter, enhancer, CAAT box, and TATA box), a 5' non-translated region, and a region contiguous to a translation initiation site, of a gene coding the protein of the present invention, is connected to a reporter gene (luciferase gene, chloramphenicol acetyl transferase (CAT) gene, β-galactosidase gene, and the like). The vector is introduced into an appropriate cell. In presence or absence of a test compound, the cell is cultured under an environment in which the gene coding the protein of the present invention is transcribed, and the expression level of the reporter gene is measured and thereby, the transcription promoting activity or transcription suppressing activity of the test compound is confirmed. The expression control region, the 5' non-translated region, and the region contiguous to a translation initiation site, of a gene coding the protein of the present invention, can be obtained by a known method. Thereby, the compounds for decreasing or increasing the expression level of the protein of the present invention can be selected. The compounds for decreasing the expression level of the protein of the present invention are useful as a medical drug for prevention and/or treatment for, for example, neurodegenerative diseases, cerebral ischemic diseases, circulatory diseases, autoimmune diseases, allergic diseases, and inflammatory diseases. Moreover, the compounds for increasing the expression level of the protein of the present invention are useful as a medial drug for prevention and/or treatment for, for example, circulatory diseases and cancers.

The kit for screening for the present invention includes the protein or the partial peptide of the present invention. However, the kit may contain the antibody against the protein or the partial peptide of the present invention. Moreover, the kit for screening for the present invention include a kit containing cells (such as animal cells) having an ability of generating the protein of the present invention, or a transformant (such as animal cells) transformed with an expression vector having an expression control region of a gene coding the protein of the present invention and a reporter gene.

The compound obtained by the screening method for the present invention, the protein or the partial peptide of the present invention, or the antibody against the protein or the partial peptide of the present invention (occasionally, called as a compound relating to the present invention) is usually administered systemically or locally, or generally administered orally or parenterally.

The administering amount is different, depending on age, weight, symptom, treatment effect, administering method, treatment time, and the like. However, generally, the administration is orally performed at one to some time(s) per one day in the range of 100 μg to 100 mg per one adult and one time, or parenterally performed at one to some time(s) per one day in the range of 10 μg to 100 mg per one adult and one time. Of course, as described above, the administering amount fluctuates according to various conditions, and therefore, occasionally, it is sufficient to administer the smaller amount than the above-described administering amount, or occasionally, the amount exceeding the range is necessary.

When the compound relating to the present invention is administered, the compound is used as a compound such as a solid composition, a liquid composition, another composition for oral administration or an injectable solution, external preparation and suppository for parenteral administration, and the like.

The solid composition for oral administration includes tablets, pills, capsules, powders, granules, and the like. The capsule includes soft capsules and hard capsules.

In such a solid composition, one or more active substance is mixed with at least one inactive diluent (such as lactose, mannitol, glucose, hydroxypropylcellulose, microcrystalline cellulose, starch, polyvinyl pyrrolidone, and magnesium aluminometasilicate). According to an ordinary method, the composition may contain, as well as the inactive diluent, an additive such as a lubricant (such as magnesium stearate), a disintegrating agent (such as cellulose calcium glycolate), a stabilizing agent (such as human serum albumin and lactose), a solubilizing aid (such as arginine and asparagine acid).

The tablet or the pill may be covered with a gastric-soluble or intestinal-soluble film such as sucrose, gelatin, hydroxypropylcellulose, and hydroxypropylmethylcellulose phthalate according to need, or may be covered with two or more layers. Furthermore, a capsule of a material capable of being absorbed such as gelatin is included.

The liquid composition for oral administration includes pharmaceutically acceptable emulsifying agents, solution agents, suspending agents, syrups, elixirs, and the like, and may include an inactive diluent that is generally used (such as purified water and ethanol). Such a composition may contain auxiliary agents such as wetting agents or suspending agents, sweeteners, flavor agents, aromatic agents, and antiseptic agents as well as the inactive diluents.

The other composition for oral administration includes one or more active substance and includes a spray agent prescribed in itself by a known method. This composition may contain a stabilizer such as sodium hydrogen sulfite, a stabilizing agent such as providing isotonicity, an isotonic agent such as sodium chloride, sodium citrate, or citric acid, as well as the inactive diluent. The method for producing a spray agent is described in detail in, for example, U.S. Pat. No. 2,868,691 and U.S. Pat. No. 3,095,355.

The injectable agent for parenterally administration of the present invention includes sterile and an aqueous or non-aqueous solution agent, a suspending agent, and an emulsifying agent. As the aqueous or non-aqueous solution or suspension, one or more active substance(s) is/are mixed with at least one inactive diluent. The aqueous diluent includes, for example, distilled water and a physiological saline solution for injection. The non-aqueous diluent includes, for example, propyleneglycol, polyethyleneglycol, a vegetable oil such as olive oil, alcohol such as ethanol, polysorbate 80®, and the like.

Such a composition may further contain an auxiliary agents such as sterilizers, wetting agents, emulsifying agents, dispersants, stabilizing agents (such as human serum albumin and lactose), solubilizing aids (such as arginine and asparagine acid).

When the polynucleotide of the present invention or the polynucleotide (antisense DNA, siRNA, ribozyme, and the like) having a base sequence that is complementary to the polynucleotide of the present invention or a partial base sequence thereof is used for prevention and/or treatment for neurodegenerative diseases, cerebral ischemic diseases, circulatory diseases, autoimmune diseases, allergic diseases, inflammatory diseases, cancers, and the like, the polynucleotide can be administered to human or mammal according to a general method singularly or after the polynucleotide is inserted into an appropriate vector such as retrovirus vector and adenovirus vector. The polynucleotide can be used as it is or after being made to be a formulation with a physiologically acceptable carrier such as an auxiliary agents (such as liposome and HVJ liposome) for promoting introduction into cells.

The polynucleotide having a base sequence coding a part of the protein or the partial peptide of the present invention or the polynucleotide that is complementary thereto is used, for example, as a primer or a probe and thereby, mRNA of the protein of the present invention can be detected. Therefore, the polynucleotide is useful as a reagent for examining neurodegenerative diseases, cerebral ischemic diseases, circulatory diseases, autoimmune diseases, allergic diseases, inflammatory diseases, cancers, gastrointestinal diseases, renal diseases, infectious diseases, psychoneurotic diseases, and the like. When the polynucleotide of the present invention or the complementary polynucleotide is used as a probe for diagnosis, they are labeled with enzyme, fluorescent material, light-emitting material, radioisotope, or the like, according to a known method. Then, RNA is prepared from the specimen and labeling probes are added and reacted and then, the labeling probes that do not react are removed by cleaning. The mRNA of the protein of the present invention contained in the specimen can be detected as an index of light-emitting, fluorescence, radioactivity, or the like due to the labeled enzyme, fluorescent material, light-emitting material, radioisotope, and the like. Moreover, the antibody against the protein or the partial peptide of the present invention can detect the protein of the present invention and therefore, can be used as a reagent for examining the above-described diseases.

Specifically, the polynucleotide having a base sequence coding a part of the protein or the partial peptide thereof having a same or substantially same amino acid sequence as the amino acid sequence represented by SEQ ID NO:7 or 28 or the polynucleotide that is complementary thereto is useful as a reagent for examining neurodegenerative diseases, cerebral ischemic diseases, psychoneurotic diseases, autoimmune diseases, and the like. The polynucleotide having a base sequence coding a part of the protein or the partial peptide thereof having a same or substantially same amino acid sequence as the amino acid sequence represented by SEQ ID NO:8 or 29 or the polynucleotide that is complementary thereto is useful as a reagent for examining autoimmune diseases, allergic diseases, infectious diseases, inflammatory diseases, and the like. The polynucleotide having a base sequence coding a part of the protein or the partial peptide thereof having a same or substantially same amino acid sequence as the amino acid sequence represented by SEQ ID NO:9 or 30 or the polynucleotide that is complementary thereto is useful as a reagent for examining neurodegenerative diseases, renal diseases, cancers, and the like.

Moreover, the antibody against the protein or the partial peptide thereof having a same or substantially same amino acid sequence as the amino acid sequence represented by SEQ ID NO:7 or 28 is useful as a reagent for examining neurodegenerative diseases, cerebral ischemic diseases, psychoneurotic diseases, autoimmune diseases, and the like. The antibody against the protein or the partial peptide thereof having a same or substantially same amino acid sequence as the amino acid sequence represented by SEQ ID NO:8 or 29 is useful as a reagent for autoimmune diseases, allergic diseases, infectious diseases, inflammatory diseases, and the like. The antibody against the protein or the partial peptide thereof having a same or substantially same amino acid sequence as the amino acid sequence represented by SEQ ID NO:9 or 30 is useful as a reagent for examining neurodegenerative diseases, renal diseases, cancers, and the like.

By using the polynucleotide having a base sequence coding the protein or the partial peptide of the present invention, an animal overexpressing a protein of a wild type or having a mutated sequence or a partial peptide thereof (called as a transgenic animal), an animal that does not express the protein (called as knockout animal), or an animal in which expression of the protein is lowered can be produced. The transgenic animal, the knockout animal, and the like can be produced by a method that is well known to those skilled in the art.

In the present specification, the neurodegenerative diseases include, for example, striatonigral degeneration, Huntington's disease, dancing disease-abnormal movement disease, progressive supranuclear palsy, diffuse Lewy body disease, corticobasal degeneration, Alzheimer's disease, senile dementia (senile cognitive disorders), Pick's disease, frontotemporal dementia (frontotemporal cognitive disorders), familial dementia (familial cognitive disorders), spinocerebellar degeneration (such as olivopontocerebellar atrophy, late cortical cerebellar atrophy, familial spinal cerebellar degeneration (such as McCord-Joseph's disease), dentato rubro pallido luysian atrophy, familial spastic paraplegia, Friedreich's disease), and the like.

In the present specification, the cerebral ischemic diseases include, for example, cerebrovascular disorder (such as cerebral stroke, cerebral infarction (such as cerebral thrombosis and cerebral embolism), transient ischemic attack, reperfusion injury, cerebral hemorrhage (such as hypertensive intracerebral hemorrhage and subarachnoid hemorrhage), and the like.

In the present specification, the psychoneurotic diseases include, for example, neurosis, psychosomatic disorder, anxiety, integration disorder syndrome, manic-depression psychosis, and the like.

In the present specification, the autoimmune diseases include, for example, arthrorheumatism, systemic lupus erythematosus, progressive systemic sclerosis, and the like.

In the present specification, the circulatory diseases include, for example, angina, cardiac failure, congestive heart failure, acute heart failure, chronic heart failure, myocardial infarction, acute myocardial infarction, myocardial infarction prognosis, atrial myxoma, arteriosclerosis, high-blood pressure, dialysis low-blood pressure, thrombosis, diffuse intravascular coagulation syndrome (DIC), reperfusion injury, restenosis after PTCA, and the like.

In the present specification, the allergic diseases include, for example, allergic dermatitis, allergic rhinitis (such as pollen disease), allergic conjunctivitis (such as pollen disease), atopic dermatitis, allergic gastroenteritis, asthma, tracheal asthma, urticata, anaphylactic shock, food allergy, and the like.

In the present specification, the gastrointestinal diseases include, for example, cirrhosis, hepatitis, diarrhea, constipation, gastroptosis, acute gastritis, gastric•chronic gastritis, gastric duodenal ulcer, acute enteritis, chronic enteritis, inflammatory bowel disease, anaphylactic enteritis syndrome, gastric polyposis, colon cancer, gastric cancer, hemorrhoid, and the like.

In the present specification, the inflammatory diseases include, for example, sinus inflammation, adenoiditis, bronchitis, pneumonia, pleuritis, tracheal asthma, chronic emphysema, pneumoconiosis, inflammatory bowel disease, acute pancreatitis, chronic pancreatitis, adult dyspnea syndrome, chronic thyroiditis, autoimmune gastritis, and the like.

In the present specification, the infectious diseases include, for example, virus infection (such as virus infection of cytomegalovirus, influenza virus, herpes virus, corona virus, and the like), cachexia along with infection, cachexia by acquired immunodeficiency syndrome (AIDS), toxemia (such as sepsis, septic shock, endotoxic shock, gram-negative sepsis, toxic shock syndrome, severe acute respiratory syndrome (SARS) along with virus infection), and the like) and the like.

In the present specification, the renal diseases include, for example, acute glomerulonephritis, chronic glomerulonephritis, nephrotic syndrome, pyelonephritis, hypertensive nephrosclerosis, diabetic glomerulonephritis, renal tumor, renal vein thrombosis, and the like.

Effect of the Invention

According to the present invention, it becomes possible to screen substances being capable of regulating an activity of the protein of the present invention.

Specifically, by screening substances of inhibiting an NPP/PDE activity or a PDE/PME activity of the protein having the amino acid sequence represented by SEQ ID NO:1, SEQ ID NO:7, or SEQ ID NO:28, it becomes possible to develop an agent for preventing and/or treating diseases selected from neurodegenerative diseases, cerebral ischemic diseases, gastrointestinal diseases, and circulatory diseases, in which the protein is involved.

Moreover, by screening substances of inhibiting an NPP/PDE activity, a PDE/PME activity, a PLC activity of the protein having the amino acid sequence represented by SEQ ID NO:2, SEQ ID NO:8, or SEQ ID NO:29, it becomes possible to develop an agent for preventing and/or treating diseases selected from autoimmune diseases, allergic diseases, and inflammatory diseases, in which the protein is involved.

Similarly, by screening substances of regulating an NPP/PDE activity, a PDE/PME activity, a sphingomyelin-degrading activity of the protein having the amino acid sequence represented by SEQ ID NO:3, SEQ ID NO:9, or SEQ ID NO:30, it becomes possible to develop an agent for preventing and/or treating diseases selected from cancers, neurodegenerative diseases, and renal diseases, in which the protein is involved.

Furthermore, by using the antibody against the protein of the present invention and the polynucleotide of the present invention, diagnosis or examination of the above-described diseases becomes possible.

BEST MODE FOR CARRYING OUT THE INVENTION

Hereinafter, the present invention will be explained more specifically with reference to Examples. However, the present invention is not limited thereto at all.

Example 1

Expression of Soluble Type Human ENPP4 Protein

The gene coding the protein in which FLAG tag is connected to the C-terminal side of the extracellular region of human ENPP4 (No. 1 methionine to No. 404 leucine in SEQ ID NO:1) and 6×His tag is connected to the C terminal (SEQ ID NO:13, signal peptide; base No. 1 to 45, mature protein; base No. 46 to 1212, FLAG tag and 6×His tag; 1213 to 1254) was cloned into the expression vector pUC-SRαML2 (Japanese Patent Publication No. 8-198899), and thereby ENPP4-FLAG-His expression vector was produced. The expression vector was introduced into HEK293T cells by using LipofectAMINE PLUS (manufactured by Invitrogen Inc.). The cells were cultured for 3 days and then the culture supernatant was collected. The collected culture supernatant was western-blotted according to a predetermined method. The membrane was labeled with horseradish peroxidase (HRP). After reacting with the antibody against 5×His (manufactured by Qiagen Inc.), the band was detected by an ECL detection system (manufactured by Amersham Biosciences Inc.). As a result, as shown in FIG. 1, approximately a 65 kDa band was detected in the culture supernatant of the cells into which the ENPP4-FLAG-His expression vector is introduced.

Example 2

Expression of Soluble Type Human ENPP5 Protein

The gene coding the protein in which FLAG tag is connected to the C-terminal side of the extracellular region of human ENPP5 (No. 1 methionine to No. 429 glycine in SEQ ID NO:2) and 6×His tag is connected to the C terminal (SEQ ID NO:14, signal peptide; base No. 1 to 66, mature protein; base No. 67 to 1287, FLAG tag and 6×His tag; 1288 to 1329) was cloned into the expression vector pUC-SRαML2 (Japanese Patent Publication No. 8-198899), and thereby ENPP5-FLAG-His expression vector was produced. The expression vector was introduced into HEK293T cells by using LipofectAMINE PLUS (manufactured by Invitrogen Inc.). The cells were cultured for 3 days and then the culture supernatant was collected. The collected culture supernatant was western-blotted according to a predetermined method. The membrane was labeled with horseradish peroxidase (HRP). After reacting with the antibody against 5×His (manufactured by Qiagen Inc.), the band was detected by an ECL detection system (manufactured by Amersham Biosciences Inc.). As a result, as shown in FIG. 1, approximately 65 kDa band was detected in the culture supernatant of the cells into which the ENPP5-FLAG-His expression vector is introduced.

Example 3

Expression of Soluble Type Human ENPP6 Protein

The gene coding the protein in which FLAG tag is connected to the C-terminal side of the extracellular region of human ENPP6 (No. 1 methionine to No. 423 proline in SEQ ID NO:3) and 6×His tag is connected to the C terminal (SEQ ID NO:15, signal peptide; base No. 1 to 66, mature protein; base No. 67 to 1269, FLAG tag and 6×His tag; 1270 to 1311) was cloned into the expression vector pUC-SRαML2 (Japanese Patent Publication No. 8-198899), and thereby ENPP6-FLAG-His expression vector was produced. The expression vector was introduced into HEK293T cells by using LipofectAMINE PLUS (manufactured by Invitrogen Inc.). The cells were cultured for 3 days and then the culture supernatant was collected. The collected culture supernatant was western-blotted according to a predetermined method. The membrane was labeled with horseradish peroxidase (HRP). After reacting with the antibody against 5×His (manufactured by Qiagen Inc.), the band was detected by an ECL detection system (manufactured by Amersham Biosciences Inc.). As a result, as shown in FIG. 1, approximately 55 kDa band was detected in the culture supernatant of the cells into which the ENPP6-FLAG-His expression vector is introduced.

Example 4

Purification of Soluble Type Human ENPP4 Protein and Identification of Nucleotide Pyrophosphatase/Phosphodiesterase (NPP/PDE) Activity 400 mL of the culture supernatant of the cells expressing the soluble type human ENPP4 protein was concentrated at 8 times by using Amicon Ultra-15 (fraction molecular weight 10,000, manufactured by Millipore Inc.). The His-Tag-added protein was affinity-purified by using AKTAexplorer 10S (manufactured by Amersham Biosciences Inc.) and His-Trap column (manufactured by Amersham Biosciences Inc.). Samples in the respective purification steps were subjected to SDS-PAGE according to a predetermined method and then the protein was stained by using Simply-Blue-Stain (manufactured by Invitrogen Inc.). As a result, as shown in FIG. 2, the bands of Human ENPP4-FLAG-His protein were detected in the eluted fractions #7-#9. The eluted fractions were dialyzed with PBS by using Slide-A-lyzer dialysis cassette (manufactured by Pierce Inc.), and thereby the purified soluble type human ENPP4-FLAG-His protein was obtained. 40 μL of each of the respective purification steps and purified soluble type human ENPP4-FLAG-His proteins was mixed with 50 μL of assay buffer (20 mM HEPES, 140 mM NaCl, 5 mM KCl, 1 mM $CaCl_2$, 1 mM $MgCl_2$, 10 mM Glucose, pH 9.6, the method of Voltmeter P. et al., *Eur. J. Biochem.* 270 (2003) 2971-78 was improved) and 10 μL of 10 mM p-nitrophenyl-Thymidine monophosphate (pNP-TMP, Sigma Inc.), and the mixture was kept at 37° C. for 2 hours and then, absorption of light of 405 nm was measured and thereby, p-nitorphenol, which was a degradation product, was measured and, whether the Nucleotide Pyrophosphatase (NPP)/Phospho-Diesterase (PDE) activity existed or not was examined. As a result, as shown in FIG. 3, the NPP/PDE activity was detected in the culture supernatant, in the concentrated culture supernatant, and in the purified soluble type ENPP4 (ENPP4-FLAG-His) protein.

Example 5

Purification of Soluble Type Human ENPP5 Protein and Identification of Nucleotide Pyrophosphatase/Phosphodiesterase (NPP/PDE) Activity 200 mL of the culture supernatant of the cells secreting the soluble type human ENPP5-FLAG-His protein was concentrated at 8 times by using Amicon Ultra-15 (fraction molecular weight 10,000, manufactured by Millipore Inc.). The His-Tag-added protein was affinity-purified by using AKTAexplorer 10S (manufactured by Amersham Biosciences Inc.) and His-Trap column (manufactured by Amersham Biosciences Inc.). Samples in the respective purification steps were subjected to SDS-PAGE according to a predetermined method and then the protein was stained by using Simply-Blue-Stain (manufactured by Invitrogen Inc.). As a result, as shown in FIG. 4, the bands of Human ENPP5-FLAG-His protein were detected in the eluted fractions #2-#5. The eluted fractions were dialyzed with PBS by using Slide-A-lyzer dialysis cassette (manufactured by Pierce Inc.), and thereby the soluble type human ENPP5-FLAG-His protein was obtained. 40 µL of each of the respective purification steps and purified soluble type human ENPP5-FLAG-His proteins was mixed with 50 µL of assay buffer (20 mM HEPES, 140 mM NaCl, 5 mM KCl, 1 mM $CaCl_2$, 1 mM $MgCl_2$, 10 mM Glucose, pH 9.6) and 10 µL of 10 mM pNP-TMP, and the mixture was kept at 37° C. for 2 hours and then, absorption of light of 405 nm was measured and thereby, p-nitorphenol, which was a degradation product, was measured and, whether the NPP/PDE activity existed or not was examined. As a result, as shown in FIG. 5, the NPP/PDE activity was detected in the culture supernatant, in the enriched culture supernatant, and in the purified soluble type ENPP5 (ENPP5-FLAG-His) protein. Moreover, compared to the total activity (fluid volume×increase amount of absorption of light) of the concentrated culture supernatant before purification, the total activity of the purified protein increased and therefore, it has been indicated that there is a factor inhibiting the activity of ENPP5 in the culture solution.

Example 6

Purification of Soluble Type Human ENPP6 Protein and Identification of Nucleotide Pyrophosphatase/Phosphodiesterase (NPP/PDE) Activity 400 mL of the culture supernatant of the cells secreting the soluble type human ENPP6-FLAG-His protein was concentrated at 8 times by using Amicon Ultra-15 (fraction molecular weight 10,000, manufactured by Millipore Inc.). The His-Tag-added protein was affinity-purified by using AKTAexplorer 10S (manufactured by Amersham Biosciences Inc.) and His-Trap column (manufactured by Amersham Biosciences Inc.). Samples in the respective purification steps were subjected to SDS-PAGE according to a predetermined method and then the protein was stained by using Simply-Blue-Stain (manufactured by Invitrogen Inc.). As a result, as shown in FIG. 6, the bands of Human ENPP6-FLAG-His protein were detected in the eluted fractions #2-#5. The eluted fractions were dialyzed with PBS by using Slide-A-lyzer dialysis cassette (manufactured by Pierce Inc.), and thereby the soluble type human ENPP6-FLAG-His protein was obtained. 40 µL of each of the respective purification steps and purified soluble type human ENPP6-FLAG-His proteins was mixed with 50 µL of assay buffer (20 mM HEPES, 140 mM NaCl, 5 mM KCl, 1 mM $CaCl_2$, 1 mM $MgCl_2$, 10 mM Glucose, pH 9.6) and 10 µL of 10 mM pNP-TMP, and the mixture was kept at 37° C. for 2 hours and then, absorption of light of 405 nm was measured and thereby, p-nitorphenol, which was a degradation product, was measured and, whether the NPP/PDE activity existed or not was examined. As a result, as shown in FIG. 7, the NPP/PDE activity was detected in the culture supernatant, in the concentrated culture supernatant, and in the purified soluble type ENPP6 (ENPP6-FLAG-His) protein. Moreover, as shown in Table 1, compared to the total activity (fluid volume×increase amount of absorption of light) of the enriched culture supernatant before purification, the total activity of the purified protein increased to approximately 182% and therefore, it has been indicated that there is a factor inhibiting the activity of ENPP6 in the culture solution.

TABLE 1

|  | Enriched Culture Supernatant | Purified ENPP6 |
|---|---|---|
| Solution Amount (mL) | 40 | 12 |
| PDE Activity (3 h, 10 µL Sample) | 0.116 | 0.705 |
| Total Activity | 356.7 | 650.65 |
| Total Activity Ratio (%) | 100.0 | 182.40 |

Example 7

Identification of Phospholipase C (PLC) Activity of Soluble Type ENPP5 Protein 0.2 µg of the purified soluble type ENPP5 protein was mixed in 90 µL of assay buffer (20 mM HEPES, 140 mM NaCl, 5 mM KCl, 1 mM $CaCl_2$, 1 mM $MgCl_2$, 10 mM Glucose, pH 9.6) and 10 µL of 10 mM p-nitrophenyl phosphorylcholine (pNP-PC, manufactured by Sigma Inc.), and was kept at 37° C. for 90 min and then, absorption of light of 405 nm was measured and thereby, the amount of P-nitrophenol was quantitatively determined and, whether the PLC activity existed or not was examined. As a result, as shown in FIG. 8, it has been found that the soluble type ENPP5 protein has the PLC activity.

Example 8

Identification of Phospholipase C (PLC) Activity of Soluble Type ENPP6 Protein 0.2 µg of the purified soluble type ENPP6 protein was mixed in 90 µL of assay buffer (20 mM HEPES, 140 mM NaCl, 5 mM KCl, 1 mM $CaCl_2$, 1 mM $MgCl_2$, 10 mM Glucose, pH 9.6) and 10 µL of 10 mM p-nitrophenyl phosphorylcholine (pNP-PC, manufactured by Sigma Inc.), and was kept at 37° C. for 90 min and then, absorption of light of 405 nm was measured and thereby, the amount of P-nitrophenol was quantitatively determined and, whether the PLC activity existed or not was examined. As a result, as shown in FIG. 8, it has been found that the soluble type ENPP6 protein has the PLC activity.

Example 9

Identification of Phosphodiesterase/phosphomonoesterase (PDE/PME) Activity of Soluble Type ENPP4 Protein 0.2 μg of the purified soluble type ENPP4 protein was mixed in 90 μL of assay buffer (20 mM HEPES, 140 mM NaCl, 5 mM KCl, 1 mM CaCl$_2$, 1 mM MgCl$_2$, 10 mM Glucose, pH 9.6) and 10 μL of 10 mM p-nitrophenyl phenylphosphonate (pNP-PP, manufactured by Sigma Inc.), and was kept at 37° C. for 90 min and then, absorption of light of 405 nm was measured and thereby, the amount of P-nitrophenol was quantitatively determined and, whether the PDE/PME activity existed or not was examined. As a result, as shown in FIG. 8, it has been found that the soluble type ENPP4 protein has the PDE/PME activity.

Example 10

Identification of Phosphodiesterase/phosphomonoesterase (PDE/PME) Activity of Soluble Type ENPP5 Protein 0.2 μg of the purified soluble type ENPP5 protein was mixed in 90 μL of assay buffer (20 mM HEPES, 140 mM NaCl, 5 mM KCl, 1 mM CaCl$_2$, 1 mM MgCl$_2$, 10 mM Glucose, pH 9.6) and 10 μL of 10 mM pNP-PP, and was kept at 37° C. for 90 min and then, absorption of light of 405 nm was measured and thereby, the amount of p-nitrophenol was quantitatively determined and, whether the PDE/PME activity existed or not was examined. As a result, as shown in FIG. 8, it has been found that the soluble type ENPP5 protein has the PDE/PME activity.

Example 11

Identification of Phosphodiesterase/phosphomonoesterase (PDE/PME) Activity of Soluble Type ENPP6 Protein 0.2 μg of the purified soluble type ENPP6 protein was mixed in 90 μL of assay buffer (20 mM HEPES, 140 mM NaCl, 5 mM KCl, 1 mM CaCl$_2$, 1 mM MgCl$_2$, 10 mM Glucose, pH 9.6) and 10 μL of 10 mM pNP-PP or bis-(p-nitrophenyl)phosphate (bis-pNPP), and was kept at 37° C. for 90 min and then, absorption of light of 405 nm was measured and thereby, the amount of p-nitrophenol was quantitatively determined and, whether the PDE/PME activity existed or not was examined. As a result, as shown in FIG. 8, it has been found that the soluble type ENPP6 protein has the PDE/PME activity.

As described above, the soluble type protein ENPP4 protein has the NPP/PDE activity and the PDE/PME activity, and the soluble type protein ENPP5 protein has the NPP/PDE activity, the PLC activity, and the PDE/PME activity, and the soluble type protein ENPP6 protein has the NPP/PDE activity, the PLC activity, and the PDE/PME activity.

Example 12

Investigation of Bivalent Cation Requirement of Soluble Type ENPP4 Protein 0.2 μg of the purified soluble type ENPP4 protein was mixed in 90 μL of assay buffer (20 mM HEPES, 140 mM NaCl, 5 mM KCl, 10 mM Glucose, pH 9.6), 10 μL of 10 mM pNP-PP, and (1) 1 mM final concentration of MgCl$_2$ and CaCl$_2$, (2) no additive, or (3) 1 mM final concentration of EDTA, and then was kept at 37° C. for 90 min and then, absorption of light of 405 nm was measured and thereby, the increase or decrease of the PDE/PME activity by removing bivalent cations was examined. FIG. 9 shows the ratio of the amount of p-nitrophenol in each of the samples when the ratio of the sample (1) is set to 100%. It has been found that the soluble type ENPP4 protein does not require bivalent cations.

Example 13

Investigation of Bivalent Cation Requirement of Soluble Type ENPP5 Protein 0.2 μg of the purified soluble type ENPP5 protein was mixed in 90 μL of assay buffer (20 mM HEPES, 140 mM NaCl, 5 mM KCl, 10 mM Glucose, pH 9.6), 10 μL of 10 mM pNP-PP, and (1) 1 mM final concentration of MgCl$_2$ and CaCl$_2$, (2) no additive, or (3) 1 mM final concentration of EDTA, and then was kept at 37° C. for 90 min and then, absorption of light of 405 nm was measured and thereby, the increase or decrease of the PDE/PME activity by removing bivalent cations was examined. FIG. 9 shows the ratio of the amount of p-nitrophenol in each of the samples when the ratio of the sample (1) is set to 100%. It has been thought that a certain cation except for calcium and magnesium ions is bonded to the purified soluble type ENPP5 protein because the activity decreases in the EDTA-adding sample and increases in the no-additive sample. It has been found that the soluble type ENPP5 protein requires a bivalent cation except for $Ca^{2+}$ and $Mg^{2+}$.

Example 14

Investigation of Bivalent Cation Requirement of Soluble Type ENPP6 Protein 0.2 μg of the purified soluble type ENPP6 protein was mixed in 90 μL of assay buffer (20 mM HEPES, 140 mM NaCl, 5 mM KCl, 10 mM Glucose, pH 9.6), 10 μL of 10 mM pNP-PP, and (1) 1 mM final concentration of MgCl$_2$ and CaCl$_2$, (2) no additive, or (3) 1 mM final concentration of EDTA, and then was kept at 37° C. for 90 min and then, absorption of light of 405 nm was measured and thereby, the increase or decrease of the PDE/PME activity by removing bivalent cations was examined. FIG. 9 shows the ratio of the amount of p-nitrophenol in each of the samples when the ratio of the sample (1) is set to 100%. It has been found that the soluble type ENPP6 protein requires a bivalent cation because the activity decreased in the EDTA-added sample.

Example 15

Investigation of Zinc Ion Requirement of Soluble Type ENPP6 Protein 0.2 μg of the purified soluble type ENPP6 protein was mixed in 90 μL of assay buffer (20 mM HEPES, 140 mM NaCl, 5 mM KCl, 10 mM Glucose, pH 9.6), 10 μL of 10 mM each kind of the light-emitting substrates, and (1) 1 mM final concentration of MgCl$_2$ and CaCl$_2$, (2) 1 mM final concentration of ZnCl$_2$, and then was kept at 37° C. for 90 min and then, absorption of light of 405 nm was measured and thereby, the increase or decrease of the activity by adding zinc ions was examined. As a result, as shown in FIG. 10, the activity of the soluble type ENPP6 protein was enhanced in any one of the substrates by adding zinc ions thereto.

Example 16

Search and Identification of ENPP4 Substrates and ENPP4 Inhibitory or Activating Compounds 0.2 μg of the purified soluble type ENPP4 protein was mixed in 90 μL of assay buffer (20 mM HEPES, 140 mM NaCl, 5 mM KCl, 10 mM Glucose, pH 8.5), and 10 μL of each of 10 mM pNP-TMP or pNP-PP and a solution of a test compound was added thereto, and then was kept at 37° C. for 2 hours. Then, absorption of light of 405 nm was measured and thereby, the amount of p-nitorphenol was quantitatively determined and thereby the inhibitory activity of pNP-TMP or pNP-PP degradation of each test compound was examined. By using pNP-TMP and Neurotransmitter Library Plate 10 (Purinergic & adenosines) ver. 2 (manufactured by BIOMOL Inc.), sugar nucleic acids, CDP-Choline, Diadenosine-polyphosphate, and Diguanosine-polyphosphate (manufactured by Sigma Inc.) as test compounds, the inhibitory activity of pNP-TMP or pNP-PP degradation of each of 1 mM the compound was measured and as shown in FIG. 11, 80% or more of the inhibitory activity was detected in ATP, 2-Methyl-ATP, P1P4-DiAdenosine-tetraphosphate (AP(4)A), UTP, and GTP, which have 3 phosphoric acids in the molecule. Moreover, 60% or more of the inhibitory activity was detected in CDP-Choline, and 40% or more of the inhibitory activity was detected in P1P3-DiAdenosine-triphosphate (AP(3)A), P1P6-DiAdenosine-hexaphosphate (AP(6)A). Moreover, as shown in FIG. 12, the inhibitory activity depending on concentration of ATP was detected.

Example 17

Search and Identification of ENPP5 Substrates and ENPP5 Inhibitory or Activating Compounds 0.2 μg of the purified soluble type ENPP5 protein was mixed in 90 μL of assay buffer (20 mM HEPES, 140 mM NaCl, 5 mM KCl, 10 mM Glucose, pH 7.5), and 10 μL of each of 10 mM pNP-PP and a solution of a test compound was added thereto, and then was kept at 37° C. for 2 hours. Then, absorption of light of 405 nm was measured and thereby, the amount of p-nitorphenol was quantitatively determined and thereby the inhibitory activity of pNP-PC and pNP-PP degradation of each of the test compound was examined. By using Neurotransmitter Library Plate 10 (Purinergic & adenosines) ver. 2 (manufactured by BIOMOL Inc.) as test compounds, and the inhibitory activity of pNP-TMP degradation of each of 1 mM compounds was measured and, 70% or more of the inhibitory activity was detected in 2-Methyl-ATP, and 80% or more of the inhibitory activity was detected in ADP, UDP, and GDP. Moreover, as shown in FIG. 13, the inhibitory activity of pNP-PC degradation depending on concentration of ATP was detected.

Example 18

Search and Identification of ENPP6 Substrates and ENPP6 Inhibitory or Activating Compounds 0.2 μg of the purified soluble type ENPP6 protein was mixed in 90 μL of assay buffer (20 mM HEPES, 140 mM NaCl, 5 mM KCl, 1 mM CaCl$_2$, 1 mM MgCl$_2$, 10 mM Glucose, pH 9.6), and 10 μL of each of 10 mM pNP-PP and a solution of a test compound was added thereto, and was kept at 37° C. for 2 hours. Then, absorption of light of 405 nm was measured and thereby, the amount of p-nitorphenol was quantitatively determined and thereby the inhibitory activity of pNP-TMP degradation of each of the test compounds was examined. By using Neurotransmitter Library Plate 10 (Purinergic & adenosines) ver. 2, Bioactive Lipid Library ver. 3 (manufactured by BIOMOL Inc.), and various lysophospholipids as test compounds, the inhibitory activity of pNP-PP degradation was measured and, 80% or more of the inhibitory activity was detected in Glycerophosphorilcholine, and 70% or more of the inhibitory activity in Lysophosphatidylcholine, 1-Methyladenosine, 3-Deazaadenosine, ATP, and ADP(1 mM), and 60% or more of the inhibitory activity in N6-Methyladenosine, N6-Methyl-2'-deoxy-adenosine, S-Adenosyl-L-Homocysteine, and 2-MethylthioATP. Moreover, as shown in FIG. 14, the inhibitory activity of pNP-TMP degradation depending on concentration of LPC was detected.

Example 19

Identification of Nucleic Acids to be ENPP4 Substrate 0.5 μg of the purified soluble type ENPP4 protein was mixed in 500 μL of assay buffer (20 mM HEPES, 140 mM NaCl, 5 mM KCl, 10 mM Glucose, pH 8.5), and then, each kind of nucleic acids were added thereto so that its final concentration became 200 μM. The mixture was kept at 37° C. for 2, 5, or 8 hours. Then, by using HPLC (Unison-UKC18 reversed-phase column 30×2 mm, manufactured by Imtakt Co., Ltd.) (mobile phase: 50 mM sodium phosphate buffer (pH 6.4), 5 mM tetrabutylammonium hydrogen sulfate, 1 mM EDTA, 2-30% acetonitrile), the nucleic acids were separated from the reacted solution, and the substrates and the reacted products were quantitatively determined. As a result, as shown in FIG. 15, Ap(3)A, Ap(4)A, Ap(5)A, Ap(6)A, ATP, ADP, CTP, CDP, CDP-Choline, UDP-Glucose, UTP, and UDP were degraded by ENPP4 and NMP, which was a reacted product, was detected. The degradation amount of ATP by ENPP4 was small. However, as presented in Example 16, the activity of inhibiting degradation of light-emitting substrates by ENPP4 was high. Therefore, it was indicated that ATP has an inhibitory activity against ENPP4. Moreover, the reason why the activity of degrading Ap(4)A is lower than the activity of degrading Ap(3)A is thought that ATP and AMP are generated as the degraded products of Ap(4)A and ATP inhibits the activity of ENPP4.

Example 20

Identification of Nucleic Acids to be ENPP5 Substrate 0.5 μg of the purified soluble type ENPP5 protein was mixed in 500 μL of assay buffer (20 mM HEPES, 140 mM NaCl, 5 mM KCl, 10 mM Glucose, pH 7.5), and then, each kind of nucleic acids were added thereto so that its final concentration became 200 μM. The mixture was performed at 37° C. for 2, 5, or 8 hours. Then, by using HPLC (Unison-UKC18 reversed-phase column 30×2 mm, manufactured by Imtakt Co., Ltd.) (mobile phase: 50 mM sodium phosphate buffer (pH 6.4), 5 mM tetrabutylammonium hydrogen sulfate, 1 mM EDTA, 2-30% acetonitrile), the nucleic acids were separated from the reacted solution, and the substrates and the reacted products were quantitatively determined. As a result, as shown in FIG. 15, ADP, UDP, and CDP-Choline were degraded by ENPP5, and NMP, which was a reacted product, was detected.

Example 21

Identification of Phospholipids to be ENPP4 Substrate 2.5 μg of the purified soluble type ENPP4 protein is mixed in 500 μL of assay buffer (20 mM HEPES, 140 mM NaCl, 5 mM KCl, 1 mM CaCl$_2$, 1 mM MgCl$_2$, 10 mM Glucose, pH 8.5), and then phospholipids are added thereto so that the final concentration becomes 400 μM. The mixture is kept at 37° C. for one day. Then, by using LC-MS/MS (Sepsil-C18 reversed-phase column, manufactured by Waters Inc.) (mobile phase: 0.1% ammonium formate, 46.2 to 66.7% Methanol, 23.1 to 33.3% acetonitrile, 30 to 0% water), the substrates and the reacted product are quantitatively determined from the reacted solution.

Example 22

Identification of Phospholipids to be ENPP5 Substrates 2.5 μg of the purified soluble type ENPP5 protein is mixed in 500 μL of assay buffer (20 mM HEPES, 140 mM NaCl, 5 mM KCl, 1 mM CaCl$_2$, 1 mM MgCl$_2$, 10 mM Glucose, pH 7.5), and then phospholipids are added thereto so that the final concentration becomes 400 μM. The mixture is kept at 37° C. for one day. Then, by using LC-MS/MS (Sepsil-C18 reversed-phase column, manufactured by Waters Inc.) (mobile phase: 0.1% ammonium formate, 46.2 to 66.7% Methanol, 23.1 to 33.3% acetonitrile, 30 to 0% water), the substrates and the reacted product are quantitatively determined from the reacted solution.

Example 23

Identification of Phospholipids to be ENPP6 Substrates 2.5 μg of the purified soluble type ENPP6 protein is mixed in 500 μL of assay buffer (20 mM HEPES, 140 mM NaCl, 5 mM KCl, 1 mM CaCl$_2$, 1 mM MgCl$_2$, 10 mM Glucose, pH 9.5), and then phospholipids are added thereto so that the final concentration becomes 400 μM. The mixture is kept at 37° C. for one day. Then, by extracting all of the lipids by Brigh-Dyer method and using LC-MS/MS (Sepsil-C18 reversed-phase column, manufactured by Waters Inc.) (mobile phase: 0.1% ammonium formate, 46.2 to 66.7% Methanol, 23.1 to 33.3% acetonitrile, 30 to 0% water), the substrates and the reacted product are quantitatively determined from the reacted solution.

Example 24

Investigation of Suppression Effect of ENPP4 for Proliferation of Cancer Cells

HT-29 (colon carcinoma) cells are suspended in RPMI1640 culture, and then are seeded in a 96-well titer plate so as to be 1×10$^4$ Cells/100 μL/well. 0 to 5 μU of the purified soluble type ENPP4 protein (1 U is an amount of the protein for degrading 1 μmol of pNP-PP at 30° C. for 1 min) is added thereto. After 48 hours, CellTiter 96 AQueous one solution cell proliferation (Promega Inc.) is added thereto according to its attached document. After incubation at 37° C. for one hour, 490 nm absorbance is measured and the number of the living cells is measured.

Example 25

Investigation of Suppression Effect of ENPP5 for Proliferation of Cancer Cells

HT-29 (colon carcinoma) cells are suspended in RPMI1640 culture, and then is seeded in a 96-well titer plate so as to be 1×10$^4$ Cells/100 μL/well. 0 to 5 μU of the purified soluble type ENPP5 protein (1 U is an amount of the protein for degrading 1 μmol of pNP-PP at 30° C. for 1 min) is added thereto. After 48 hours, CellTiter 96 AQueous one solution cell proliferation (Promega Inc.) is added thereto according to its attached document. After incubation at 37° C. for one hour, 490 nm absorbance is measured and the number of the living cells is measured.

Example 26

Investigation of Suppression Effect of ENPP6 for Proliferation of Cancer Cells

HT-29 (colon carcinoma) cells are suspended in RPMI1640 culture, and then are seeded in a 96-well titer plate so as to be 1×10$^4$ Cells/100 μL/well. 0 to 5 μU of the purified soluble type ENPP6 protein (1 U is an amount of the protein for degrading 1 μmol of pNP-PP at 30° C. for 1 min) is added thereto. After 48 hours, CellTiter 96 AQueous one solution cell proliferation (Promega Inc.) is added thereto according to its attached document. After performing incubation at 37° C. for one hour, 490 nm absorbance is measured and the number of the living cells is measured.

Example 27

Investigation of Effect of ENPP4 for Cancer Metastasis and Infiltration

For investigation of metastasis and infiltration, QTCTM-CollagenI assay (manufactured by Chemicon International Inc.) is used. From a culture flask, NIH3T3 cells are separated and collected, and then cleaned with a serum-free culture medium. The cells at 2.5×10$^5$ number/well and the 0 μU or 5 μU of the purified soluble type ENPP4 protein are added to an upper layer of each of Boyden chambers that are precoated with Collagen Type I and BSA (negative control) respectively. After incubating them under the condition of 5% CO$_2$ at 37° C. for 24 hours, the cells in the upper layer of the chamber are removed with a paper towel, and the cells under the membrane of the chamber are stained with a cell-stain solution. Then, the cell-stain solution is removed and an extraction buffer is added. Then, 100 μL of the cell suspension is transferred to a 96-well titer plate and 550 nm absorbance is measured.

Example 28

Investigation of Effect of ENPP5 for Cancer Metastasis and Infiltration

For investigation of metastasis and infiltration, QTCTM-CollagenI assay (manufactured by Chemicon International Inc.) is used. From a culture flask, NIH3T3 cells are separated and collected, and then cleaned with a serum-free culture medium. The cells at 2.5×10⁵ number/well and the 0 µU or 5 µU of the purified soluble type ENPP5 protein are added to an upper layer of each of Boyden chambers that are precoated with Collagen Type I and BSA (negative control) respectively. After incubating them under the condition of 5% $CO_2$ at 37° C. for 24 hours, the cells in the upper layer of the chamber are removed with a paper towel, and the cells under the membrane of the chamber are stained with a cell-stain solution. Then, the cell-stain solution is removed and an extraction buffer is added. Then, 100 µL of the cell suspension is transferred to a 96-well titer plate and 550 nm absorbance is measured.

Example 29

Investigation of Effect of ENPP6 for Cancer Metastasis and Infiltration

For investigation of metastasis and infiltration, QTCTM-CollagenI assay (manufactured by Chemicon International Inc.) is used. From a culture flask, NIH3T3 cells are separated and collected, and then cleaned with a serum-free culture medium. The cells at 2.5×10⁵ number/well and the 0 µU or 5 µU of the purified soluble type ENPP6 protein are added to an upper layer of each of Boyden chambers that are precoated with Collagen Type I and BSA (negative control) respectively. After incubating them under the condition of 5% $CO_2$ at 37° C. for 24 hours, the cells in the upper layer of the chamber are removed with a paper towel, and the cells under the membrane of the chamber are stained with a cell-stain solution. Then, the cell-stain solution is removed and an extraction buffer is added. Then, 100 µL of the cell suspension is transferred to a 96-well titer plate and 550 nm absorbance is measured.

Example 30

Expression Profile of ENPP4

In order to investigate mRNA expression of ENPP4 in human normal tissues and blood cells, ENPP4-specific primers were designed and PCR was performed by using TaKaRa Ex Taq (manufactured by TaKaRa Co., Ltd.). At this time, the primers having the following sequences were used.

```
5'-ACA TTT CCA AAC CAC TAC AG-3'  (SEQ ID NO: 16)

5'-AAC AAG CAC TTA GTA TGA CC-3'  (SEQ ID NO: 17)
```

PCR was performed by first keeping the temperature at 96° C. for 1 min and then, repeating 35 times, the temperature operations of 98° C. for 10 sec and 60° C. for 2 min, and finally keeping the temperature under 68° C. for 5 min. For analysis of expression in the human normal tissues and blood cells, Human MTC Panel I, Human MTC Panel II, Human Immune System MTC Panel, Human Blood Fractions MTC Panel (manufactured by BD Clontech Inc.) were used. The PCR products were subjected to agarose gel electrophoresis, and then the gel was stained with Ethidium bromide and a visual data was obtained by a BioDoc-It System (manufactured by UVP Inc.). The result was shown in FIG. 16. It was found that ENPP4 is expressed ubiquitously.

Example 31

Expression Profile of ENPP5

In order to investigate mRNA expression of ENPP5 in human normal tissues and blood cells, ENPP5-specific primers were designed and PCR was performed by using TaKaRa Ex Taq (manufactured by TaKaRa Co., Ltd.). At this time, the primers having the following sequences were used.

```
                                  (SEQ ID NO: 18)
5'- ACA AAA ACC TAC CCT AAC C-3'

(SEQ ID NO: 19)
5'- TAA TGC TGC CAA GAG AGA CCC C-3'
```

PCR was performed by first keeping the temperature at 96° C. for 1 min and then, repeating 35 times, the temperature operations of 98° C. for 10 sec and 54° C. for 30 min and 72° C. for 2 min, and finally keeping the temperature under 72° C. for 5 min. For analysis of expression in the human normal tissues and blood cells, Human MTC Panel I, Human MTC Panel II, Human Immune System MTC Panel, Human Blood Fractions MTC Panel (manufactured by BD Clontech Inc.) were used. The PCR products were subjected to agarose gel electrophoresis, and then the gel was stained with Ethidium bromide and a visual data was obtained by a BioDoc-It System (manufactured by UVP Inc.). The result was shown in FIG. 17. It was found that ENPP5 is expressed in CD4+ cells, CD8+ cells, CD14+ cells, immune system tissues such as lymph node and spleen.

Example 32

Expression Profile of ENPP6

In order to investigate mRNA expression of ENPP6 in human normal tissues and blood cells, ENPP6-specific primers were designed and PCR was performed by using TaKaRa Ex Taq (manufactured by TaKaRa Co., Ltd.). At this time, the primers having the following sequences were used.

```
                                  (SEQ ID NO: 20)
5'- TCA ACA AAG ACA GCC TAA TGC C-3'

(SEQ ID NO: 21)
5'- ATC CAC GCT GCC AAC CTT C-3'
```

PCR was performed by first keeping the temperature at 96° C. for 1 min and then, repeating 35 times, the temperature operations of 98° C. for 10 sec and 54° C. for 30 sec and 72° C. for 2 min, and finally keeping the temperature under 72° C. for 5 min. For analysis of expression in the human normal tissues and blood cells, Human MTC Panel I, Human MTC Panel II, Human Immune System MTC Panel, Human Blood Fractions MTC Panel (manufactured by BD Clontech Inc.) were used. The PCR products were subjected to agarose gel electrophoresis, and then the gel was stained with Ethidium bromide and a visual data was obtained by a BioDoc-It System (manufactured by UVP Inc.). The result was shown in FIG. 18. It was found that ENPP6 is highly expressed in kidney, ovary, brain, prostate, testis, lymph node and the like.

Example 33

Expression Profile of ENPP4 in Mouse Embryo

In order to investigate mRNA expression in each of mouse embryo tissues, ENPP4-specific probes (SEQ ID NO:22) were designed. The mouse section was produced by fixing a 18.5-day instar of C57BL/6 mouse embryo with a formaldehyde-based fixing solution and then embedding it with paraffin and thinly slicing it at a thickness of 6 µm. The probe was labeled with digoxigenin. The produced section was subjected to In situ Hybridization. For the antibody, anti-digoxigenin antibody labeled with alkaline phosphatase was used, and NBT/BCIP was used as the light-emitting substrate, and after staining, counterstain was performed by Kernechtrot Solution (manufactured by MUTO PURE CHEMICALS CO., LTD). As a result, it has been found that ENPP4 is expressed in cerebrum, thymus, kidney, lung, stomach, intestine, heart, liver, adrenal, pancreas, and spleen. Moreover, in lung, stomach, and intestine, the expressions were limited to bronchial epithelial cells and lumen epithelial cells, respectively. In FIG. 19, the staining photographs showing the states of mRNA expression in cerebrum, lung, stomach and intestine are shown.

Example 34

Expression Profile of ENPP5 in Mouse Embryo

In order to investigate mRNA expression in each of mouse embryo tissues, ENPP5-specific probes (SEQ ID NO:23) were designed. The mouse section was produced by fixing a 18.5-day instar of C57BL/6 mouse embryo with a formaldehyde-based fixing solution and then embedding it with paraffin and thinly slicing it at a thickness of 6 μm. The probe was labeled with digoxigenin. The produced section was subjected to In situ Hybridization. For the antibody, anti-digoxigenin antibody labeled with alkaline phosphatase was used, and NBT/BCIP was used as the light-emitting substrate, and after staining, counterstain was performed by Kernechtrot Solution (manufactured by MUTO PURE CHEMICALS CO., LTD).

Example 35

Expression Profile of ENPP6 in Mouse Embryo

In order to investigate mRNA expression in each of mouse embryo tissues, ENPP6-specific probes (SEQ ID NO:24) were designed. The mouse section was produced by fixing a 18.5-day instar of C57BL/6 mouse embryo with a formaldehyde-based fixing solution and then embedding it with paraffin and thinly slicing it at a thickness of 6 μm. The probe was labeled with digoxigenin. The produced section was subjected to In situ Hybridization. For the antibody, anti-digoxigenin antibody labeled with alkaline phosphatase was used, and NBT/BCIP was used as the light-emitting substrate, and after staining, counterstain was performed by Kernechtrot Solution (manufactured by MUTO PURE CHEMICALS CO., LTD). As a result, it has been found that the expression of ENPP6 is limited to cerebrum, adrenal, and vicinity of kidney proximal tubule. In FIG. 20, the staining photographs showing the states of mRNA expression in cerebrum, adrenal, and kidney, are shown.

INDUSTRIAL APPLICABILITY

The protein of the present invention is useful for a reagent for screening the compounds inhibiting or enhancing the activity of the protein. Moreover, the compounds of inhibiting activity or expression of the protein of the present invention, or their salts, neutralizing antibodies against the protein, the polynucleotides that are complementary to the polynucleotide coding the protein (antisense DNA, siRNA, ribozyme, and the like), and the like can be used as an agent for preventing and/or treating neurodegenerative diseases, cerebral ischemic diseases, circulatory diseases, autoimmune diseases, allergic diseases, inflammatory diseases, and the like. Moreover, the compounds of enhancing activity or expression of the protein of the present invention, or their salts, the protein or its partial peptides, the polynucleotides coding the protein, and the like can be used as an agent for preventing and/or treating circulatory diseases, cancers, and the like. Furthermore, the antibodies against the protein of the present invention and the polynucleotide of the present invention are also useful for diagnosing the above-described diseases.

---

SEQUENCE LISTING

Figure 1:
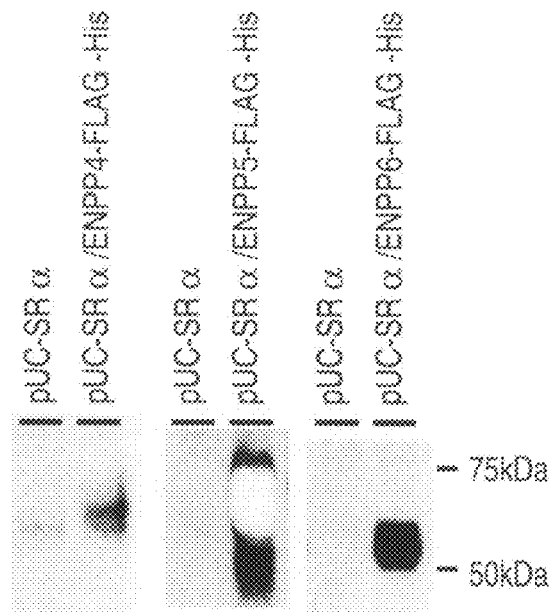
FIG. 1 is a drawing showing that a soluble type ENPP4 protein, a soluble type ENPP5 protein, and a soluble type ENPP6 protein are secreted. After introducing pUC-SRα vector, soluble type human ENPP4 protein expression vector, soluble type human ENPP5 protein expression vector, and soluble type human ENPP6 protein expression vector, culture supernatants cultured for 3 days were subjected to western blot analysis.
Figure 2:
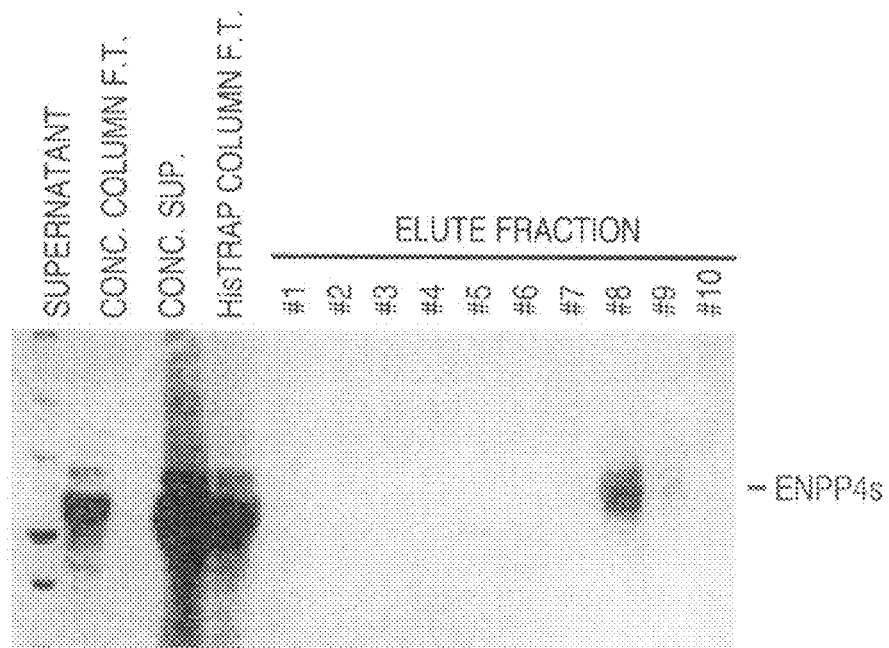
FIG. 2 is a drawing showing that a soluble type ENPP4 protein is purified along with retaining an activity. SDS-PAGE of each of the purification steps (culture supernatant, ultrafiltration column flow through, enriched culture supernatant, His trap column flow through, eluted fractions) is shown.
Figure 3:
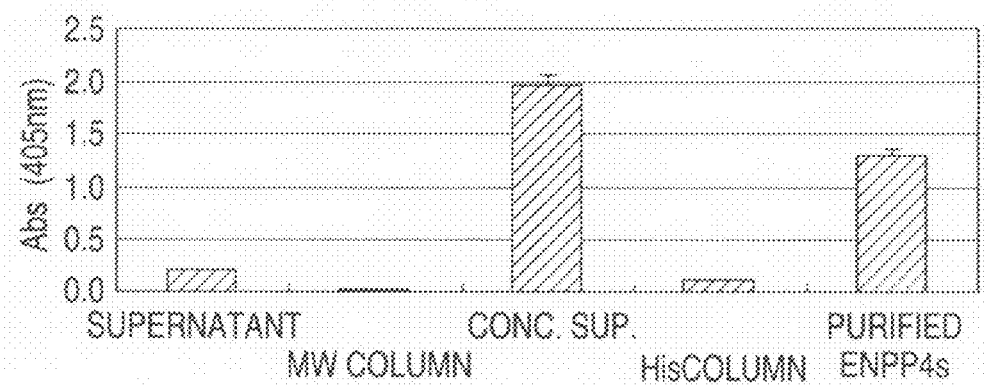
FIG. 3 is a drawing showing results of NPP/PDE activities measured in each of the purification steps of the soluble type ENPP4 protein.
Figure 4:
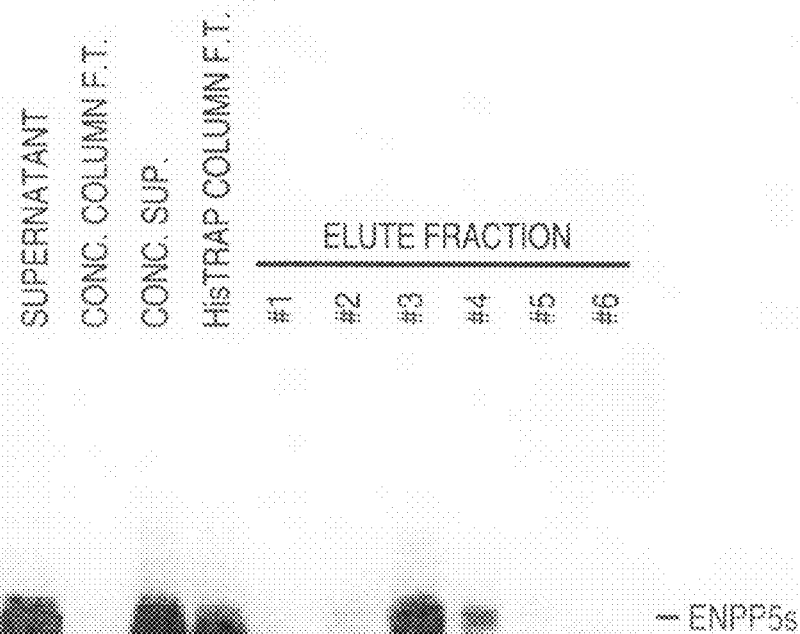
FIG. 4 is a drawing showing that a soluble type ENPP5 protein is purified along with retaining an activity. SDS-PAGE of each of the purification steps (culture supernatant, ultrafiltration column flow through, enriched culture supernatant, His trap column flow through, eluted fractions) is shown.
Figure 5:
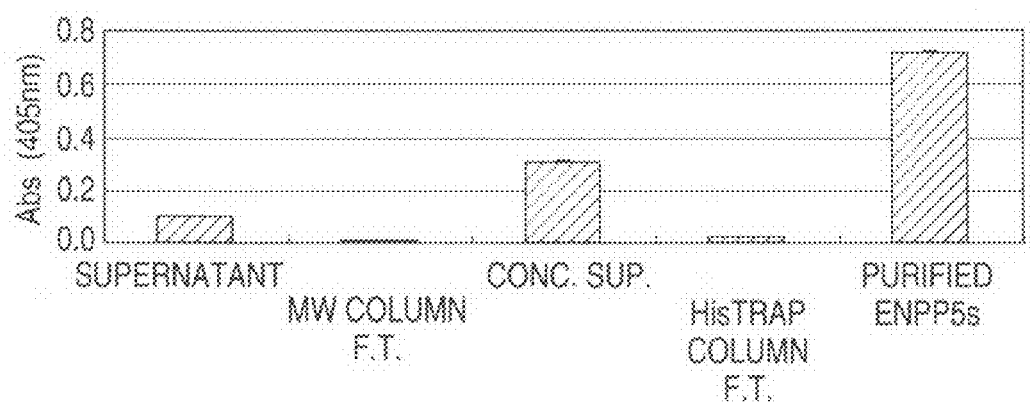
FIG. 5 is a drawing showing results of NPP/PDE activities measured in each of the purification steps of the soluble type ENPP5 protein.
Figure 6:
FIG. 6 is a drawing showing that a soluble type ENPP6 protein is purified along with retaining an activity. SDS-PAGE of each of the purification steps (culture supernatant, ultrafiltration column flow through, enriched culture supernatant, His trap column flow through, eluted fractions) is shown.
Figure 7:
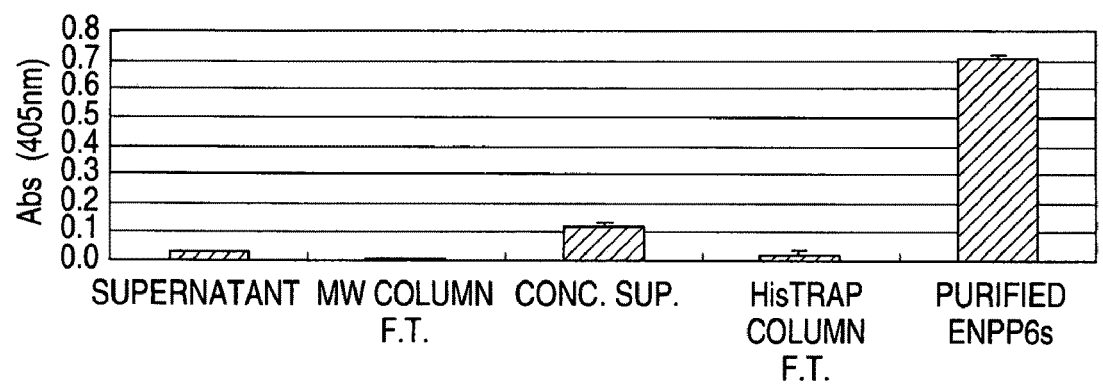
FIG. 7 is a drawing showing results of NPP/PDE activities measured in each of the purification steps of the soluble type ENPP6 protein.
Figure 8:
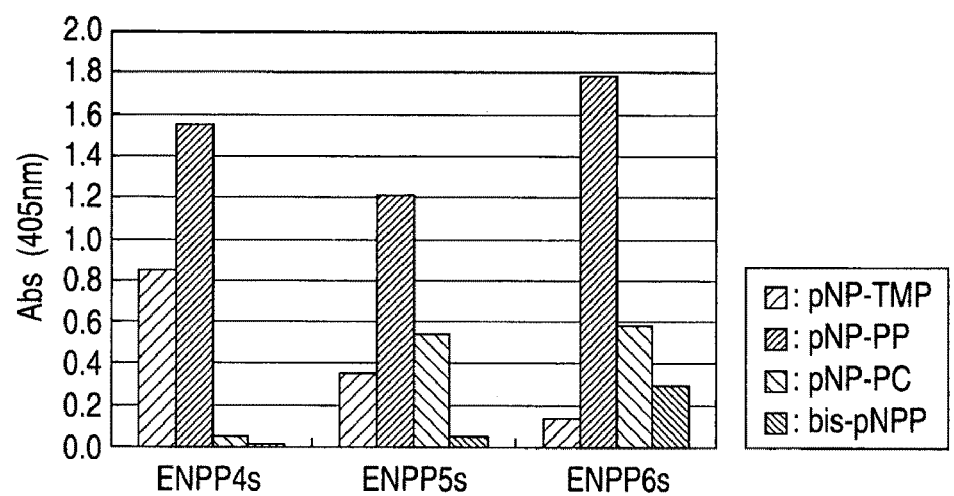
FIG. 8 is a drawing showing results of measuring activities of each of the purified soluble type ENPP proteins (ENPP4s, ENPP5s, and ENPP6s) of degrading pNP-TMP (substrate for measuring an NPP/PDE activity measurement), pNP-PP (substrate for measuring a PDE/PME activity), pNP-PC (substrate for measuring a PLC activity), bis-pNPP (substrate for measuring a PDE/PME activity). In the drawing, the results of pNP-TMP, pNP-PP, pNP-PC, bis-pNPP are shown in order from the column of the left end.
Figure 9:
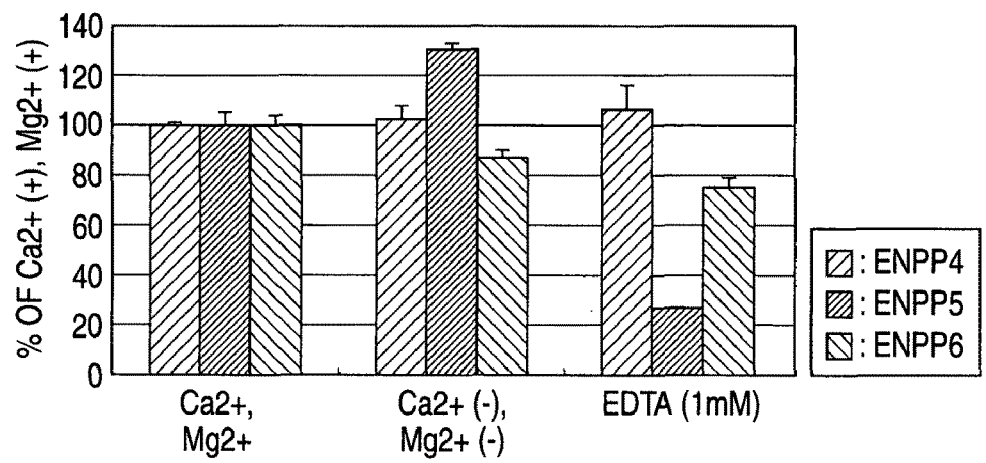
FIG. 9 is a drawing showing that ENPP4 does not require a divalent cation and that ENPP5 and ENPP6 require a divalent cation. In the drawing, the results of ENPP4, ENPP5, and ENPP6 are shown in order from the column of the left end.
Figure 10:
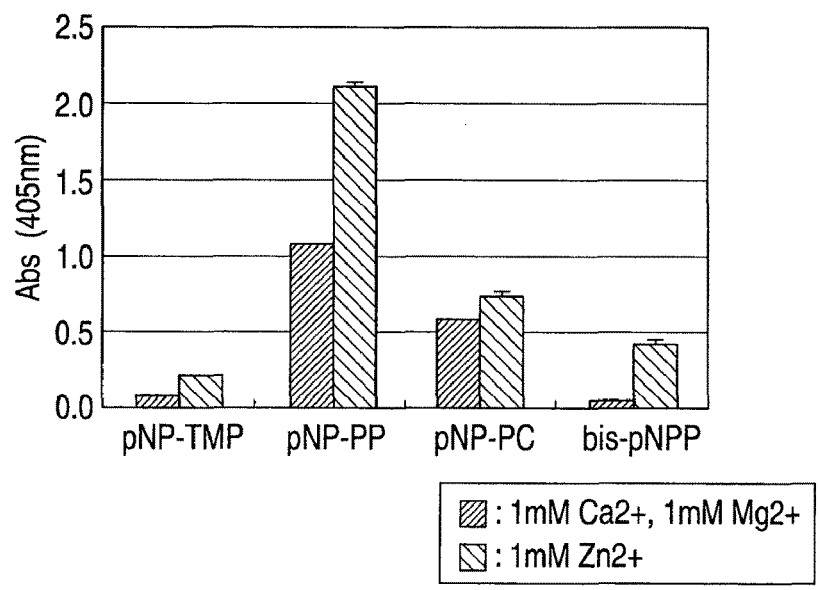
FIG. 10 is a drawing showing that the activity of ENPP6 is raised by addition of zinc. In the drawing, the respective left columns show the results of addition of magnesium ions and calcium ions, and the respective right columns show the results of addition of zinc ions.
Figure 11:
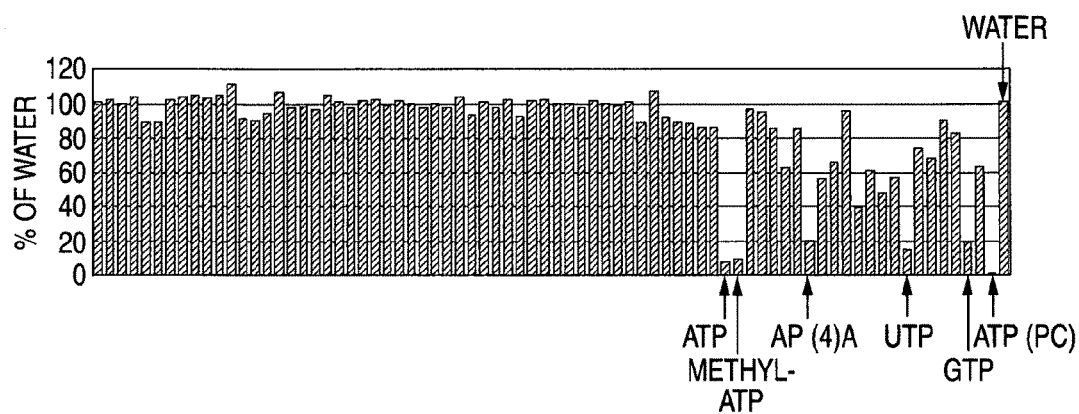
FIG. 11 is a drawing that by index of the activity of inhibiting degradation of pNP-TMP, substrates of ENPP4 and candidate compounds as inhibitory agents for ENPP4 could be identified. The longitudinal axis represents the remaining activity of coloring substrate degradation when 405 nm absorption of a sample in which water was added (right end) is set to 100%. The horizontal axis represents the respective compounds in a library. The second column from the right end shows ATP added as a positive control.
Figure 12:
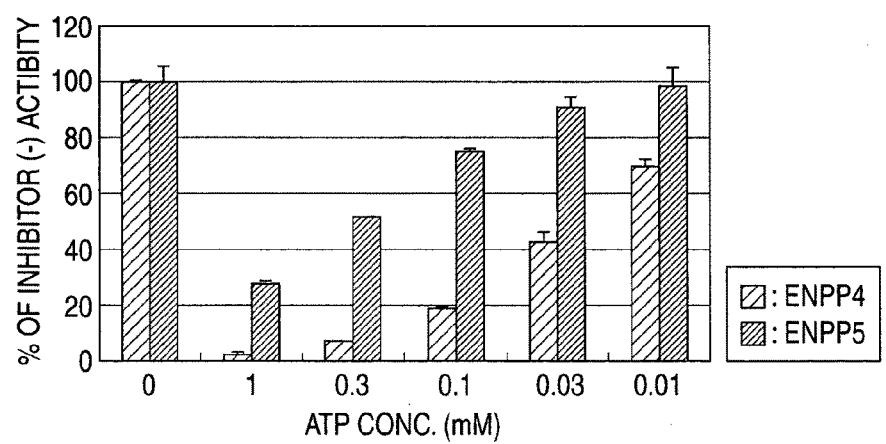
FIG. 12 is a drawing showing the inhibitory activities of pNP-TMP degradation of ENPP4 and ENPP5 by ATP. In the drawing, the respective left columns show the results of ENPP4 and the respective right columns show the results of ENPP5. The percentages of the amounts of p-nitrophenol in the respective concentrations of ATP are shown when that of the sample in which ATP is not added is set to 100%.
Figure 13:
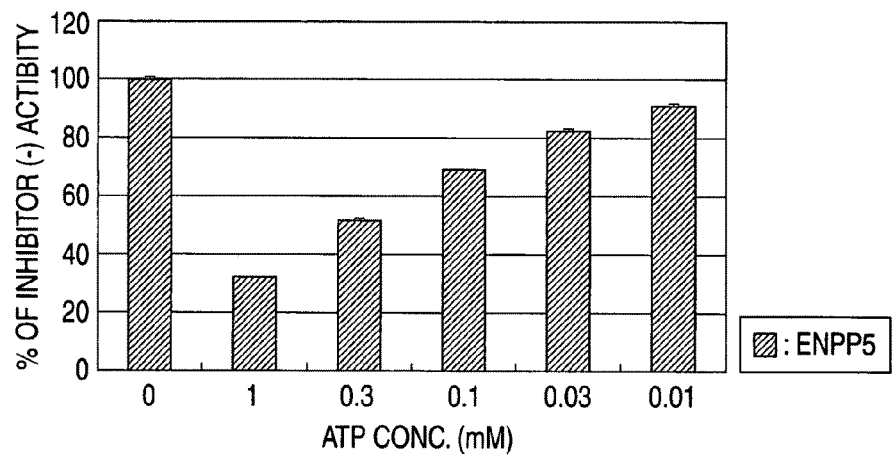
FIG. 13 is a drawing showing the inhibitory activities of pNP-PC degradation of ENPP5 by ATP. The percentages of the amounts of p-nitrophenol in the respective concentrations of ATP are shown when that of the sample in which ATP is not added is set to 100%.
Figure 14:
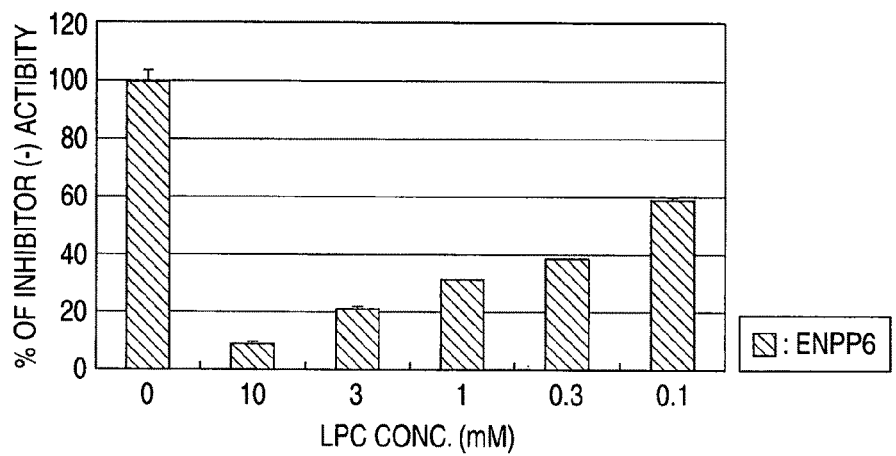
FIG. 14 is a drawing showing the inhibitory activities of pNP-TMP degradation of ENPP6 by LPC. The percentages of the amounts of p-nitrophenol in the respective concentrations of LPC are shown when that of the sample in which LPC is not added is set to 100%.
Figure 15:
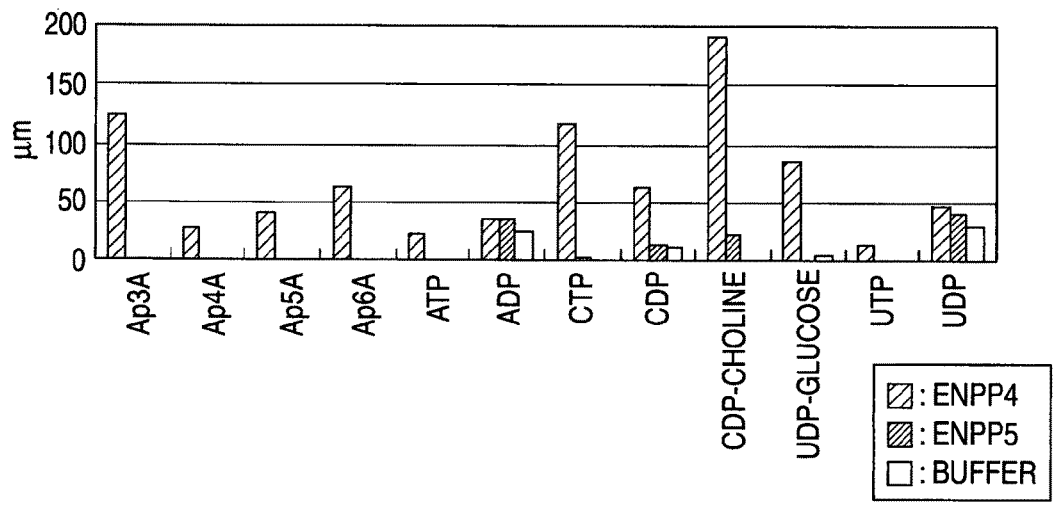
FIG. 15 is a drawing showing the degraded amounts of the various types of nucleic acids by ENPP4 and ENPP5. In the drawing, the respective results of ENPP4, ENPP5, and buffer are shown in order from the column of the left end. The amounts of degraded product generated when reacting 200 µM of each kind of the nucleic acids with ENPP4 and ENPP5, respectively for 5 hours are shown.
Figure 16:
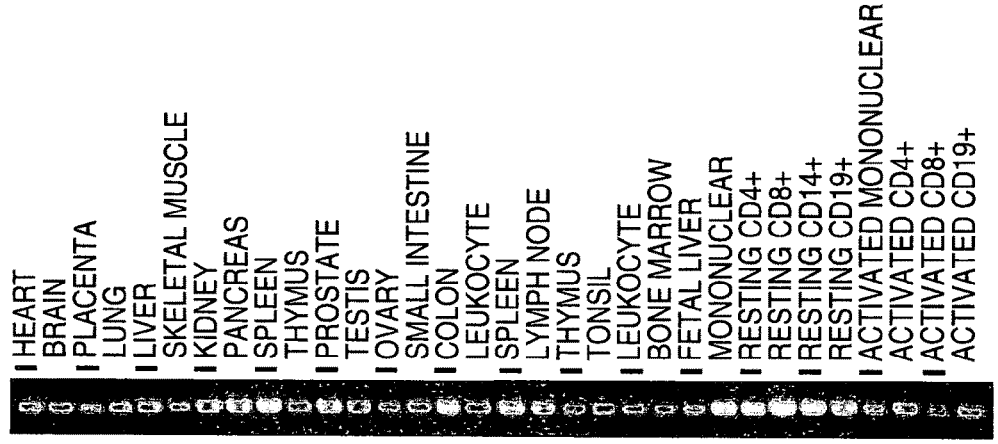
FIG. 16 is a drawing showing mRNA expressions of ENPP4.
Figure 17:
FIG. 17 is a drawing showing mRNA expressions of ENPP5.
Figure 18:
FIG. 18 is drawings showing mRNA expressions of ENPP6.
Figure 19:
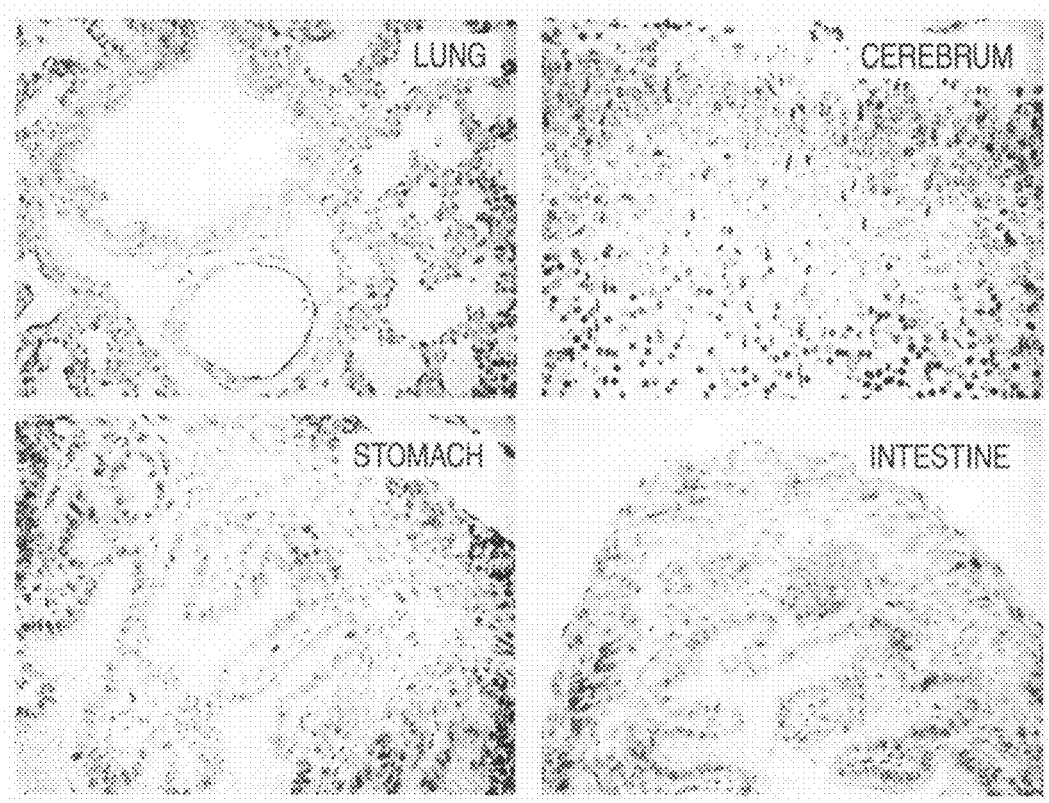
FIG. 19 is drawings showing mRNA expressions of ENPP4 in cerebrum, lung, intestine, and stomach, of mouse embryo.
Figure 20:
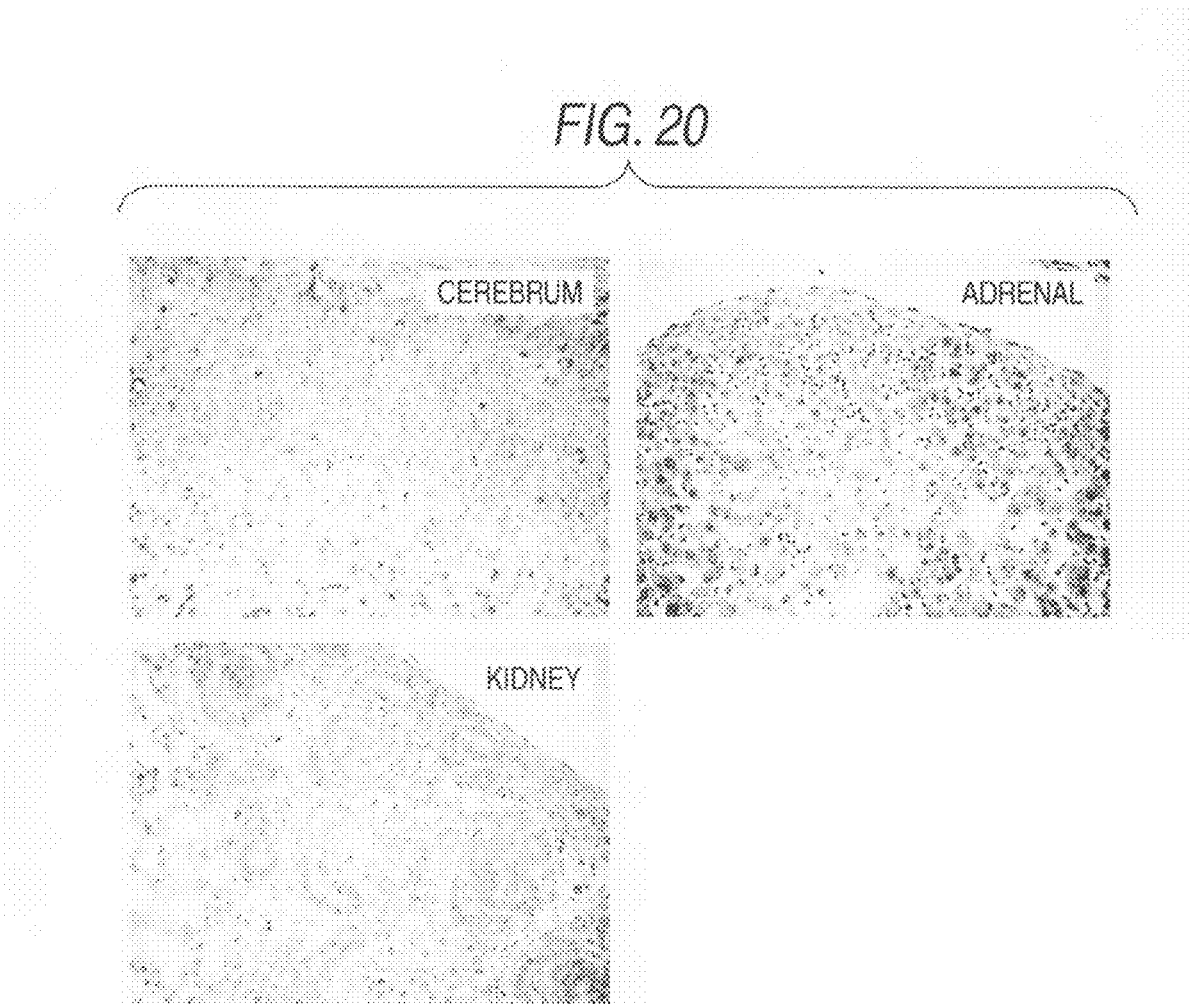
FIG. 20 is a drawing showing mRNA expressions of ENPP6 in mouse embryo.

```
<160> NUMBER OF SEQ ID NOS: 30

<210> SEQ ID NO 1
<211> LENGTH: 453
<212> TYPE: PRT
<213> ORGANISM: Homo sapiens

<400> SEQUENCE: 1

Met Lys Leu Leu Val Ile Leu Leu Phe Ser Gly Leu Ile Thr Gly Phe
1               5                   10                  15

Arg Ser Asp Ser Ser Ser Leu Pro Pro Lys Leu Leu Leu Val Ser
            20                  25                  30

Phe Asp Gly Phe Arg Ala Asp Tyr Leu Lys Asn Tyr Glu Phe Pro His
        35                  40                  45

Leu Gln Asn Phe Ile Lys Glu Gly Val Leu Val Glu His Val Lys Asn
    50                  55                  60

Val Phe Ile Thr Lys Thr Phe Pro Asn His Tyr Ser Ile Val Thr Gly
65                  70                  75                  80

Leu Tyr Glu Glu Ser His Gly Ile Val Ala Asn Ser Met Tyr Asp Ala
                85                  90                  95

Val Thr Lys Lys His Phe Ser Asp Ser Asn Asp Lys Asp Pro Phe Trp
            100                 105                 110

Trp Asn Glu Ala Val Pro Ile Trp Val Thr Asn Gln Leu Gln Glu Asn
        115                 120                 125

Arg Ser Ser Ala Ala Ala Met Trp Pro Gly Thr Asp Val Pro Ile His
    130                 135                 140

Asp Thr Ile Ser Ser Tyr Phe Met Asn Tyr Asn Ser Ser Val Ser Phe
145                 150                 155                 160

Glu Glu Arg Leu Asn Asn Ile Thr Met Trp Leu Asn Asn Ser Asn Pro
                165                 170                 175

Pro Val Thr Phe Ala Thr Leu Tyr Trp Glu Glu Pro Asp Ala Ser Gly
            180                 185                 190

His Lys Tyr Gly Pro Glu Asp Lys Glu Asn Met Ser Arg Val Leu Lys
        195                 200                 205

Lys Ile Asp Asp Leu Ile Gly Asp Leu Val Gln Arg Leu Lys Met Leu
    210                 215                 220
```

-continued

```
Gly Leu Trp Glu Asn Leu Asn Val Ile Ile Thr Ser Asp His Gly Met
225                 230                 235                 240

Thr Gln Cys Ser Gln Asp Arg Leu Ile Asn Leu Asp Ser Cys Ile Asp
            245                 250                 255

His Ser Tyr Tyr Thr Leu Ile Asp Leu Ser Pro Val Ala Ala Ile Leu
        260                 265                 270

Pro Lys Ile Asn Arg Thr Glu Val Tyr Asn Lys Leu Lys Asn Cys Ser
    275                 280                 285

Pro His Met Asn Val Tyr Leu Lys Glu Asp Ile Pro Asn Arg Phe Tyr
    290                 295                 300

Tyr Gln His Asn Asp Arg Ile Gln Pro Ile Ile Leu Val Ala Asp Glu
305                 310                 315                 320

Gly Trp Thr Ile Val Leu Asn Glu Ser Ser Gln Lys Leu Gly Asp His
                325                 330                 335

Gly Tyr Asp Asn Ser Leu Pro Ser Met His Pro Phe Leu Ala Ala His
            340                 345                 350

Gly Pro Ala Phe His Lys Gly Tyr Lys His Ser Thr Ile Asn Ile Val
        355                 360                 365

Asp Ile Tyr Pro Met Met Cys His Ile Leu Gly Leu Lys Pro His Pro
    370                 375                 380

Asn Asn Gly Thr Phe Gly His Thr Lys Cys Leu Leu Val Asp Gln Trp
385                 390                 395                 400

Cys Ile Asn Leu Pro Glu Ala Ile Ala Ile Val Ile Gly Ser Leu Leu
                405                 410                 415

Val Leu Thr Met Leu Thr Cys Leu Ile Ile Met Gln Asn Arg Leu
            420                 425                 430

Ser Val Pro Arg Pro Phe Ser Arg Leu Gln Leu Gln Glu Asp Asp Asp
        435                 440                 445

Asp Pro Leu Ile Gly
    450

<210> SEQ ID NO 2
<211> LENGTH: 477
<212> TYPE: PRT
<213> ORGANISM: Homo sapiens

<400> SEQUENCE: 2

Met Thr Ser Lys Phe Leu Leu Val Ser Phe Ile Leu Ala Ala Leu Ser
1               5                   10                  15

Leu Ser Thr Thr Phe Ser Leu Gln Pro Asp Gln Lys Val Leu Leu
            20                  25                  30

Val Ser Phe Asp Gly Phe Arg Trp Asp Tyr Leu Tyr Lys Val Pro Thr
        35                  40                  45

Pro His Phe His Tyr Ile Met Lys Tyr Gly Val His Val Lys Gln Val
    50                  55                  60

Thr Asn Val Phe Ile Thr Lys Thr Tyr Pro Asn His Tyr Thr Leu Val
65                  70                  75                  80

Thr Gly Leu Phe Ala Glu Asn His Gly Ile Val Ala Asn Asp Met Phe
                85                  90                  95

Asp Pro Ile Arg Asn Lys Ser Phe Ser Leu Asp His Met Asn Ile Tyr
            100                 105                 110

Asp Ser Lys Phe Trp Glu Glu Ala Thr Pro Ile Trp Ile Thr Asn Gln
        115                 120                 125

Arg Ala Gly His Thr Ser Gly Ala Ala Met Trp Pro Gly Thr Asp Val
    130                 135                 140
```

Lys Ile His Lys Arg Phe Pro Thr His Tyr Met Pro Tyr Asn Glu Ser
145                 150                 155                 160

Val Ser Phe Glu Asp Arg Val Ala Lys Ile Ile Glu Trp Phe Thr Ser
                165                 170                 175

Lys Glu Pro Ile Asn Leu Gly Leu Leu Tyr Trp Glu Pro Asp Asp
            180                 185                 190

Met Gly His His Leu Gly Pro Asp Ser Pro Leu Met Gly Pro Val Ile
            195                 200                 205

Ser Asp Ile Asp Lys Lys Leu Gly Tyr Leu Ile Gln Met Leu Lys Lys
        210                 215                 220

Ala Lys Leu Trp Asn Thr Leu Asn Leu Ile Ile Thr Ser Asp His Gly
225                 230                 235                 240

Met Thr Gln Cys Ser Glu Glu Arg Leu Ile Glu Leu Asp Gln Tyr Leu
                245                 250                 255

Asp Lys Asp His Tyr Thr Leu Ile Asp Gln Ser Pro Val Ala Ala Ile
                260                 265                 270

Leu Pro Lys Glu Gly Lys Phe Asp Glu Val Tyr Glu Ala Leu Thr His
            275                 280                 285

Ala His Pro Asn Leu Thr Val Tyr Lys Lys Glu Asp Val Pro Glu Arg
        290                 295                 300

Trp His Tyr Lys Tyr Asn Ser Arg Ile Gln Pro Ile Ile Ala Val Ala
305                 310                 315                 320

Asp Glu Gly Trp His Ile Leu Gln Asn Lys Ser Asp Asp Phe Leu Leu
                325                 330                 335

Gly Asn His Gly Tyr Asp Asn Ala Leu Ala Asp Met His Pro Ile Phe
            340                 345                 350

Leu Ala His Gly Pro Ala Phe Arg Lys Asn Phe Ser Lys Glu Ala Met
            355                 360                 365

Asn Ser Thr Asp Leu Tyr Pro Leu Leu Cys His Leu Leu Asn Ile Thr
        370                 375                 380

Ala Met Pro His Asn Gly Ser Phe Trp Asn Val Gln Asp Leu Leu Asn
385                 390                 395                 400

Ser Ala Met Pro Arg Val Val Pro Tyr Thr Gln Ser Thr Ile Leu Leu
                405                 410                 415

Pro Gly Ser Val Lys Pro Ala Glu Tyr Asp Gln Glu Gly Ser Tyr Pro
            420                 425                 430

Tyr Phe Ile Gly Val Ser Leu Gly Ser Ile Ile Val Ile Val Phe Phe
            435                 440                 445

Val Ile Phe Ile Lys His Leu Ile His Ser Gln Ile Pro Ala Leu Gln
        450                 455                 460

Asp Met His Ala Glu Ile Ala Gln Pro Leu Leu Gln Ala
465                 470                 475

<210> SEQ ID NO 3
<211> LENGTH: 440
<212> TYPE: PRT
<213> ORGANISM: Homo sapiens

<400> SEQUENCE: 3

Met Ala Val Lys Leu Gly Thr Leu Leu Ala Leu Ala Leu Gly Leu
1               5                   10                  15

Ala Gln Pro Ala Ser Ala Arg Arg Lys Leu Leu Val Phe Leu Leu Asp
            20                  25                  30

Gly Phe Arg Ser Asp Tyr Ile Ser Asp Glu Ala Leu Glu Ser Leu Pro
        35                  40                  45

```
Gly Phe Lys Glu Ile Val Ser Arg Gly Val Lys Val Asp Tyr Leu Thr
 50                  55                  60
Pro Asp Phe Pro Ser Leu Ser Tyr Pro Asn Tyr Tyr Thr Leu Met Thr
 65                  70                  75                  80
Gly Arg His Cys Glu Val His Gln Met Ile Gly Asn Tyr Met Trp Asp
                 85                  90                  95
Pro Thr Thr Asn Lys Ser Phe Asp Ile Gly Val Asn Lys Asp Ser Leu
            100                 105                 110
Met Pro Leu Trp Trp Asn Gly Ser Glu Pro Leu Trp Val Thr Leu Thr
        115                 120                 125
Lys Ala Lys Arg Lys Val Tyr Met Tyr Tyr Trp Pro Gly Cys Glu Val
130                 135                 140
Glu Ile Leu Gly Val Arg Pro Thr Tyr Cys Leu Glu Tyr Lys Asn Val
145                 150                 155                 160
Pro Thr Asp Ile Asn Phe Ala Asn Ala Val Ser Asp Ala Leu Asp Ser
                165                 170                 175
Phe Lys Ser Gly Arg Ala Asp Leu Ala Ala Ile Tyr His Glu Arg Ile
            180                 185                 190
Asp Val Glu Gly His His Tyr Gly Pro Ala Ser Pro Gln Arg Lys Asp
        195                 200                 205
Ala Leu Lys Ala Val Asp Thr Val Leu Lys Tyr Met Thr Lys Trp Ile
210                 215                 220
Gln Glu Arg Gly Leu Gln Asp Arg Leu Asn Val Ile Phe Ser Asp
225                 230                 235                 240
His Gly Met Thr Asp Ile Phe Trp Met Asp Lys Val Ile Glu Leu Asn
                245                 250                 255
Lys Tyr Ile Ser Leu Asn Asp Leu Gln Gln Val Lys Asp Arg Gly Pro
            260                 265                 270
Val Val Ser Leu Trp Pro Ala Pro Gly Lys His Ser Glu Ile Tyr Asn
        275                 280                 285
Lys Leu Ser Thr Val Glu His Met Thr Val Tyr Glu Lys Glu Ala Ile
290                 295                 300
Pro Ser Arg Phe Tyr Tyr Lys Lys Gly Lys Phe Val Ser Pro Leu Thr
305                 310                 315                 320
Leu Val Ala Asp Glu Gly Trp Phe Ile Thr Glu Asn Arg Glu Met Leu
                325                 330                 335
Pro Phe Trp Met Asn Ser Thr Gly Arg Arg Glu Gly Trp Gln Arg Gly
            340                 345                 350
Trp His Gly Tyr Asp Asn Glu Leu Met Asp Met Arg Gly Ile Phe Leu
        355                 360                 365
Ala Phe Gly Pro Asp Phe Lys Ser Asn Phe Arg Ala Ala Pro Ile Arg
370                 375                 380
Ser Val Asp Val Tyr Asn Val Met Cys Asn Val Val Gly Ile Thr Pro
385                 390                 395                 400
Leu Pro Asn Asn Gly Ser Trp Ser Arg Val Met Cys Met Leu Lys Gly
                405                 410                 415
Arg Ala Ser Thr Ala Pro Pro Val Trp Pro Ser His Cys Ala Leu Ala
            420                 425                 430
Leu Ile Leu Leu Phe Leu Leu Ala
        435                 440

<210> SEQ ID NO 4
<211> LENGTH: 1359
<212> TYPE: DNA
```

<213> ORGANISM: Homo sapiens

<400> SEQUENCE: 4

```
atgaagttat tagtaatact tttgttttct ggacttataa ctggttttag aagtgactct      60
tcctctagtt tgccacctaa gttactacta gtatcctttg atggcttcag agctgattat     120
ctgaagaact atgaatttcc tcatctccag aattttatca agaaggtgt tttggtagag      180
catgttaaaa atgtttttat cacaaaaaca tttccaaacc actacagtat tgtgacaggc     240
ttgtatgaag aaagccatgg cattgtggct aattccatgt atgatgcagt cacaaagaaa     300
cacttttctg actctaatga caaggatcct ttttggtgga atgaggcagt acctatttgg     360
gtgaccaatc agcttcagga aaacagatca agtgctgctg ctatgtggcc tggtactgat     420
gtacccattc acgataccat ctcttcctat tttatgaatt acaactcctc agtgtcatt    480
gaggaaagac taaataatat tactatgtgg ctaaacaatt cgaacccacc agtcaccttt    540
gcaacactat attgggaaga accagatgca agtggccaca atacggacc tgaagataaa     600
gaaaacatga gcagagtgtt gaaaaaata gatgatctta tcggtgactt agtccaaaga     660
ctcaagatgt tagggctatg gaaaatctt aatgtgatca ttacaagtga tcatgggatg    720
acccagtgtt ctcaggacag actgataaac ctggattcct gcatcgatca ttcatactac    780
actcttatag atttgagccc agttgctgca atacttccca aaataaatag aacagaggtt    840
tataacaaac tgaaaaactg tagccctcat atgaatgttt atctcaaaga agacattcct    900
aacagatttt attaccaaca taatgatcga attcagccca ttattttggt tgccgatgaa    960
ggctggacaa ttgtgctaaa tgaatcatca caaaaattag gtgaccatgg ttatgataat   1020
tctttgccta gtatgcatcc atttctagct gcccacggac ctgcatttca caaaggctac   1080
aagcatagca caattaacat tgtggatatt tatccaatga tgtgccacat cctgggatta   1140
aaaccacatc ccaataatgg gacctttggt catactaagt gcttgttagt tgaccagtgg   1200
tgcattaatc tcccagaagc catcgcgatt gttatcggtt cactcttggt gttaaccatg   1260
ctaacatgcc tcataataat catgcagaat agactttctg tacctcgtcc attttctcga   1320
cttcagctac aagaagatga tgatgatccc ttaattggg                         1359
```

<210> SEQ ID NO 5
<211> LENGTH: 1431
<212> TYPE: DNA
<213> ORGANISM: Homo sapiens

<400> SEQUENCE: 5

```
atgacttcga aatttctctt ggtgtccttc atacttgctg cactgagtct ttcaaccacc      60
ttttctctcc aaccagacca gcaaaaggtt ctactagttt cttttgatgg attccgttgg     120
gattacttat ataaagttcc aacgccccat tttcattata ttatgaaata tggtgttcac     180
gtgaagcaag ttactaatgt ttttattaca aaaacctacc ctaaccatta tactttggta     240
actggcctct ttgcagagaa tcatgggatt gttgcaaatg atatgtttga tcctattcgg     300
aacaaatctt tctccttgga tcacatgaat atttatgatt ccaagttttg ggaagaagcg     360
acaccaatat ggatcacaaa ccagagggca ggacatacta gtggtgcagc catgtggccc     420
ggaacagatg taaaaataca taagcgcttt cctactcatt acatgcctta caatgagtca     480
gtttcatttg aagatagagt tgccaaaatt attgaatggt ttacgtcaaa agagcccata    540
aatcttggtc ttctctattg ggaagaccct gatgacatgg ccaccatttt gggacctgac    600
agtccgctca tggggcctgt catttcagat attgacaaga agttaggata tctcatacaa    660
```

| | |
|---|---|
| atgctgaaaa aggcaaagtt gtggaacact ctgaacctaa tcatcacaag tgatcatgga | 720 |
| atgacgcagt gctctgagga aaggttaata gaacttgacc agtacctgga taaagaccac | 780 |
| tataccctga ttgatcaatc tccagtagca gccatcttgc aaaagaagg taaatttgat | 840 |
| gaagtctatg aagcactaac tcacgctcat cctaatctta ctgtttacaa aaagaagac | 900 |
| gttccagaaa ggtggcatta caaatacaac agtcgaattc aaccaatcat agcagtggct | 960 |
| gatgaagggt ggcacatttt acagaataag tcagatgact ttctgttagg caaccacggt | 1020 |
| tacgataatg cgttagcaga tatgcatcca atattttag cccatggtcc tgccttcaga | 1080 |
| aagaatttct caaaagaagc catgaactcc acagatttgt acccactact atgccacctc | 1140 |
| ctcaatatca ccgccatgcc acacaatgga tcattctgga atgtccagga tctgctcaat | 1200 |
| tcagcaatgc caagggtggt cccttataca cagagtacta tactcctccc tggtagtgtt | 1260 |
| aaaccagcag aatatgacca agaggggtca taccttatt tcataggggt ctctcttggc | 1320 |
| agcattatag tgattgtatt ttttgtaatt ttcattaagc atttaattca cagtcaaata | 1380 |
| cctgccttac aagatatgca tgctgaaata gctcaaccat tattacaagc c | 1431 |

```
<210> SEQ ID NO 6
<211> LENGTH: 1320
<212> TYPE: DNA
<213> ORGANISM: Homo sapiens

<400> SEQUENCE: 6
```

| | |
|---|---|
| atggcagtga agcttgggac cctcctgctg gcccttgccc tgggcctggc ccagccagcc | 60 |
| tctgcccgcc ggaagctgct ggtgtttctg ctggatggtt ttcgctcaga ctacatcagt | 120 |
| gatgaggcgc tggagtcatt gcctggtttc aaagagattg tgagcagggg agtaaaagtg | 180 |
| gattacttga ctccagactt ccctagtctc tcgtatccca attattatac cctaatgact | 240 |
| ggccgccatt gtgaagtcca tcagatgatc gggaactaca tgtgggaccc caccaccaac | 300 |
| aagtcctttg acattggcgt caacaaagac agcctaatgc ctctctggtg gaatggatca | 360 |
| gaacctctgt gggtcactct gaccaaggcc aaaaggaagg tctacatgta ctactgccca | 420 |
| ggctgtgagg ttgagattct gggtgtcaga cccaccttact gcctagaata taaaaatgtc | 480 |
| ccaacggata tcaattttgc caatgcagtc agcgatgctc ttgactcctt caagagtggc | 540 |
| cgggccgacc tggcagccat ataccatgag cgcattgacg tggaaggcca ccactacggg | 600 |
| cctgcatctc gcagaggaa agatgccctc aaggctgtag acactgtcct gaagtacatg | 660 |
| accaagtgga tccaggagcg gggcctgcag gaccgcctga cgtcattat tttctcggat | 720 |
| cacggaatga ccgacatttt ctggatggac aaagtgattg agctgaataa gtacatcagc | 780 |
| ctgaatgacc tgcagcaagt gaaggaccgc ggggcctgttg tgagcctttg gccggccct | 840 |
| gggaaacact ctgagatata aacaaactg agcacagtgg aacacatgac tgtctacgag | 900 |
| aaagaagcca tccaagcag gttctattac aagaaaggaa agtttgtctc tcctttgact | 960 |
| ttagtggctg atgaaggctg gttcataact gagaatcgag agatgcttcc gttttggatg | 1020 |
| aacagcaccg gcaggcggga aggttggcag cgtggatggc acggctacga caacgagctc | 1080 |
| atggacatgc ggggcatctt cctggccttc ggacctgatt tcaaatccaa cttcagagct | 1140 |
| gctcctatca ggtcggtgga cgtctacaat gtcatgtgca atgtggtggg catcaccccg | 1200 |
| ctgcccaaca acggatcctg gtccagggtg atgtgcatgc tgaagggccg cgccagcact | 1260 |
| gccccgcctg tctggcccag ccactgtgcc ctggcactga ttcttctctt cctgcttgca | 1320 |

```
<210> SEQ ID NO 7
```

```
<211> LENGTH: 389
<212> TYPE: PRT
<213> ORGANISM: Homo sapiens

<400> SEQUENCE: 7

Phe Arg Ser Asp Ser Ser Ser Leu Pro Pro Lys Leu Leu Leu Val
1               5                   10                  15

Ser Phe Asp Gly Phe Arg Ala Asp Tyr Leu Lys Asn Tyr Glu Phe Pro
                20                  25                  30

His Leu Gln Asn Phe Ile Lys Glu Gly Val Leu Val Glu His Val Lys
            35                  40                  45

Asn Val Phe Ile Thr Lys Thr Phe Pro Asn His Tyr Ser Ile Val Thr
50                  55                  60

Gly Leu Tyr Glu Glu Ser His Gly Ile Val Ala Asn Ser Met Tyr Asp
65                  70                  75                  80

Ala Val Thr Lys Lys His Phe Ser Asp Ser Asn Asp Lys Asp Pro Phe
                85                  90                  95

Trp Trp Asn Glu Ala Val Pro Ile Trp Val Thr Asn Gln Leu Gln Glu
            100                 105                 110

Asn Arg Ser Ser Ala Ala Ala Met Trp Pro Gly Thr Asp Val Pro Ile
        115                 120                 125

His Asp Thr Ile Ser Ser Tyr Phe Met Asn Tyr Asn Ser Ser Val Ser
130                 135                 140

Phe Glu Glu Arg Leu Asn Asn Ile Thr Met Trp Leu Asn Asn Ser Asn
145                 150                 155                 160

Pro Pro Val Thr Phe Ala Thr Leu Tyr Trp Glu Glu Pro Asp Ala Ser
                165                 170                 175

Gly His Lys Tyr Gly Pro Glu Asp Lys Glu Asn Met Ser Arg Val Leu
            180                 185                 190

Lys Lys Ile Asp Asp Leu Ile Gly Asp Leu Val Gln Arg Leu Lys Met
        195                 200                 205

Leu Gly Leu Trp Glu Asn Leu Asn Val Ile Ile Thr Ser Asp His Gly
210                 215                 220

Met Thr Gln Cys Ser Gln Asp Arg Leu Ile Asn Leu Asp Ser Cys Ile
225                 230                 235                 240

Asp His Ser Tyr Tyr Thr Leu Ile Asp Leu Ser Pro Val Ala Ala Ile
                245                 250                 255

Leu Pro Lys Ile Asn Arg Thr Glu Val Tyr Asn Lys Leu Lys Asn Cys
            260                 265                 270

Ser Pro His Met Asn Val Tyr Leu Lys Glu Asp Ile Pro Asn Arg Phe
        275                 280                 285

Tyr Tyr Gln His Asn Asp Arg Ile Gln Pro Ile Ile Leu Val Ala Asp
290                 295                 300

Glu Gly Trp Thr Ile Val Leu Asn Glu Ser Ser Gln Lys Leu Gly Asp
305                 310                 315                 320

His Gly Tyr Asp Asn Ser Leu Pro Ser Met His Pro Phe Leu Ala Ala
                325                 330                 335

His Gly Pro Ala Phe His Lys Gly Tyr Lys His Ser Thr Ile Asn Ile
            340                 345                 350

Val Asp Ile Tyr Pro Met Met Cys His Ile Leu Gly Leu Lys Pro His
        355                 360                 365

Pro Asn Asn Gly Thr Phe Gly His Thr Lys Cys Leu Leu Val Asp Gln
370                 375                 380

Trp Cys Ile Asn Leu
385
```

<210> SEQ ID NO 8
<211> LENGTH: 407
<212> TYPE: PRT
<213> ORGANISM: Homo sapiens

<400> SEQUENCE: 8

Leu Gln Pro Asp Gln Gln Lys Val Leu Leu Val Ser Phe Asp Gly Phe
1               5                   10                  15

Arg Trp Asp Tyr Leu Tyr Lys Val Pro Thr Pro His Phe His Tyr Ile
            20                  25                  30

Met Lys Tyr Gly Val His Val Lys Gln Val Thr Asn Val Phe Ile Thr
        35                  40                  45

Lys Thr Tyr Pro Asn His Tyr Thr Leu Val Thr Gly Leu Phe Ala Glu
    50                  55                  60

Asn His Gly Ile Val Ala Asn Asp Met Phe Asp Pro Ile Arg Asn Lys
65                  70                  75                  80

Ser Phe Ser Leu Asp His Met Asn Ile Tyr Asp Ser Lys Phe Trp Glu
                85                  90                  95

Glu Ala Thr Pro Ile Trp Ile Thr Asn Gln Arg Ala Gly His Thr Ser
            100                 105                 110

Gly Ala Ala Met Trp Pro Gly Thr Asp Val Lys Ile His Lys Arg Phe
        115                 120                 125

Pro Thr His Tyr Met Pro Tyr Asn Glu Ser Val Ser Phe Glu Asp Arg
    130                 135                 140

Val Ala Lys Ile Ile Glu Trp Phe Thr Ser Lys Glu Pro Ile Asn Leu
145                 150                 155                 160

Gly Leu Leu Tyr Trp Glu Asp Pro Asp Met Gly His His Leu Gly
                165                 170                 175

Pro Asp Ser Pro Leu Met Gly Pro Val Ile Ser Asp Ile Asp Lys Lys
            180                 185                 190

Leu Gly Tyr Leu Ile Gln Met Leu Lys Lys Ala Lys Leu Trp Asn Thr
        195                 200                 205

Leu Asn Leu Ile Ile Thr Ser Asp His Gly Met Thr Gln Cys Ser Glu
    210                 215                 220

Glu Arg Leu Ile Glu Leu Asp Gln Tyr Leu Asp Lys Asp His Tyr Thr
225                 230                 235                 240

Leu Ile Asp Gln Ser Pro Val Ala Ala Ile Leu Pro Lys Glu Gly Lys
                245                 250                 255

Phe Asp Glu Val Tyr Glu Ala Leu Thr His Ala His Pro Asn Leu Thr
            260                 265                 270

Val Tyr Lys Lys Glu Asp Val Pro Glu Arg Trp His Tyr Lys Tyr Asn
        275                 280                 285

Ser Arg Ile Gln Pro Ile Ile Ala Val Ala Asp Glu Gly Trp His Ile
    290                 295                 300

Leu Gln Asn Lys Ser Asp Asp Phe Leu Leu Gly Asn His Gly Tyr Asp
305                 310                 315                 320

Asn Ala Leu Ala Asp Met His Pro Ile Phe Leu Ala His Gly Pro Ala
                325                 330                 335

Phe Arg Lys Asn Phe Ser Lys Glu Ala Met Asn Ser Thr Asp Leu Tyr
            340                 345                 350

Pro Leu Leu Cys His Leu Leu Asn Ile Thr Ala Met Pro His Asn Gly
        355                 360                 365

Ser Phe Trp Asn Val Gln Asp Leu Leu Asn Ser Ala Met Pro Arg Val
    370                 375                 380

Val Pro Tyr Thr Gln Ser Thr Ile Leu Leu Pro Gly Ser Val Lys Pro
385                 390                 395                 400

Ala Glu Tyr Asp Gln Glu Gly
                405

<210> SEQ ID NO 9
<211> LENGTH: 401
<212> TYPE: PRT
<213> ORGANISM: Homo sapiens

<400> SEQUENCE: 9

Arg Arg Lys Leu Leu Val Phe Leu Leu Asp Gly Phe Arg Ser Asp Tyr
1               5                   10                  15

Ile Ser Asp Glu Ala Leu Glu Ser Leu Pro Gly Phe Lys Glu Ile Val
                20                  25                  30

Ser Arg Gly Val Lys Val Asp Tyr Leu Thr Pro Asp Phe Pro Ser Leu
            35                  40                  45

Ser Tyr Pro Asn Tyr Tyr Thr Leu Met Thr Gly Arg His Cys Glu Val
        50                  55                  60

His Gln Met Ile Gly Asn Tyr Met Trp Asp Pro Thr Thr Asn Lys Ser
65                  70                  75                  80

Phe Asp Ile Gly Val Asn Lys Asp Ser Leu Met Pro Leu Trp Trp Asn
                85                  90                  95

Gly Ser Glu Pro Leu Trp Val Thr Leu Thr Lys Ala Lys Arg Lys Val
                100                 105                 110

Tyr Met Tyr Tyr Trp Pro Gly Cys Glu Val Glu Ile Leu Gly Val Arg
            115                 120                 125

Pro Thr Tyr Cys Leu Glu Tyr Lys Asn Val Pro Thr Asp Ile Asn Phe
130                 135                 140

Ala Asn Ala Val Ser Asp Ala Leu Asp Ser Phe Lys Ser Gly Arg Ala
145                 150                 155                 160

Asp Leu Ala Ala Ile Tyr His Glu Arg Ile Asp Val Glu Gly His His
                165                 170                 175

Tyr Gly Pro Ala Ser Pro Gln Arg Lys Asp Ala Leu Lys Ala Val Asp
            180                 185                 190

Thr Val Leu Lys Tyr Met Thr Lys Trp Ile Gln Glu Arg Gly Leu Gln
        195                 200                 205

Asp Arg Leu Asn Val Ile Ile Phe Ser Asp His Gly Met Thr Asp Ile
210                 215                 220

Phe Trp Met Asp Lys Val Ile Glu Leu Asn Lys Tyr Ile Ser Leu Asn
225                 230                 235                 240

Asp Leu Gln Gln Val Lys Asp Arg Gly Pro Val Val Ser Leu Trp Pro
                245                 250                 255

Ala Pro Gly Lys His Ser Glu Ile Tyr Asn Lys Leu Ser Thr Val Glu
            260                 265                 270

His Met Thr Val Tyr Glu Lys Glu Ala Ile Pro Ser Arg Phe Tyr Tyr
        275                 280                 285

Lys Lys Gly Lys Phe Val Ser Pro Leu Thr Leu Val Ala Asp Glu Gly
290                 295                 300

Trp Phe Ile Thr Glu Asn Arg Glu Met Leu Pro Phe Trp Met Asn Ser
305                 310                 315                 320

Thr Gly Arg Arg Glu Gly Trp Gln Arg Gly Trp His Gly Tyr Asp Asn
                325                 330                 335

Glu Leu Met Asp Met Arg Gly Ile Phe Leu Ala Phe Gly Pro Asp Phe
            340                 345                 350

```
Lys Ser Asn Phe Arg Ala Ala Pro Ile Arg Ser Val Asp Val Tyr Asn
        355                 360                 365

Val Met Cys Asn Val Val Gly Ile Thr Pro Leu Pro Asn Asn Gly Ser
    370                 375                 380

Trp Ser Arg Val Met Cys Met Leu Lys Gly Arg Ala Ser Thr Ala Pro
385                 390                 395                 400

Pro

<210> SEQ ID NO 10
<211> LENGTH: 1167
<212> TYPE: DNA
<213> ORGANISM: Homo sapiens

<400> SEQUENCE: 10
tttagaagtg actcttcctc tagtttgcca cctaagttac tactagtatc ctttgatggc      60
ttcagagctg attatctgaa gaactatgaa tttcctcatc tccagaattt tatcaaagaa     120
ggtgttttgg tagagcatgt taaaaatgtt tttatcacaa aacatttcc aaaccactac      180 agtattgtga caggcttgta tgaagaaagc catggcattg tggctaattc catgtatgat     240
gcagtcacaa agaaacactt ttctgactct aatgacaagg atcctttttg gtggaatgag     300
gcagtaccta tttgggtgac caatcagctt caggaaaaca gatcaagtgc tgctgctatg     360
tggcctggta ctgatgtacc cattcacgat accatctctt cctatttat gaattacaac      420 tcctcagtgt catttgagga aagactaaat aatattacta tgtggctaaa caattcgaac     480
ccaccagtca cctttgcaac actatattgg gaagaaccag atgcaagtgg ccacaaatac     540
ggacctgaag ataaagaaaa catgagcaga gtgttgaaaa aatagatga tcttatcggt      600 gacttagtcc aaagactcaa gatgttaggg ctatgggaaa atcttaatgt gatcattaca     660
agtgatcatg ggatgaccca gtgttctcag gacagactga taaacctgga ttcctgcatc     720
gatcattcat actacactct tatagatttg agcccagttg ctgcaatact cccaaaata      780 aatagaacag aggtttataa caaactgaaa aactgtagcc tcatatgaa tgtttatctc     840 aaagaagaca ttcctaacag atttttattac caacataatg atcgaattca gcccattatt     900
ttggttgccg atgaaggctg acaattgtg ctaaatgaat catcacaaaa attaggtgac      960
catggttatg ataattcttt gcctagtatg catccatttc tagctgccca cggacctgca    1020
tttcacaaag gctacaagca tagcacaatt aacattgtgg atatttatcc aatgatgtgc    1080
cacatcctgg gattaaaacc acatcccaat aatgggacct ttggtcatac taagtgcttg    1140
ttagttgacc agtggtgcat taatctc                                        1167

<210> SEQ ID NO 11
<211> LENGTH: 1221
<212> TYPE: DNA
<213> ORGANISM: Homo sapiens

<400> SEQUENCE: 11
ctccaaccag accagcaaaa ggttctacta gtttcttttg atggattccg ttgggattac      60
ttatataaag ttccaacgcc ccatttcat tatattatga aatatggtgt tcacgtgaag      120
caagttacta atgttttat tacaaaaacc taccctaacc attatacttt ggtaactggc     180
ctctttgcag agaatcatgg gattgttgca atgatatgt ttgatcctat tcggaacaaa      240
tctttctcct tggatcacat gaatatttat gattccaagt tttgggaaga agcgacacca     300
atatggatca caaccagag ggcaggacat actagtggtg cagccatgtg gcccggaaca      360
```

-continued

| | |
|---|---|
| gatgtaaaaa tacataagcg ctttcctact cattacatgc cttacaatga gtcagtttca | 420 |
| tttgaagata gagttgccaa aattattgaa tggtttacgt caaaagagcc cataaatctt | 480 |
| ggtcttctct attgggaaga ccctgatgac atgggccacc atttgggacc tgacagtccg | 540 |
| ctcatggggc ctgtcatttc agatattgac aagaagttag gatatctcat acaaatgctg | 600 |
| aaaaaggcaa agttgtggaa cactctgaac ctaatcatca caagtgatca tggaatgacg | 660 |
| cagtgctctg aggaaaggtt aatagaactt gaccagtacc tggataaaga ccactatacc | 720 |
| ctgattgatc aatctccagt agcagccatc ttgccaaaag aaggtaaatt tgatgaagtc | 780 |
| tatgaagcac taactcacgc tcatcctaat cttactgttt acaaaaaaga agacgttcca | 840 |
| gaaaggtggc attacaaata caacagtcga attcaaccaa tcatagcagt ggctgatgaa | 900 |
| gggtggcaca ttttacagaa taagtcagat gactttctgt taggcaacca cggttacgat | 960 |
| aatgcgttag cagatatgca tccaatattt ttagcccatg gtcctgcctt cagaaagaat | 1020 |
| ttctcaaaag aagccatgaa ctccacagat ttgtacccac tactatgcca cctcctcaat | 1080 |
| atcaccgcca tgccacacaa tggatcattc tggaatgtcc aggatctgct caattcagca | 1140 |
| atgccaaggg tggtccctta tacacagagt actatactcc tccctggtag tgttaaacca | 1200 |
| gcagaatatg accaagaggg g | 1221 |

<210> SEQ ID NO 12
<211> LENGTH: 1203
<212> TYPE: DNA
<213> ORGANISM: Homo sapiens

<400> SEQUENCE: 12

| | |
|---|---|
| cgccggaagc tgctggtgtt tctgctggat ggttttcgct cagactacat cagtgatgag | 60 |
| gcgctggagt cattgcctgg tttcaaagag attgtgagca ggggagtaaa agtggattac | 120 |
| ttgactccag acttccctag tctctcgtat cccaattatt ataccctaat gactggccgc | 180 |
| cattgtgaag tccatcagat gatcgggaac tacatgtggg accccaccac caacaagtcc | 240 |
| tttgacattg cgtcaacaa agacagccta atgcctctct ggtggaatgg atcagaacct | 300 |
| ctgtgggtca ctctgaccaa ggccaaaagg aaggtctaca tgtactactg ccaggctgt | 360 |
| gaggttgaga ttctgggtgt cagacccacc tactgcctag aatataaaaa tgtcccaacg | 420 |
| gatatcaatt ttgccaatgc agtcagcgat gctcttgact ccttcaagag tggccgggcc | 480 |
| gacctggcag ccatatacca tgagcgcatt gacgtggaag ccaccactca cgggcctgca | 540 |
| tctccgcaga ggaaagatgc cctcaaggct gtagacactg tcctgaagta catgaccaag | 600 |
| tggatccagg agcggggcct gcaggaccgc ctgaacgtca ttattttctc ggatcacgga | 660 |
| atgaccgaca ttttctggat ggacaaagtg attgagctga ataagtacat cagcctgaat | 720 |
| gacctgcagc aagtgaagga ccgcgggcct gttgtgagcc tttggccggc ccctgggaaa | 780 |
| cactctgaga tatataacaa actgagcaca gtggaacaca tgactgtcta cgagaaagaa | 840 |
| gccatcccaa gcaggttcta ttacaagaaa ggaaagtttg tctctccttt gactttagtg | 900 |
| gctgatgaag gctggttcat aactgagaat cgagagatgc ttccgttttg gatgaacagc | 960 |
| accggcaggc gggaaggttg gcagcgtgga tggcacggct acgacaacga gctcatggac | 1020 |
| atgcggggca tcttcctggc cttcggacct gatttcaaat ccaacttcag agctgctcct | 1080 |
| atcaggtcgg tggacgtcta caatgtcatg tgcaatgtgg tgggcatcac cccgctgccc | 1140 |
| aacaacggat cctggtccag ggtgatgtgc atgctgaagg ccgcgccag cactgccccg | 1200 |
| cct | 1203 |

<210> SEQ ID NO 13
<211> LENGTH: 1254
<212> TYPE: DNA
<213> ORGANISM: Artificial
<220> FEATURE:
<223> OTHER INFORMATION: Synthetic construct (DNA encoding tagged protein)

<400> SEQUENCE: 13

| | | | | | |
|---|---|---|---|---|---|
| atgaagttat | tagtaatact | tttgttttct | ggacttataa | ctggttttag | aagtgactct | 60 |
| tcctctagtt | tgccacctaa | gttactacta | gtatcctttg | atggcttcag | agctgattat | 120 |
| ctgaagaact | atgaatttcc | tcatctccag | aattttatca | agaaggtgt | tttggtagag | 180 |
| catgttaaaa | atgtttttat | cacaaaaaca | tttccaaacc | actacagtat | tgtgacaggc | 240 |
| ttgtatgaag | aaagccatgg | cattgtggct | aattccatgt | atgatgcagt | cacaaagaaa | 300 |
| cactttctg | actctaatga | caaggatcct | ttttggtgga | atgaggcagt | acctatttgg | 360 |
| gtgaccaatc | agcttcagga | aaacagatca | agtgctgctg | ctatgtggcc | tggtactgat | 420 |
| gtacccattc | acgataccat | ctcttcctat | tttatgaatt | acaactcctc | agtgtcatt | 480 |
| gaggaaagac | taaataatat | tactatgtgg | ctaaacaatt | cgaacccacc | agtcaccttt | 540 |
| gcaacactat | attgggaaga | accagatgca | agtggccaca | atacggacc | tgaagataaa | 600 |
| gaaaacatga | gcagagtgtt | gaaaaaaata | gatgatctta | tcggtgactt | agtccaaaga | 660 |
| ctcaagatgt | tagggctatg | ggaaaatctt | aatgtgatca | ttacaagtga | tcatgggatg | 720 |
| acccagtgtt | ctcaggacag | actgataaac | ctggattcct | gcatcgatca | ttcatactac | 780 |
| actcttatag | atttgagccc | agttgctgca | atacttccca | aaataaatag | aacagaggtt | 840 |
| tataacaaac | tgaaaaactg | tagccctcat | atgaatgttt | atctcaaaga | agacattcct | 900 |
| aacagatttt | attaccaaca | taatgatcga | attcagccca | ttattttggt | tgccgatgaa | 960 |
| ggctggacaa | ttgtgctaaa | tgaatcatca | caaaaattag | gtgaccatgg | ttatgataat | 1020 |
| tctttgccta | gtatgcatcc | atttctagct | gcccacggac | ctgcatttca | caaaggctac | 1080 |
| aagcatagca | caattaacat | tgtggatatt | tatccaatga | tgtgccacat | cctgggatta | 1140 |
| aaaccacatc | ccaataatgg | gacctttggt | catactaagt | gcttgttagt | tgaccagtgg | 1200 |
| tgcattaatc | tcgactacaa | agacgatgac | gacaagcatc | atcatcatca | tcat | 1254 |

<210> SEQ ID NO 14
<211> LENGTH: 1329
<212> TYPE: DNA
<213> ORGANISM: Artificial
<220> FEATURE:
<223> OTHER INFORMATION: Synthetic construc (DNA encoding tagged protein)

<400> SEQUENCE: 14

| | | | | | |
|---|---|---|---|---|---|
| atgacttcga | aatttctctt | ggtgtccttc | atacttgctg | cactgagtct | ttcaaccacc | 60 |
| ttttctctcc | aaccagacca | gcaaaaggtt | ctactagttt | cttttgatgg | attccgttgg | 120 |
| gattacttat | ataagttcc | aacgccccat | tttcattata | ttatgaaata | tggtgttcac | 180 |
| gtgaagcaag | ttactaatgt | tttttattaca | aaaacctacc | ctaaccatta | tactttggta | 240 |
| actggcctct | tgcagagaa | tcatgggatt | gttgcaaatg | atatgtttga | tcctattcgg | 300 |
| aacaaatctt | tctccttgga | tcacatgaat | atttatgatt | ccaagttttg | ggaagaagcg | 360 |
| acaccaatat | ggatcacaaa | ccagagggca | ggacatacta | gtggtgcagc | catgtggccc | 420 |
| ggaacagatg | taaaaataca | taagcgcttt | cctactcatt | acatgcctta | caatgagtca | 480 |

| | |
|---|---|
| gtttcatttg aagatagagt tgccaaaatt attgaatggt ttacgtcaaa agagcccata | 540 |
| aatcttggtc ttctctattg ggaagaccct gatgacatgg gccaccattt gggacctgac | 600 |
| agtccgctca tggggcctgt catttcagat attgacaaga agttaggata tctcatacaa | 660 |
| atgctgaaaa aggcaaagtt gtggaacact ctgaacctaa tcatcacaag tgatcatgga | 720 |
| atgacgcagt gctctgagga aaggttaata gaacttgacc agtacctgga taaagaccac | 780 |
| tatacccctga ttgatcaatc tccagtagca gccatcttgc caaaagaagg taaatttgat | 840 |
| gaagtctatg aagcactaac tcacgctcat cctaatctta ctgtttacaa aaaagaagac | 900 |
| gttccagaaa ggtggcatta caaatacaac agtcgaattc aaccaatcat agcagtggct | 960 |
| gatgaagggt ggcacatttt acagaataag tcagatgact ttctgttagg caaccacggt | 1020 |
| tacgataatg cgttagcaga tatgcatcca atatttttag cccatggtcc tgccttcaga | 1080 |
| aagaatttct caaaagaagc catgaactcc acagatttgt acccactact atgccacctc | 1140 |
| ctcaatatca ccgccatgcc acacaatgga tcattctgga atgtccagga tctgctcaat | 1200 |
| tcagcaatgc caagggtggt cccttataca cagagtacta tactcctccc tggtagtgtt | 1260 |
| aaaccagcag aatatgacca agagggggac tacaaagacg atgacgacaa gcatcatcat | 1320 |
| catcatcat | 1329 |

<210> SEQ ID NO 15
<211> LENGTH: 1311
<212> TYPE: DNA
<213> ORGANISM: Artificial
<220> FEATURE:
<223> OTHER INFORMATION: Synthetic construct (DNA encoding tagged protein)

<400> SEQUENCE: 15

| | |
|---|---|
| atggcagtga agcttgggac cctcctgctg gcccttgccc tgggcctggc ccagccagcc | 60 |
| tctgcccgcc ggaagctgct ggtgtttctg ctggatggtt ttcgctcaga ctacatcagt | 120 |
| gatgaggcgc tggagtcatt gcctggtttc aaagagattg tgagcagggg agtaaaagtg | 180 |
| gattacttga ctccagactt ccctagtctc tcgtatccca attattatac cctaatgact | 240 |
| ggccgccatt gtgaagtcca tcagatgatc gggaactaca tgtgggaccc caccaccaac | 300 |
| aagtcctttg acattggcgt caacaaagac agcctaatgc ctctctggtg aatggatca | 360 |
| gaacctctgt gggtcactct gaccaaggcc aaaaggaagg tctacatgta ctactggcca | 420 |
| ggctgtgagg ttgagattct gggtgtcaga cccaccctact gcctagaata taaaaatgtc | 480 |
| ccaacggata tcaatttgc caatgcagtc agcgatgctc ttgactcctt caagagtggc | 540 |
| cgggccgacc tggcagccat ataccatgag cgcattgacg tggaaggcca ccactacggg | 600 |
| cctgcatctc cgcagaggaa agatgccctc aaggctgtag acactgtcct gaagtacatg | 660 |
| accaagtgga tccaggagcg gggcctgcag gaccgcctga acgtcattat tttctcggat | 720 |
| cacggaatga ccgacatttt ctggatggac aaagtgattg agctgaataa gtacatcagc | 780 |
| ctgaatgacc tgcagcaagt gaaggaccgc gggcctgttg tgagcctttg gccggcccct | 840 |
| gggaaacact ctgagatata taacaaactg agcacagtgg aacacatgac tgtctacgag | 900 |
| aaagaagcca tcccaagcag gttctattac aagaaaggaa agtttgtctc tcctttgact | 960 |
| ttagtggctg atgaaggctg gttcataact gagaatcaga gatgcttcc gttttggatg | 1020 |
| aacagcaccg gcaggcggga aggttggcag cgtggatggc acggctacga caacgagctc | 1080 |
| atggacatgc ggggcatctt cctggccttc ggacctgatt tcaaatccaa cttcagagct | 1140 |
| gctcctatca ggtcggtgga cgtctacaat gtcatgtgca atgtggtggg catcaccccg | 1200 |

```
ctgcccaaca acggatcctg gtccagggtg atgtgcatgc tgaagggccg cgccagcact    1260
gccccgcctg actacaaaga cgatgacgac aagcatcatc atcatcatca t             1311
```

<210> SEQ ID NO 16
<211> LENGTH: 20
<212> TYPE: DNA
<213> ORGANISM: Artificial
<220> FEATURE:
<223> OTHER INFORMATION: Synthetic construct (Primer)

<400> SEQUENCE: 16

```
acatttccaa accactacag                                                  20
```

<210> SEQ ID NO 17
<211> LENGTH: 20
<212> TYPE: DNA
<213> ORGANISM: Artificial
<220> FEATURE:
<223> OTHER INFORMATION: Synthetic construct (Primer)

<400> SEQUENCE: 17

```
aacaagcact tagtatgacc                                                  20
```

<210> SEQ ID NO 18
<211> LENGTH: 19
<212> TYPE: DNA
<213> ORGANISM: Artificial
<220> FEATURE:
<223> OTHER INFORMATION: Synthetic construct (Primer)

<400> SEQUENCE: 18

```
acaaaaacct accctaacc                                                   19
```

<210> SEQ ID NO 19
<211> LENGTH: 22
<212> TYPE: DNA
<213> ORGANISM: Artificial
<220> FEATURE:
<223> OTHER INFORMATION: Synthetic construct (Primer)

<400> SEQUENCE: 19

```
taatgctgcc aagagagacc cc                                               22
```

<210> SEQ ID NO 20
<211> LENGTH: 22
<212> TYPE: DNA
<213> ORGANISM: Artificial
<220> FEATURE:
<223> OTHER INFORMATION: Synthetic construct (Primer)

<400> SEQUENCE: 20

```
tcaacaaaga cagcctaatg cc                                               22
```

<210> SEQ ID NO 21
<211> LENGTH: 19
<212> TYPE: DNA
<213> ORGANISM: Artificial
<220> FEATURE:
<223> OTHER INFORMATION: Synthetic construct (Primer)

<400> SEQUENCE: 21

```
atccacgctg ccaaccttc                                                   19
```

<210> SEQ ID NO 22
<211> LENGTH: 359

```
<212> TYPE: DNA
<213> ORGANISM: Artificial
<220> FEATURE:
<223> OTHER INFORMATION: Synthetic construct (probe)

<400> SEQUENCE: 22
ccctcagtca taccaagtgc ttgttggtgg accagtggtg cattaatctc ccagaagcca      60
ttggaattgt tgttagtgca ctattggtat taaccatgct aacaggcctc atgatattca     120
tgcggagcag agcatccaca tcccgtccat tctcccgtct tcagctgcag gaagatgacg     180 atgaccctt aattgattaa ttcaccatgt cttattaatt tcaaaactaa ggatccatgc      240
aaggagtggt gttacagcca taaaaaggt atatttcaaa agacaagaca cacatggcaa      300
aattactctg gggtgtgtgt gtgtgtgtgt gtgtgtgtgc cctgttttgg tgtgttgcc      359

<210> SEQ ID NO 23
<211> LENGTH: 356
<212> TYPE: DNA
<213> ORGANISM: Artificial
<220> FEATURE:
<223> OTHER INFORMATION: Synthetic construct (probe)

<400> SEQUENCE: 23
gtactcactg ctctgccacc tcctcaatct caccgccctg ccacacaatg gatcattctg      60
gaatgtccag gaccttctca gttcagcaac tcccaagcca attccttaca cacagagtac     120
cacactcctc cttgggagtg acaaaccagg ggaggatgag caagaggaat cgtacccta     180 ttacataggt gtctctcttg gcagcatcat agctatggta ttctttgtag ttctcattaa     240
gcatttaata cgcagtcaag tgcatacttt acaatatagg caggtcgaag ttgctcaacc     300
gttactccaa gcttagtgct tctttgacat ggaatggcag atcaaagtgg agggtc         356

<210> SEQ ID NO 24
<211> LENGTH: 432
<212> TYPE: DNA
<213> ORGANISM: Artificial
<220> FEATURE:
<223> OTHER INFORMATION: Synthetic construct (probe)

<400> SEQUENCE: 24
gaaagccagg aggaaagtct acatgtatta ctggcccggc tgtgaagttg agattcttgg      60
tgtcagacca acttactgcc tagaatataa aactgtccca acagatatca actttgcgaa     120
tgcagttagc gatgctctcg actcattaaa gagtggccga gcggatctag cagccatata     180
ccatgagcgc atcgatgtag aaggtcacca ctacggccct tcatcacctc agagaaaaga     240
tgccctcaga gctgtggaca ctgtcctgaa gtatatgatc cagtggattc aggaccgagg     300
cctgcagcag gacctaaacg tcatcctctt ctcagaccat gggatgactg acatcttctg     360
gatggataaa gtgattgagc tgagcaacta catcagcctg gacgacctgc agcaagtgaa     420
agaccgaggg cc                                                          432

<210> SEQ ID NO 25
<211> LENGTH: 1212
<212> TYPE: DNA
<213> ORGANISM: Homo sapiens

<400> SEQUENCE: 25
atgaagttat tagtaatact tttgtttttct ggacttataa ctggttttag aagtgactct      60
tcctctagtt tgccacctaa gttactacta gtatcctttg atggcttcag agctgattat     120
ctgaagaact atgaatttcc tcatctccag aattttatca aagaaggtgt tttggtagag     180
```

```
catgttaaaa atgtttttat cacaaaaaca tttccaaacc actacagtat tgtgacaggc    240
ttgtatgaag aaagccatgg cattgtggct aattccatgt atgatgcagt cacaaagaaa    300
cacttttctg actctaatga caaggatcct ttttggtgga atgaggcagt acctatttgg    360
gtgaccaatc agcttcagga aaacagatca agtgctgctg ctatgtggcc tggtactgat    420
gtacccattc acgataccat ctcttcctat tttatgaatt acaactcctc agtgtcattt    480
gaggaaagac taaataatat tactatgtgg ctaaacaatt cgaacccacc agtcaccttt    540
gcaacactat attgggaaga accagatgca agtggccaca atacggacc tgaagataaa    600 gaaaacatga gcagagtgtt gaaaaaaata gatgatctta tcggtgactt agtccaaaga    660
ctcaagatgt tagggctatg ggaaaatctt aatgtgatca ttacaagtga tcatgggatg    720
acccagtgtt ctcaggacag actgataaac ctggattcct gcatcgatca ttcatactac    780
actcttatag atttgagccc agttgctgca atacttccca aaataaatag aacagaggtt    840
tataacaaac tgaaaaactg tagccctcat atgaatgttt atctcaaaga agacattcct    900
aacagatttt attaccaaca taatgatcga attcagccca ttattttggt tgccgatgaa    960
ggctggacaa ttgtgctaaa tgaatcatca caaaaattag gtgaccatgg ttatgataat   1020
tctttgccta gtatgcatcc atttctagct gcccacggac ctgcatttca caaaggctac   1080
aagcatagca caattaacat tgtggatatt tatccaatga tgtgccacat cctgggatta   1140
aaaccacatc ccaataatgg gacctttggt catactaagt gcttgttagt tgaccagtgg   1200
tgcattaatc tc                                                       1212

<210> SEQ ID NO 26
<211> LENGTH: 1287
<212> TYPE: DNA
<213> ORGANISM: Homo sapiens

<400> SEQUENCE: 26
atgacttcga aatttctctt ggtgtccttc atacttgctg cactgagtct ttcaaccacc     60
ttttctctcc aaccagacca gcaaaaggtt ctactagttt cttttgatgg attccgttgg    120
gattacttat ataaagttcc aacgccccat tttcattata ttatgaaata tggtgttcac    180
gtgaagcaag ttactaatgt ttttattaca aaaacctacc ctaaccatta tactttggta    240
actggcctct tgcagagaaa tcatgggatt gttgcaaatg atatgtttga tcctattcgg    300
aacaaatctt tctccttgga tcacatgaat attatgatt ccaagttttg ggaagaagcg    360
acaccaatat ggatcacaaa ccagagggca ggacatacta gtggtgcagc catgtggccc    420
ggaacagatg taaaaataca taagcgcttt cctactcatt acatgcctta caatgagtca    480
gtttcatttg aagatagagt tgccaaaatt attgaatggt ttacgtcaaa agagcccata    540
aatcttggtc ttctctattg gaagacccct gatgacatgg ccaccatttt gggacctgac    600
agtccgctca tggggcctgt catttcagat attgacaaga agttaggata tctcatacaa    660
atgctgaaaa aggcaaagtt gtggaacact ctgaacctaa tcatcacaag tgatcatgga    720
atgacgcagt gctctgagga aggttaata gaacttgacc agtacctgga taagaccac    780 tatacccctga ttgatcaatc tccagtagca gccatcttgc aaaagaagg taaatttgat    840 gaagtctatg aagcactaac tcacgctcat cctaatctta ctgttacaa aaaagaagac    900 gttccagaaa ggtggcatta caaatacaac agtcgaattc aaccaatcat agcagtggct    960
gatgaagggg ggcacatttt acagaataag tcagatgact ttctgttagg caaccacggt   1020
tacgataatg cgttagcaga tatgcatcca atatttttag cccatggtcc tgccttcaga   1080
```

-continued

```
aagaatttct caaaagaagc catgaactcc acagatttgt acccactact atgccacctc      1140
ctcaatatca ccgccatgcc acacaatgga tcattctgga atgtccagga tctgctcaat      1200
tcagcaatgc caagggtggt cccttataca cagagtacta tactcctccc tggtagtgtt      1260
aaaccagcag aatatgacca agagggg                                          1287
```

<210> SEQ ID NO 27
<211> LENGTH: 1269
<212> TYPE: DNA
<213> ORGANISM: Homo sapiens

<400> SEQUENCE: 27

```
atggcagtga agcttgggac cctcctgctg gcccttgccc tgggcctggc ccagccagcc        60
tctgcccgcc ggaagctgct ggtgtttctg ctggatggtt ttcgctcaga ctacatcagt       120
gatgaggcgc tggagtcatt gcctggtttc aaagagattg tgagcagggg agtaaaagtg       180
gattacttga ctccagactt ccctagtctc tcgtatccca attattatac ctaatgact        240 ggccgccatt gtgaagtcca tcagatgatc gggaactaca tgtgggaccc caccaccaac       300
aagtcctttg acattggcgt caacaaagac agcctaatgc ctctctggtg aatggatca        360 gaacctctgt gggtcactct gaccaaggcc aaaaggaagg tctacatgta ctactggcca       420
ggctgtgagt tgagattct gggtgtcaga cccacctact gcctagaata taaaaatgtc       480
ccaacggata tcaattttgc caatgcagtc agcgatgctc ttgactcctt caagagtggc       540
cgggccgacc tggcagccat ataccatgag cgcattgacg tggaaggcca ccactacggg       600
cctgcatctc cgcagaggaa agatgccctc aaggctgtag acactgtcct gaagtacatg       660
accaagtgga tccaggagcg gggcctgcag gaccgcctga acgtcattat tttctcggat       720
cacggaatga ccgacatttt ctggatggac aaagtgattg agctgaataa gtacatcagc       780
ctgaatgacc tgcagcaagt gaaggaccgc gggcctgttg tgagcctttg gccggcccct       840
gggaaacact ctgagatata taacaaactg agcacagtgg aacacatgac tgtctacgag       900
aaagaagcca tcccaagcag gttctattac aagaaaggaa agtttgtctc tccttttgact       960 ttagtggctg atgaaggctg gttcataact gagaatcgag agatgcttcc gttttggatg      1020
aacagcaccg gcaggcggga aggttggcag cgtggatggc acggctacga caacgagctc      1080
atggacatgc ggggcatctt cctggccttc ggacctgatt tcaaatccaa cttcagagct      1140
gctcctatca ggtcggtgga cgtctacaat gtcatgtgca atgtggtggg catcaccccg      1200
ctgcccaaca acggatcctg gtccagggtg atgtgcatgc tgaagggccg cgccagcact      1260
gccccgcct                                                              1269
```

<210> SEQ ID NO 28
<211> LENGTH: 404
<212> TYPE: PRT
<213> ORGANISM: Homo sapiens

<400> SEQUENCE: 28

```
Met Lys Leu Leu Val Ile Leu Leu Phe Ser Gly Leu Ile Thr Gly Phe
1               5                   10                  15

Arg Ser Asp Ser Ser Ser Ser Leu Pro Pro Lys Leu Leu Val Ser
            20                  25                  30

Phe Asp Gly Phe Arg Ala Asp Tyr Leu Lys Asn Tyr Glu Phe Pro His
        35                  40                  45

Leu Gln Asn Phe Ile Lys Glu Gly Val Leu Val Glu His Val Lys Asn
    50                  55                  60
```

Val Phe Ile Thr Lys Thr Phe Pro Asn His Tyr Ser Ile Val Thr Gly
65                  70                  75                  80

Leu Tyr Glu Glu Ser His Gly Ile Val Ala Asn Ser Met Tyr Asp Ala
            85                  90                  95

Val Thr Lys Lys His Phe Ser Asp Ser Asn Asp Lys Asp Pro Phe Trp
            100                 105                 110

Trp Asn Glu Ala Val Pro Ile Trp Val Thr Asn Gln Leu Gln Glu Asn
            115                 120                 125

Arg Ser Ser Ala Ala Ala Met Trp Pro Gly Thr Asp Val Pro Ile His
130                 135                 140

Asp Thr Ile Ser Ser Tyr Phe Met Asn Tyr Asn Ser Ser Val Ser Phe
145                 150                 155                 160

Glu Glu Arg Leu Asn Asn Ile Thr Met Trp Leu Asn Asn Ser Asn Pro
                165                 170                 175

Pro Val Thr Phe Ala Thr Leu Tyr Trp Glu Glu Pro Asp Ala Ser Gly
            180                 185                 190

His Lys Tyr Gly Pro Glu Asp Lys Glu Asn Met Ser Arg Val Leu Lys
            195                 200                 205

Lys Ile Asp Asp Leu Ile Gly Asp Leu Val Gln Arg Leu Lys Met Leu
210                 215                 220

Gly Leu Trp Glu Asn Leu Asn Val Ile Ile Thr Ser Asp His Gly Met
225                 230                 235                 240

Thr Gln Cys Ser Gln Asp Arg Leu Ile Asn Leu Asp Ser Cys Ile Asp
                245                 250                 255

His Ser Tyr Tyr Thr Leu Ile Asp Leu Ser Pro Val Ala Ala Ile Leu
            260                 265                 270

Pro Lys Ile Asn Arg Thr Glu Val Tyr Asn Lys Leu Lys Asn Cys Ser
            275                 280                 285

Pro His Met Asn Val Tyr Leu Lys Glu Asp Ile Pro Asn Arg Phe Tyr
        290                 295                 300

Tyr Gln His Asn Asp Arg Ile Gln Pro Ile Ile Leu Val Ala Asp Glu
305                 310                 315                 320

Gly Trp Thr Ile Val Leu Asn Glu Ser Ser Gln Lys Leu Gly Asp His
                325                 330                 335

Gly Tyr Asp Asn Ser Leu Pro Ser Met His Pro Phe Leu Ala Ala His
            340                 345                 350

Gly Pro Ala Phe His Lys Gly Tyr Lys His Ser Thr Ile Asn Ile Val
            355                 360                 365

Asp Ile Tyr Pro Met Met Cys His Ile Leu Gly Leu Lys Pro His Pro
370                 375                 380

Asn Asn Gly Thr Phe Gly His Thr Lys Cys Leu Leu Val Asp Gln Trp
385                 390                 395                 400

Cys Ile Asn Leu

<210> SEQ ID NO 29
<211> LENGTH: 429
<212> TYPE: PRT
<213> ORGANISM: Homo sapiens

<400> SEQUENCE: 29

Met Thr Ser Lys Phe Leu Leu Val Ser Phe Ile Leu Ala Ala Leu Ser
1               5                   10                  15

Leu Ser Thr Thr Phe Ser Leu Gln Pro Asp Gln Gln Lys Val Leu Leu
            20                  25                  30

-continued

Val Ser Phe Asp Gly Phe Arg Trp Asp Tyr Leu Tyr Lys Val Pro Thr
        35                  40                  45

Pro His Phe His Tyr Ile Met Lys Tyr Gly Val His Val Lys Gln Val
    50                  55                  60

Thr Asn Val Phe Ile Thr Lys Thr Tyr Pro Asn His Tyr Thr Leu Val
65                  70                  75                  80

Thr Gly Leu Phe Ala Glu Asn His Gly Ile Val Ala Asn Asp Met Phe
                85                  90                  95

Asp Pro Ile Arg Asn Lys Ser Phe Ser Leu Asp His Met Asn Ile Tyr
            100                 105                 110

Asp Ser Lys Phe Trp Glu Glu Ala Thr Pro Ile Trp Ile Thr Asn Gln
            115                 120                 125

Arg Ala Gly His Thr Ser Gly Ala Ala Met Trp Pro Gly Thr Asp Val
        130                 135                 140

Lys Ile His Lys Arg Phe Pro Thr His Tyr Met Pro Tyr Asn Glu Ser
145                 150                 155                 160

Val Ser Phe Glu Asp Arg Val Ala Lys Ile Ile Glu Trp Phe Thr Ser
                165                 170                 175

Lys Glu Pro Ile Asn Leu Gly Leu Leu Tyr Trp Glu Asp Pro Asp Asp
            180                 185                 190

Met Gly His His Leu Gly Pro Asp Ser Pro Leu Met Gly Pro Val Ile
        195                 200                 205

Ser Asp Ile Asp Lys Lys Leu Gly Tyr Leu Ile Gln Met Leu Lys Lys
210                 215                 220

Ala Lys Leu Trp Asn Thr Leu Asn Leu Ile Ile Thr Ser Asp His Gly
225                 230                 235                 240

Met Thr Gln Cys Ser Glu Glu Arg Leu Ile Glu Leu Asp Gln Tyr Leu
                245                 250                 255

Asp Lys Asp His Tyr Thr Leu Ile Asp Gln Ser Pro Val Ala Ala Ile
            260                 265                 270

Leu Pro Lys Glu Gly Lys Phe Asp Glu Val Tyr Glu Ala Leu Thr His
        275                 280                 285

Ala His Pro Asn Leu Thr Val Tyr Lys Lys Glu Asp Val Pro Glu Arg
    290                 295                 300

Trp His Tyr Lys Tyr Asn Ser Arg Ile Gln Pro Ile Ile Ala Val Ala
305                 310                 315                 320

Asp Glu Gly Trp His Ile Leu Gln Asn Lys Ser Asp Phe Leu Leu
                325                 330                 335

Gly Asn His Gly Tyr Asp Asn Ala Leu Ala Asp Met His Pro Ile Phe
            340                 345                 350

Leu Ala His Gly Pro Ala Phe Arg Lys Asn Phe Ser Lys Glu Ala Met
        355                 360                 365

Asn Ser Thr Asp Leu Tyr Pro Leu Leu Cys His Leu Leu Asn Ile Thr
    370                 375                 380

Ala Met Pro His Asn Gly Ser Phe Trp Asn Val Gln Asp Leu Leu Asn
385                 390                 395                 400

Ser Ala Met Pro Arg Val Val Pro Tyr Thr Gln Ser Thr Ile Leu Leu
                405                 410                 415

Pro Gly Ser Val Lys Pro Ala Glu Tyr Asp Gln Glu Gly
            420                 425

<210> SEQ ID NO 30
<211> LENGTH: 423
<212> TYPE: PRT
<213> ORGANISM: Homo sapiens

<400> SEQUENCE: 30

```
Met Ala Val Lys Leu Gly Thr Leu Leu Ala Leu Ala Leu Gly Leu
1               5                   10                  15

Ala Gln Pro Ala Ser Ala Arg Arg Lys Leu Leu Val Phe Leu Leu Asp
            20                  25                  30

Gly Phe Arg Ser Asp Tyr Ile Ser Asp Glu Ala Leu Glu Ser Leu Pro
            35                  40                  45

Gly Phe Lys Glu Ile Val Ser Arg Gly Val Lys Val Asp Tyr Leu Thr
    50                  55                  60

Pro Asp Phe Pro Ser Leu Ser Tyr Pro Asn Tyr Tyr Thr Leu Met Thr
65              70                  75                  80

Gly Arg His Cys Glu Val His Gln Met Ile Gly Asn Tyr Met Trp Asp
                85                  90                  95

Pro Thr Thr Asn Lys Ser Phe Asp Ile Gly Val Asn Lys Asp Ser Leu
                100                 105                 110

Met Pro Leu Trp Trp Asn Gly Ser Glu Pro Leu Trp Val Thr Leu Thr
            115                 120                 125

Lys Ala Lys Arg Lys Val Tyr Met Tyr Tyr Trp Pro Gly Cys Glu Val
130                 135                 140

Glu Ile Leu Gly Val Arg Pro Thr Tyr Cys Leu Glu Tyr Lys Asn Val
145                 150                 155                 160

Pro Thr Asp Ile Asn Phe Ala Asn Ala Val Ser Asp Ala Leu Asp Ser
                165                 170                 175

Phe Lys Ser Gly Arg Ala Asp Leu Ala Ala Ile Tyr His Glu Arg Ile
            180                 185                 190

Asp Val Glu Gly His His Tyr Gly Pro Ala Ser Pro Gln Arg Lys Asp
            195                 200                 205

Ala Leu Lys Ala Val Asp Thr Val Leu Lys Tyr Met Thr Lys Trp Ile
        210                 215                 220

Gln Glu Arg Gly Leu Gln Asp Arg Leu Asn Val Ile Ile Phe Ser Asp
225                 230                 235                 240

His Gly Met Thr Asp Ile Phe Trp Met Asp Lys Val Ile Glu Leu Asn
                245                 250                 255

Lys Tyr Ile Ser Leu Asn Asp Leu Gln Gln Val Lys Asp Arg Gly Pro
            260                 265                 270

Val Val Ser Leu Trp Pro Ala Pro Gly Lys His Ser Glu Ile Tyr Asn
        275                 280                 285

Lys Leu Ser Thr Val Glu His Met Thr Val Tyr Glu Lys Glu Ala Ile
290                 295                 300

Pro Ser Arg Phe Tyr Tyr Lys Lys Gly Lys Phe Val Ser Pro Leu Thr
305                 310                 315                 320

Leu Val Ala Asp Glu Gly Trp Phe Ile Thr Glu Asn Arg Glu Met Leu
                325                 330                 335

Pro Phe Trp Met Asn Ser Thr Gly Arg Arg Glu Gly Trp Gln Arg Gly
            340                 345                 350

Trp His Gly Tyr Asp Asn Glu Leu Met Asp Met Arg Gly Ile Phe Leu
        355                 360                 365

Ala Phe Gly Pro Asp Phe Lys Ser Asn Phe Arg Ala Ala Pro Ile Arg
370                 375                 380

Ser Val Asp Val Tyr Asn Val Met Cys Asn Val Val Gly Ile Thr Pro
385                 390                 395                 400

Leu Pro Asn Asn Gly Ser Trp Ser Arg Val Met Cys Met Leu Lys Gly
                405                 410                 415
```

```
Arg Ala Ser Thr Ala Pro Pro
            420
```

The invention claimed is:
1. An isolated protein consisting of the amino acid sequence of SEQ ID NO: 7.
2. An isolated protein consisting of the amino acid sequence of SEQ ID NO: 28.

* * * * *